US008268585B2

(12) United States Patent
Emalfarb et al.

(10) Patent No.: US 8,268,585 B2
(45) Date of Patent: *Sep. 18, 2012

(54) TRANSFORMATION SYSTEM IN THE FIELD OF FILAMENTOUS FUNGAL HOSTS

(75) Inventors: Mark Aaron Emalfarb, Jupiter, FL (US); Richard Paul Burlingame, Manitowoc, WI (US); Philip Terry Olson, Manitowoc, WI (US); Arkady Panteleimonovich Sinitsyn, Moscow (RU); Martine Parriche, Toulouse (FR); Jean Christophe Bousson, Quint-Fonsegrives (FR); Christine Marie Pynnonen, Appleton, WI (US); Peter Jan Punt, Houten (NL); Cornelia Maria Johanna Van Zeijl, Vleuten-de Meern (NL)

(73) Assignee: Dyadic International (USA), Inc., Jupiter, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/047,709

(22) Filed: Mar. 13, 2008

(65) Prior Publication Data

US 2008/0194005 A1 Aug. 14, 2008

Related U.S. Application Data

(63) Continuation of application No. 10/394,568, filed on Mar. 21, 2003, now Pat. No. 7,399,627, which is a continuation of application No. 09/548,938, filed on Apr. 13, 2000, now Pat. No. 6,573,086, which is a continuation-in-part of application No. PCT/NL99/00618, filed on Oct. 6, 1999, which is a continuation-in-part of application No. PCT/EP98/06496, filed on Oct. 6, 1998.

(51) Int. Cl.
*C12P 21/02* (2006.01)
(52) U.S. Cl. .................................. 435/69.1; 435/254.11
(58) Field of Classification Search ........................ None
See application file for complete search history.

(56) References Cited

U.S. PATENT DOCUMENTS

| | | |
|---|---|---|
| 2,974,001 A | 3/1961 | Windblicher et al. |
| 3,844,890 A | 10/1974 | Horikoshi et al. |
| 3,966,543 A | 6/1976 | Cayle et al. |
| 4,081,328 A | 3/1978 | Skinner et al. |
| 4,435,307 A | 3/1984 | Barbesgaard et al. |
| 4,443,355 A | 4/1984 | Murata et al. |
| 4,462,307 A | 7/1984 | Wells |
| 4,479,881 A | 10/1984 | Tai |
| 4,486,533 A | 12/1984 | Lambowitz |
| 4,610,800 A | 9/1986 | Durham et al. |
| 4,661,289 A | 4/1987 | Parslow et al. |
| 4,816,405 A | 3/1989 | Yelton et al. |
| 4,832,864 A | 5/1989 | Olson |
| 4,885,249 A | 12/1989 | Buxton et al. |
| 4,912,056 A | 3/1990 | Olson |
| 4,935,349 A | 6/1990 | McKnight et al. |
| 4,940,838 A | 7/1990 | Schilperoort et al. |
| 5,006,126 A | 4/1991 | Olson et al. |
| 5,120,463 A | 6/1992 | Bjork et al. |
| 5,122,159 A | 6/1992 | Olson et al. |
| 5,198,345 A | 3/1993 | Gwynne et al. |
| 5,223,409 A | 6/1993 | Ladner et al. |
| 5,252,726 A | 10/1993 | Woldike |
| 5,290,474 A | 3/1994 | Clarkson et al. |
| 5,362,638 A | 11/1994 | Dahiya |
| 5,364,770 A | 11/1994 | Berka et al. |
| 5,436,158 A | 7/1995 | Takagi et al. |
| 5,457,046 A | 10/1995 | Woldike et al. |
| 5,464,763 A | 11/1995 | Schilperoort et al. |
| 5,503,991 A | 4/1996 | Gwynne et al. |
| 5,516,670 A | 5/1996 | Kuehnle et al. |
| 5,536,661 A | 7/1996 | Boel et al. |
| 5,565,332 A | 10/1996 | Hoogenboom et al. |
| 5,578,463 A | 11/1996 | Berka et al. |
| 5,602,004 A | 2/1997 | Jensen et al. |
| 5,604,129 A | 2/1997 | Jensen et al. |
| 5,605,793 A | 2/1997 | Stemmer |
| 5,627,052 A | 5/1997 | Schrader |
| 5,686,593 A | 11/1997 | Woldike et al. |
| 5,695,965 A | 12/1997 | Stuart et al. |
| 5,695,985 A | 12/1997 | Jensen et al. |

(Continued)

FOREIGN PATENT DOCUMENTS

EP 0239400 A2 9/1987

(Continued)

OTHER PUBLICATIONS

Bergès, T. et al., "Cloning of an *Aspergillus niger* invertase gene by expression in *Trichoderma reesei*", Springer-verlag, vol. 24., pp. 53-59, 1993.

Clark, D.S., "Submerged Citric Acid Fermentation of Ferrocyanide-Treated Beet Molasses: Morphology of Pellets of *Aspergillus niger*," Canadian Journal of Microbiology, vol. 8, 1962, pp. 133-136.

Dai, Ziyu et al., "Identification of Genes Associated with Morphology in *Aspergillus niger* by Using Suppression Subtractive Hybridization," Applied and Environmental Microbiology, Apr. 2004, pp. 2474-2485.

(Continued)

*Primary Examiner* — Jim Ketter

(74) *Attorney, Agent, or Firm* — Michael J. Keller; Roetzel & Andress

(57) ABSTRACT

A novel transformation system in the field of filamentous fungal hosts for expressing and secreting heterologous proteins or polypeptides is described. The invention also covers a process for producing large amounts of polypeptide or protein in an economical manner. The system comprises a transformed or transfected fungal strain of the genus *Chrysosporium*, more particularly of *Chrysosporium lucknowense* and mutants or derivatives thereof. It also covers transformants containing *Chrysosporium* coding sequences, as well expression-regulating sequences of *Chrysosporium* genes. Also provided are novel fungal enzymes and their encoding sequences and expression-regulating sequences.

64 Claims, 36 Drawing Sheets

U.S. PATENT DOCUMENTS

| | | | |
|---|---|---|---|
| 5,705,358 | A | 1/1998 | Gouka et al. |
| 5,728,547 | A | 3/1998 | Gwynne et al. |
| 5,753,477 | A | 5/1998 | Chan |
| 5,763,192 | A | 6/1998 | Kauffman et al. |
| 5,763,254 | A | 6/1998 | Wöldike et al. |
| 5,770,356 | A | 6/1998 | Light, II et al. |
| 5,776,730 | A | 7/1998 | Stuart |
| 5,780,279 | A | 7/1998 | Matthews et al. |
| 5,783,385 | A | 7/1998 | Treco et al. |
| 5,783,431 | A | 7/1998 | Peterson et al. |
| 5,811,381 | A | 9/1998 | Emalfarb et al. |
| 5,820,866 | A | 10/1998 | Kappler et al. |
| 5,824,485 | A | 10/1998 | Thompson et al. |
| 5,830,696 | A | 11/1998 | Short |
| 5,834,191 | A | 11/1998 | Radford et al. |
| 5,837,847 | A | 11/1998 | Royer et al. |
| 5,849,541 | A | 12/1998 | Vinci et al. |
| 5,858,657 | A | 1/1999 | Winter et al. |
| 5,871,907 | A | 2/1999 | Winter et al. |
| 5,879,921 | A | 3/1999 | Cherry et al. |
| 5,939,250 | A | 8/1999 | Short |
| 5,955,316 | A | 9/1999 | Conneely et al. |
| 5,958,672 | A | 9/1999 | Short |
| 5,965,384 | A | 10/1999 | Boel et al. |
| 5,969,108 | A | 10/1999 | McCafferty et al. |
| 5,989,814 | A | 11/1999 | Frankel et al. |
| 6,015,707 | A | 1/2000 | Emalfarb et al. |
| 6,017,731 | A | 1/2000 | Tekamp-Olson et al. |
| 6,022,725 | A | 2/2000 | Fowler et al. |
| 6,025,185 | A | 2/2000 | Christensen et al. |
| 6,030,779 | A | 2/2000 | Short |
| 6,046,021 | A | 4/2000 | Bochner |
| 6,054,267 | A | 4/2000 | Short |
| 6,057,103 | A | 5/2000 | Short |
| 6,060,305 | A | 5/2000 | Royer et al. |
| 6,066,493 | A | 5/2000 | Shuster et al. |
| 6,121,034 | A | 9/2000 | Laroche et al. |
| 6,184,026 | B1 | 2/2001 | Shuster et al. |
| 6,518,042 | B1 | 2/2003 | Borchert et al. |
| 6,573,068 | B1 | 6/2003 | Edwards et al. |
| 6,573,086 | B1* | 6/2003 | Emalfrab et al. ........ 435/254.11 |
| 7,122,330 | B2 | 10/2006 | Emalfarb et al. |
| 7,399,627 | B2* | 7/2008 | Emalfarb et al. ........ 435/254.11 |
| 7,794,962 | B2 | 9/2010 | Emalfarb et al. |
| 7,883,872 | B2 | 2/2011 | Gusakov et al. |
| 7,892,812 | B2 | 2/2011 | Emalfarb et al. |
| 7,906,309 | B2 | 3/2011 | Emalfarb et al. |
| 2003/0157595 | A1 | 8/2003 | Emalfarb et al. |
| 2003/0176672 | A1 | 9/2003 | Salceda et al. |
| 2004/0002136 | A1 | 1/2004 | Emalfarb et al. |
| 2005/0191736 | A1 | 9/2005 | Brown et al. |
| 2006/0005279 | A1 | 1/2006 | Dotson et al. |
| 2006/0053514 | A1 | 3/2006 | Wu et al. |
| 2006/0105361 | A1 | 5/2006 | Rothstein et al. |
| 2006/0134747 | A1 | 6/2006 | Baldwin et al. |
| 2006/0218671 | A1 | 9/2006 | Brown et al. |
| 2007/0077630 | A1 | 4/2007 | Harris et al. |
| 2009/0280105 | A1 | 11/2009 | Gusakov et al. |

FOREIGN PATENT DOCUMENTS

| | | |
|---|---|---|
| EP | 0220016 B1 | 8/1991 |
| EP | 0194276 B2 | 11/1993 |
| EP | 0239400 B1 | 8/1994 |
| EP | 0451216 B1 | 1/1996 |
| EP | 1 022 335 | 7/2000 |
| EP | 0215594 B2 | 10/2003 |
| GB | 1368599 A | 10/1974 |
| GB | 2094826 A | 9/1982 |
| GB | 2289218 A | 11/1995 |
| JP | 50-132269 A | 10/1975 |
| JP | 11-304666 A | 11/1999 |
| WO | 8601533 A1 | 3/1986 |
| WO | 9100092 A1 | 1/1991 |
| WO | 9100920 A2 | 1/1991 |
| WO | 9109967 A1 | 7/1991 |
| WO | 9109968 A1 | 7/1991 |
| WO | 9213831 A1 | 8/1992 |
| WO | 9307277 A1 | 4/1993 |
| WO | WO 93/11249 | 6/1993 |
| WO | 9404673 A1 | 3/1994 |
| WO | 9413820 A1 | 6/1994 |
| WO | 9602563 A1 | 2/1996 |
| WO | 9629391 A1 | 9/1996 |
| WO | 9709438 A1 | 3/1997 |
| WO | WO 97/13853 | 4/1997 |
| WO | WO 97/26330 | 7/1997 |
| WO | WO 97/27363 | 7/1997 |
| WO | WO 98/15633 | 4/1998 |
| WO | WO 99/32617 | 7/1999 |
| WO | 9951756 A2 | 10/1999 |
| WO | 9964582 A2 | 12/1999 |
| WO | 9967639 A1 | 12/1999 |
| WO | 0000632 A1 | 1/2000 |
| WO | WO 00/20555 | 4/2000 |
| WO | WO 00/50567 | 8/2000 |
| WO | 0056900 A2 | 9/2000 |
| WO | WO 00/56893 | 9/2000 |
| WO | 0078997 A1 | 12/2000 |
| WO | WO 01/09352 | 2/2001 |
| WO | 0125468 A1 | 4/2001 |
| WO | 0179558 A1 | 10/2001 |
| WO | 2004031367 A2 | 4/2004 |

OTHER PUBLICATIONS

Gu, B.J. et al., "A Glue-496 to Ala Polymorphism Leads to Loss of Function of the Human P2X$_7$ Receptor," *J. Bio Chem.*, vol. 276, No. 14, pp. 11135-11142, Apr. 6, 2001.

Konig et al., "Strategies for Penicillin Fermentation in Tower-Loop Reactors," *Biotechnology and Bioengineering*, 1982, vol. XXIV, pp. 259-280.

Short, Jay M. "Recombinant Approaches for Accessing Biodiversity", *Nature Biotechnology*, 1997, vol. 15 pp. 1322-1323.

Unkles, Shiela E. et al., "The development of a homologous transformation system for *Aspergillus oryzae* based on the nitrate assimilation pathway: A convenient and general selection system for filamentous fungal transformation," *Mol. Gen. Genet.*, 1989, vol. 218, pp. 99-104.

Wiebe, Marilyn G., "Characterization of morphological mutants generated spontaneously in glucose-limited, continuous flow cultures of *Fusarium graminearum* A3/5," *Mycol. Res.* 1992, vol. 96, No. 7, pp. 555-562.

Xu, Jiangfeng, et al. "Increased Heterologous Protein Production in *Aspergillus niger* Fermentation through Extracellular Proteases Inhibition by Pelleted Growth," *Biotechnol. Prog.*, 2000, vol. 16, pp. 222-227.

Iikura Hiroshi, et. al: "Cloning of a Gene Encoding a Putative Xylanase with a Cellulose-Binding Domain from *Humicola grisea*", *Bioscience Biotechnology and Biochemistry*, 61, No. 9, 1997, pp. 1593-1595.

Gunf-Fusox, accession No. p46239, Nov. 1, 1995, P.O. Sheppard, et. al.: "The Use of Conserved Cellulase Family-Specific Sequences to Clone Cellulase Homologue cDNAs from *Fusarium oxysporum*."

Accession No. O59937, Aug. 1, 1998, M.C. Ruiz-Roldan, et. al.: *Fusarium oxysporum f.sp. lycopersici*. family F xylanase (XYL3).

Accession No. D63515; Aug. 21, 1995, S. Takishima et al.: "Cloning, Sequencing, and Expression of the Cellulase Genes of *Humicola grisea var. thermoidea*."

P. O. Sheppard, et. al., *Gene*: 150, 1994, pp. 163-167.

Accession No. Q12621, Nov. 1, 1996, S. Takishima et al.: "Cloning, Sequencing, and Expression of the Cellulase Genes of *Humicola grisea var. thermoidea*".

K. Eriksson, et. al.: "Extracellular Enzyme System Utilized by the Fungus *Sporotrichum pulverulentum* (*Chrysosporium lignorum*) for the Breakdown of Cellulose." 1, Separation, Purification and Physico-Chemical Characterisation of Five Endo-1. 4-Beta-Glucanases, *European Journal of Biochemistry*, 51, 1975, pp. 193-206.

Communication, dated Dec. 28, 2000, European Search Report corresponding to European Patent Application No. 00201343.1 completed Dec. 7, 2000.

U.S. Appl. No. 10/394,568, filed Mar. 21, 2003, Emalfarb, et al.

U.S. Appl. No. 09/284,152, filed Jun. 3, 1999, Emalfarb, et al.

U.S. Appl. No. 10/257,629, filed Apr. 13, 2000, Emalfarb, et al.
U.S. Appl. No. 11/487,547, filed Jul. 13, 2006, Gusanov, et al.
U.S. Appl. No. 11/490,761, filed Jul. 21, 2006, Emalfarb, et al.
Agency Response Letter GRAS Notice No. GRN 000292 (Sep. 29, 2009) from Mitchell A. Cheeseman, Acting Director; hyper text transfer protocol://www.fda.gov.
Aleksenko et al. 1997. Autonomous Plasmid Replication in *Aspergillus nidulans*: AMA1 and MATE Elements. Fungal Genetics and Biology, vol. 21, pp. 373-387.
Aleksenko et al. 1996. Gene expression from replicating plasmids in *Aspergillus nidulans*. Mol. Gen. Genet. vol. 253, pp. 242-246.
Archer et al. 1997. The Molecular Biology of Secreted Enzyme Production by Fungi. Critical Reviews in Biotechnology, vol. 17, No. 4, pp. 273-306.
Armesilla et al. 1994. CEL1: a novel cellulose binding protein secreted by *Agaricus bisporus* during growth on crystalline cellulose. FEMS Microbiol. Lett. vol. 116, pp. 293-300.
Arnau et al. 1991. Integrative transformation by homologous recombination in the zygomycete *Mucor circinelloides*. Mol. Gen. Genet., vol. 225, pp. 193-198.
Arnold et al. 1999. Directed evolution of biocatalysts. Current Opinion in chemical Biology, vol. 3, pp. 54-59.
Arnold et al. 1999. Encyclopedia of Bioprocess Technology: Fermentation, Biocatalysis, and Bioseparation. Flickinger et al., eds. John Wiley & Sons, pp. 971-987.
Asgeirsdottir et al. 1999. A Sandwiched-Culture Technique for Evaluation of Heterologous Protein Production in a Filamentous Fungus. Applied and Environmental Microbiology, vol. 65, No. 5, pp. 2250-2252.
Bajpai et al.1998. Deinking with Enzymes: A Review. TAPPI Journal. vol. 81, No. 12, pp. 111-117.
Benen et al. 2000. Characterization of *Aspergillus niger* Pectate Lyase A. Biochemistry, vol. 39, pp. 15563-15569.
Bhatawadekar. 1983. Studies on Optimum Conditions of Dnzymatic Desizing of LTKP Sized Fabric by Cellulase—Steeping and Cellulase-Padding Methods. Journal of the Textile Association, May 1983, pp. 83-86.
Bretthauer et al. 1999. Glycosylation of *Pichia pastoris*-derived proteins. Biotechnol. Appl. Biochem., vol. 30, pp. 193-200.
Bukhtojarov et al. 2004. Cellulase Complex of the Fungus *Chrysosporium* lucknowense: Isolation and Characterization of Endoglucanases and Cellobiohydrolases. Biochemistry (Mosc), May 2004, vol. 69, No. 5, pp. 542-551 (Abstract).
Buxton et al. 1984. The transformation of mycelial spheroplasts of *Neurospora crassa* and the Attempted Isolation of an Autonomous Replicator. Mol. Gen. Genet, vol. 196, pp. 339-344.
Canevascini, G. et al. 1983. Fractionation and Identification of Cellulases and Other Extracellular Enzymes Produced by Sporotrichum (*Chrysosporium*) Thermophile During Growth on Cellulose or Cellobiose. Can. J. Microbiol., vol. 29, pp. 1071-1080.
Chakraborty et al. 1990. Transformation of Filamentous Fungi by Electroporation. Nucleic Acids Research, vol. 18, No. 22, p. 6637.
De Vries, R.P. and Visser, J., 2001. *Aspergillus* enzymes involved in degradation of plant cell wall polysaccharides. Microbiol. Mol. Biol. R., 65, 497-522.
Degroot et al., *Agrobacterium tumefaciens*-mediated transformation of filamentous fungi, Nature Biotechnology, vol. 16, pp. 839-842 (1998).
Deutsch et al., "Intron-exon structures of eukaryotic model organisms," Nucleic Acids Research, vol. 27, No. 15, pp. 3219-3228 (1999).
Ding et al. Cloning of multiple cellulose cDNAs from *Volvariella volvacea* and their differential expression during substrate colonization and fruiting. FEMS Microbiol. Lett 2006, vol. 263, pp. 207-213.
Flanagan, P.W. et al. Physiological Groups of Decomposer Fungi on Tundra Plant Remains. In Soil Organisms and Decomposition in Tundra, A.J. Holding et al., Eds., Tundra Biome Steering Committee (Stockholm), 1974, pp. 159-181.
Foreman et al. Transcriptional Regulation of Biomass-Degrading Enzymes in the Filamentous Fungus *Trichoderma reesei*. J. Biol. Chem. 2003, vol. 278, pp. 31988-31997.

Gems et al., "An 'instant gene bank' method for gene cloning by mutant complementation," Mol. Gen. Genet, vol. 242, pp. 467-471 (1994).
Gems et al., "Co-transformation with autonomously-replicating helper plasmids facilitates gene cloning from an *Aspergillus nidulans* gene library," Curr. Genet., vol. 24, pp. 520-524 (1993).
Gordillo et al. *Penicillium purpurogenum* Produces a Family 1 Acetyl Xylan Esterase Containing a Carbohydrate-Binding Module: Characterization of the Protein and Its Gene. Mycol. Res., 2006, vol. 110, p. 1129.
Goudar et al. Influence of microbial concentration on the rheology of non-Newtonian fermentation broths. Appl. Microbiol. Biiotechnol. 1999, vol. 51, pp. 310-315.
Gunf-Fusox, accession No. p46239, Nov. 1, 1995, P.O. Sheppard et al. The Use of Conserved Cellulase Family-Specific Sequences to Clone Cellulase Homologue cDNAs from *Fusarium oxysporum*.
Gusakov, A.V. et al. Design of Highly Efficient Cellulase Mixtures for Enzymatic Hydrolysis of Cellulose. Biotechnol. Bioeng., 2007, vol. 97, No. 5, pp. 1028-1038.
Gusakov, A.V. et al. Purification, Cloning and Characterization of Two Forms of Thermostable and Highly Active Cellobiohydrolase I (Cel7A) Produced by the Industrial Strain of *Chrysosporium* lucknowense. Enzyme Microb. Technol. 2005, vol. 36, pp. 57-69.
Gusakov, A.V. Microassays to Control the Results of Cellulase Treatment of Denim Fabrics. Textile Chemist and Colorist and American Dyestuff Reporter, 2000, vol. 32, No. 5, pp. 42-47.
Hahn-Hagerdal et al. Bio-ethanol—The Fuel of Tomorrow from the Residues of Today. Trends in Biotechnology, 2006, vol. 24, No. 12, pp. 549-556.
Harmsen Martin C. et al. 1992. Sequence Analysis of the Glyceraldehyde-3-phosphate dehydrogenase genes from the basidiomycetes Schizopyllum commune, *Phanerochaete chrysosporium* and *Agaricus bisporus*. Current Genetics, vol. 22, No. 6, pp. 447-454.
Hong et al. Unusual hydrophobic linker region of B-glucosidase (BGLII) from *Thermoascus aurantiacus* is required for hyper-activation by organic solvents. Applied Microbiol. Biotechnol., 2006, vol. 73, pp. 80-88.
Huertas-Gonzalez et al. Cloning and characterization of pl1 encoding an in planta-secreted pectate lyase of *Fusarium oxysporum*. Curr Genet, 1999, vol. 35, pp. 36-40.
Hurst, J.L. et al Association between *Chrysosporium* Pannorum and Mucor Hiemalis in Poa Flabellata Litter. Trans. Br. Mycol. Soc., 1983, vol. 81, No. 1, pp. 151-153.
Janeckova et al. Ceska Mykologie (1977), vol. 331, No. 4, pp. 206-213 (Abstract).
Jeenes et al., "Heterologous Protein Production by Filamentous Fungi," Biotechnology & Genetic Engineering Reviews, vol. 9, pp. 327-367 (1991).
Johnstone et al. Cloning an *Aspergillus nidulans* developmental gene by transformation. EMBO J., 1985, vol. 4, pp. 1307-1311.
Joo et al., "A high-throughput digital imaging screen for the discovery and directed evolution of oxygenases," Chemistry & Biology, vol. 6, pp. 699-706 (1999).
Judelson et al., "Transformation of the Oomycete Pathogen, Phytophthora infestans," Molecular Plant-Microbe Interactions, vol. 4, No. 6, pp. 602-607 (1991).
Kauppinen et al. Molecular Cloning and Characterization of a Rhamnogalacturonan Acetylesterase from *Aspergillus aculeatus*. J. Biol Chem, 1995, vol. 270, p. 27172-27178.
Kormelink F.J.M. et al. Mode of Action of the Xylan-Degrading Enzymes from *Aspergillus awamori* on Alkali-Extractable Cereal Arabinoxylans. Carbohydr. Res, 1993, vol. 249, pp. 355-367.
Kormelink et al. Purification and Characterization of Three Endo-(1,4)-B-xylanases and one B-xylosidase from *Aspergillus awamori*. J. Biotechnol. 1993, vol. 27, pp. 249-265.
Kotake et al. Molecular cloning and expression in *Escherichia coli* of a *Trichoderma viride* endo-B-(1-6)-galactanase gene. Biochem J.., 2004, vol. 377, pp. 749-755.
Kramer et al. Insect Chitinases: Molecular Biology and Potential Uses as Biopesticides. Insect Biochem Mol Biol., 1997, vol. 27, p. 887.
Kruszewska, "Heterologous expression of genes in filamentous fungi," Acta Biochimica Polonica, vol. 46, No. 1, pp. 181-195 (1999).

Kuchner et al., "Directed evolution of enzyme catalysts," Trends in Microbiology, vol. 15, pp. 523-530 (1997).
Liou et al., "Transformation of a Leu- Mutant of Rhizopus niveus with the leuA Gene of Mucor circinelloides," Biosci. Biotech. Biochem., vol. 56, No. 9, pp. 1503-1504 (1992).
Mandels, M. et al. Induction of Cellulase in *Trichoderma viride* as Influenced by Carbon Sources and Metals. J. Bacteriol., 1957, vol. 73, pp. 269-278.
Mantyla et al. Production in *Trichoderma reesei* xylanases of three xylanases from *Chaetomium thermophilum*: a recombinant thermoxylanase for biobleaching of kraft pulp. Appl. Microbiol. Biotechnol., 2007, vol. 76, pp. 377-386.
Maras et al., "Filamentous fungi as production organisms for glycoproteins of bio-medical interest," Glycoconjugate Journal, vol. 16, pp. 99-107 (1999).
Martinez, D. et al. Genome Sequencing and Analysis of the Biomass-Degrading Fungus *Trichoderma reesei* (syn. Hypocrea Jecorina), Nature Biotechnol., 2008, vol. 26, pp. 553-560.
May et al., "Inverting enantioselectivity by directed evolution of hydantoinase for improved production of L-methionine," Nature Biotechnology, vol. 18, pp. 317-320 (2000).
Meynial-Salles et al. In vitro glycosylation of proteins: An enzymatic approach. J. Biotechnol., 1996, vol. 46, pp. 1-14.
Mielenz. Ethanol Production from Biomass: Technology and Commercialization Status. Current Opinion in Microbiology, 2001, vol. 4, pp. 324-329.
Miyazaki et al., "Directed Evolution Study of Temperature Adaptation in a Psychrophilic Enzyme," J. Mol. Biol., vol. 297, pp. 1015-1026 (2000).
Munoz-Rivas et al., "Transformation of the basidiomycete, Schizophyllum commune," Mol. Gen. Gent., vol. 205, pp. 103-106 (1986).
Oberson, J. et al. Comparative investigation of cellulose-degrading enzyme systems produced by different strains of *Myceliophthora thermophila* (Apinis) v. Oorschot. Enzyme Microb. Technol. 1992, vol. 14, pp. 303-312.
Pages et al. Arhamnogalacturonan Lyase in the *Clostridium cellulolyticum* Cellulosome. J. Bacteriol. vol. 185, pp. 4727-4733 (2003).
Peberdy, "Extracellular Proteins in Fungi: A Cytological and Molecular Perspective," Acta Microbiologica et Immunologica Hungarica, vol. 46, pp. 165-174 (1999).
Qureshi, M.S.A. et al. Cellulolytic Activity of Some Thermophilic and Thermotolerant Fungi of Pakistan, Viologia, vol. 26, Nos. 1-2, 1980, pp. 201-217.
Reese, E.T. et al. Beta-D-1,3 Glucanases in Fungi. Can. J. Microbiol. 1959, vol. 5, pp. 173-185.
Ridder, R. et al. 1992. Sequence Analysis of the Gene Coding for Glyceraldehyde-3-Phosphate Dehydrogenase GPD of *Podospora-anserina* use of Homologous Regulatory Sequences to Improve Transformation Efficiency. Current Genetics, vol. 21, No. 3, pp. 207-213.
Roller et al. Biotechnology in the Production and Modification of Biopolymers for Foods. Critical Reviews in Biotechnology, 1992, vol. 12, No. 3, pp. 261-277.
Sakamoto et al. Molecular characterization of a *Penicillium chrysogenum* exo-1,5-a-L-arbinanase that is structurally distinct from other arabinan-degrading enzymes. FEBS Lett. 2004, vol. 506, pp. 199-204.
Saloheimo et al. cDNA cloning of a *Trichoderma reesei* cellulose and demonstration of endoglucanase activity by expression in yeast. Eur. J. Biochem, 1997, vol. 249, p. 584-591.
Seffernick, et al. 2001. Melamine deaminase and atrazine chloroydrolase: 98 percent identical but functionally different. Journal of Bacteriology, vol. 183, No. 8, pp. 2405-2410.
Sheehan et al. Enzymes, energy and the Environment: A Strategic Perspective on the U.S. Department of Energy's Research and Development Activities for Bioethanol. Biotechnology Progress, 1999, vol. 15, pp. 817-827.
Sheppard, P.O. et al. 1995. The Use of Conserved Cellulase Family-Specific Sequences to Clone Cellulase Homologue cDNAs from Fusarium Oxysporum, XP002154884, Abstract.
Shih et al. A comparison of the pectate lyase genes, pel-1 and pel-2, of *Colletotrichum gloeosporioides* f.sp. malvae and the relationship between their expression in culture and during necrotrophic infection. Gene, 2000, vol. 243, pp. 139-150.
Sorensen et al. Efficiencies of Designed Enzyme Combinations in Releasing Arabinose and Xylose from Wheat Arabinoxylan in an Industrial Ethanol Fermentation Residue. Enzyme Microb. Technol., 2005, vol. 36, pp. 773-784.
Sørensen et al. A Novel GH43 alpha-L-arabinofuranosidase from Humicola insolens: Mode of Action and Synergy with GH51 alpha-L-arabinofuranosidases on wheat arabinoxylan. Appl. Microbiol. Biotechnol. 2006, vol. 73, pp. 850-861.
Sørensen et al. Enzymatic Hydrolysis of Wheat Arabinoxylan by a Recombinant "Minimal" Enzyme Cocktail Containing B-Xylosidase and Novel Endo-1,4-B-Xylanase and a-L-Arabinofuranosidase Activities. Biotechnol. Progr., 2007, vol. 23, pp. 100-107.
Takami et al. Complete genome sequence of the alkaliphilic bacterium *Bacillus halodurans* and genomic sequence comparison with *Bacillus subtilis*. Nucleic Acid Res, 2000, vol. 28, pp. 4317-4331.
Uzcategui et al. The 1,4-b-d-glucan glucanohydrolases from *Phanerochaete chrysosporium*. Re-assessment of their significance in cellulose degradation mechanisms. Journal of Biotechnology, 1991, vol. 21, pp. 143-160.
Van De Rhee et al., "Transformation of the cultivated mushroom, *Agaricus bisporus*, to hygromycin B resistance," Mol. Gen. Genet., vol. 250, pp. 252-258 (1996).
Van Den Broek L.A.M. et al. Cloning and Characterization of Arabinoxylan Arabinofuranosidase-D3 (AXHd3) from Bifidobacterium adolescentis DSM 20083. Appl. Microbiol. Biotechnol, 2005, vol. 67, pp. 641-647.
Van Laere, D.M.J. et al. A New Arabinofuranohydrolase from Bifidobacterium adolescentis Able to Remove Arabinosyl Residues from Double-Substitutes Xylose Units in Arabinoxylan. Appl. Microbiol. Biotechnol, 1997, vol. 47, pp. 231-235.
Van Oorschot, A Revision of *Chrysosporium* and Allied Genera. Studies in Mycology, 1980, No. 20, pp. 1-3, 8-9 and 32-35.
Van Zeijl et al., "An improved colony-PCR method for filamentous fungi for amplification of PCR-fragments of several kilobases," Journal of Biotechnology, vol. 59, pp. 221-224 (1998).
Verdoes et al., "Characterization of an efficient gene cloning strategy for *Aspergillus niger* based on an autonomously replicating plasmid: cloning of the nicB gene of *A. niger*," Gene, vol. 146, pp. 159-165 (1994).
Viikari et al. Use of Cellulases in Pulp and Paper Applications. In Carbohydrates from *Trichoderma reesei* and Other Microorganisms. Structure, Biochemistry, Genetics, and Applications. Claessens, M. et al. eds. The Royal Society of Chemistry, 1998, pp. 245-254.
Xu et al. Humicola insolens cellobiose dehydrogenase: cloning, redox chemistry, and "logic gate"-like dual functionality. Enzyme Microb. Technol., 2001, vol. 28, p. 744-753.
Yano et al. Cloning and Expression of an a-1,3-Glucanase Gene from *Bacillus* Circulans KA-304: The Enzyme Participates in Protoplast Formation of Schizophyllum Commune. Biosci Biotechnol. Biochem., 2006, vol. 70, pp. 1754-1763.

* cited by examiner

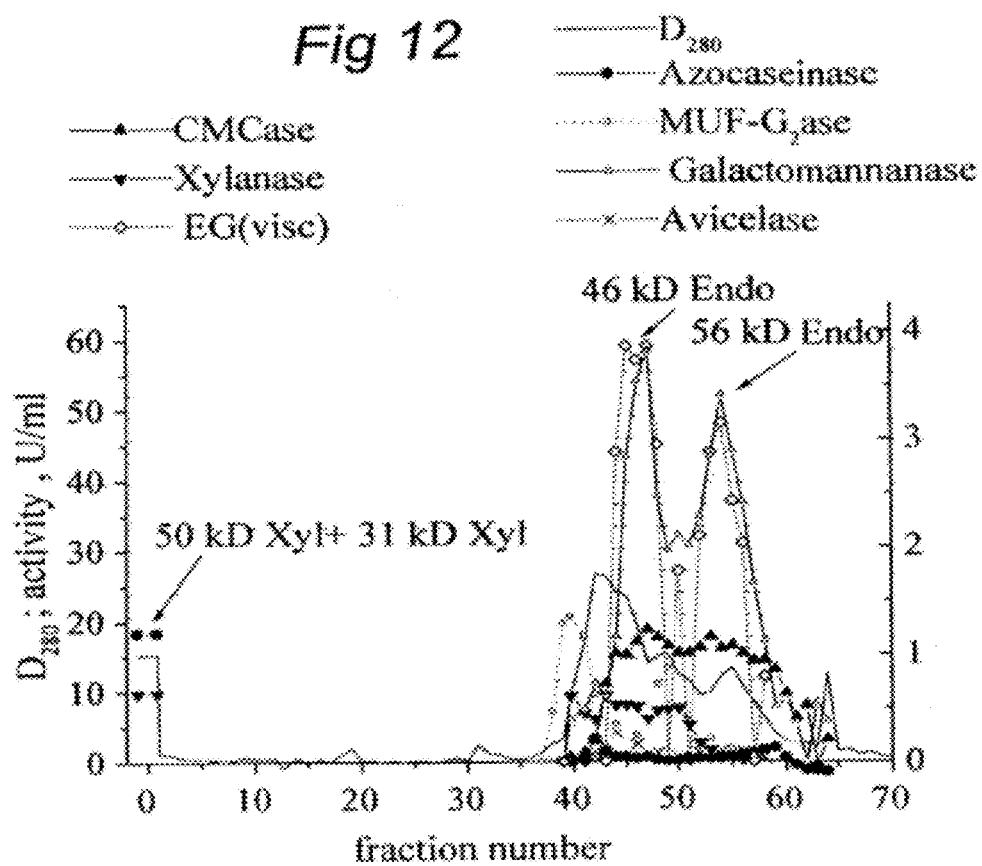

Fig 13a
45kD endo (pI 6.0)
Fig 13b
55 kD endo (pI 4.9)
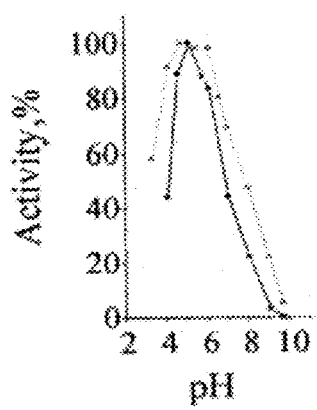
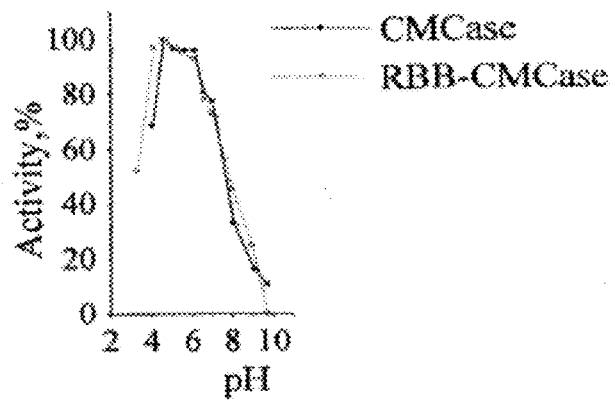
Fig 13c
30kD Xyl (pI 9.1)
Fig 13d
51kD Xyl (pI 8.7)
Fig 13e
60 kD Xyl (pI 4.7)
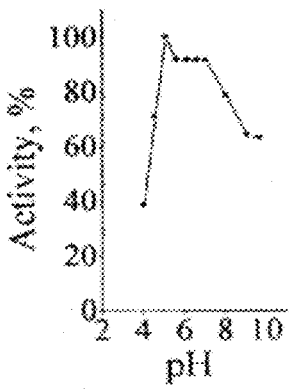
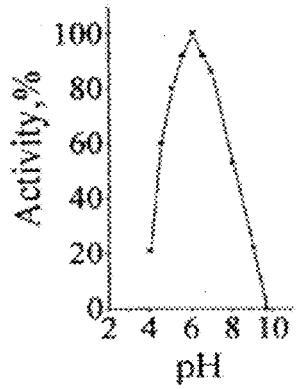
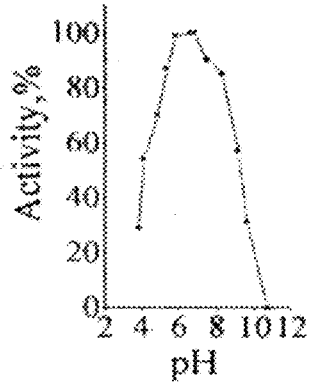

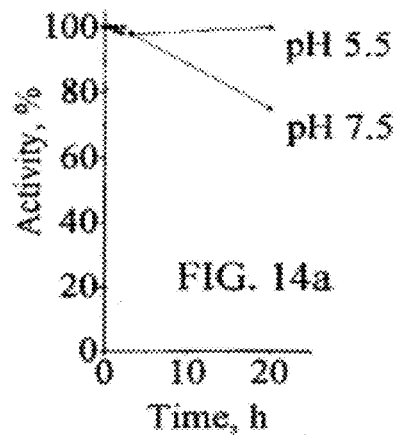
Fig 14a
45 kD Endo (pI 6.0)
FIG. 14a
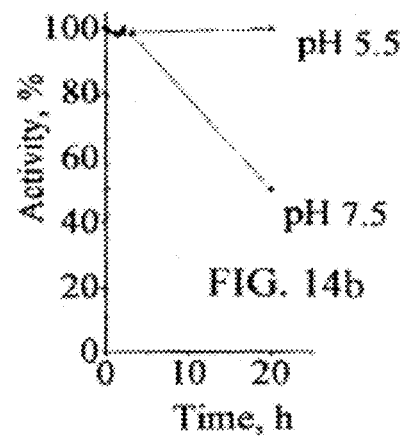
Fig 14b
55 kD Endo (pI 4.9)
FIG. 14b
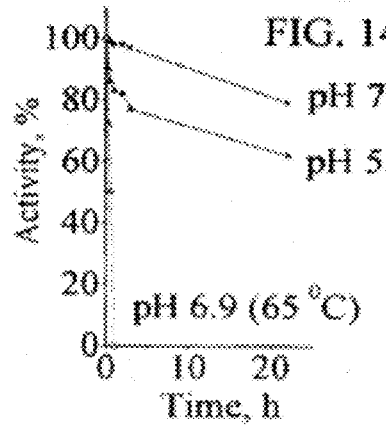
Fig 14c
30 kD Xyl (pI 9.1)
FIG. 14c
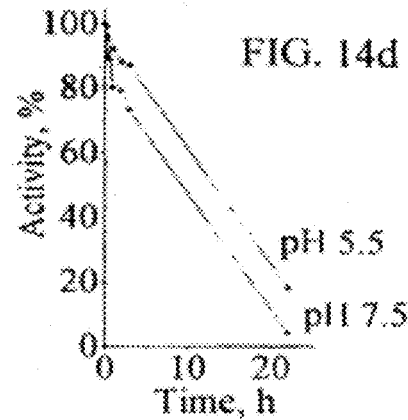
Fig 14d
51 kD Xyl (pI 8.7)
FIG. 14d

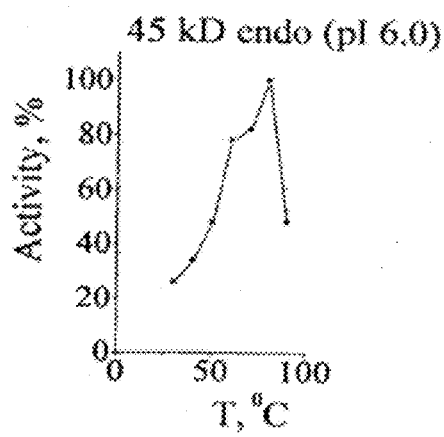
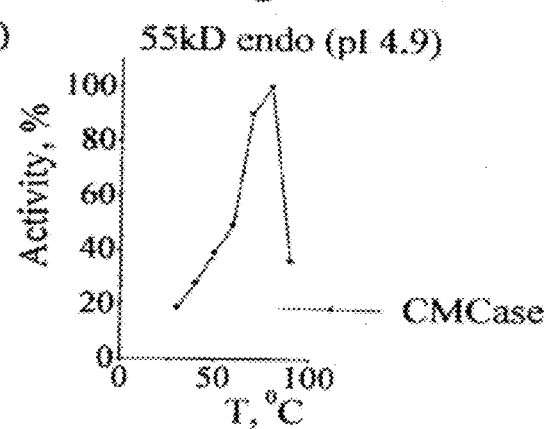
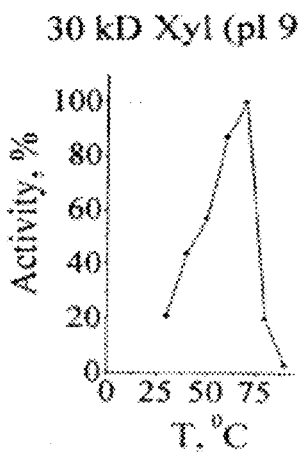
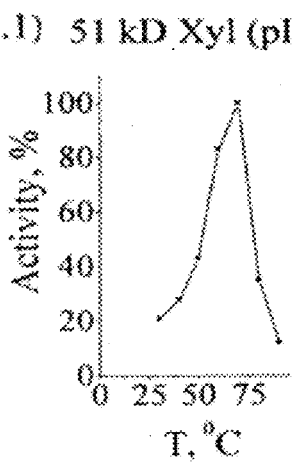
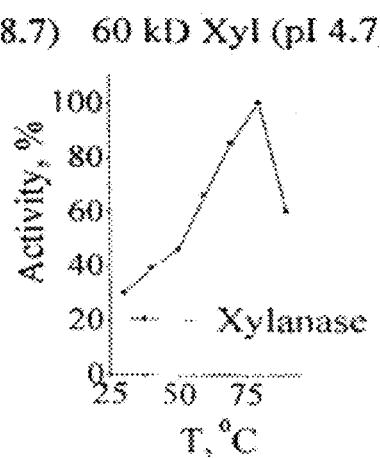

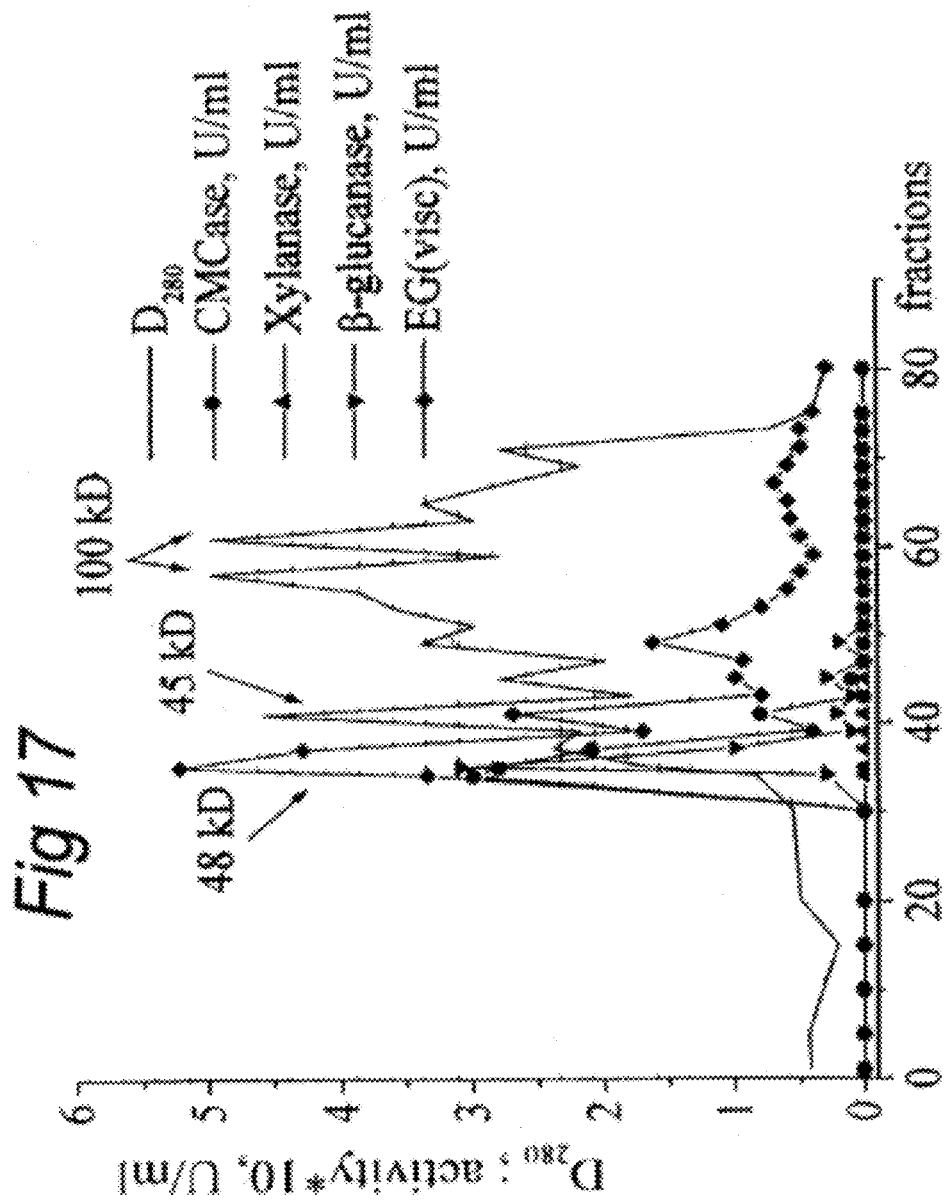

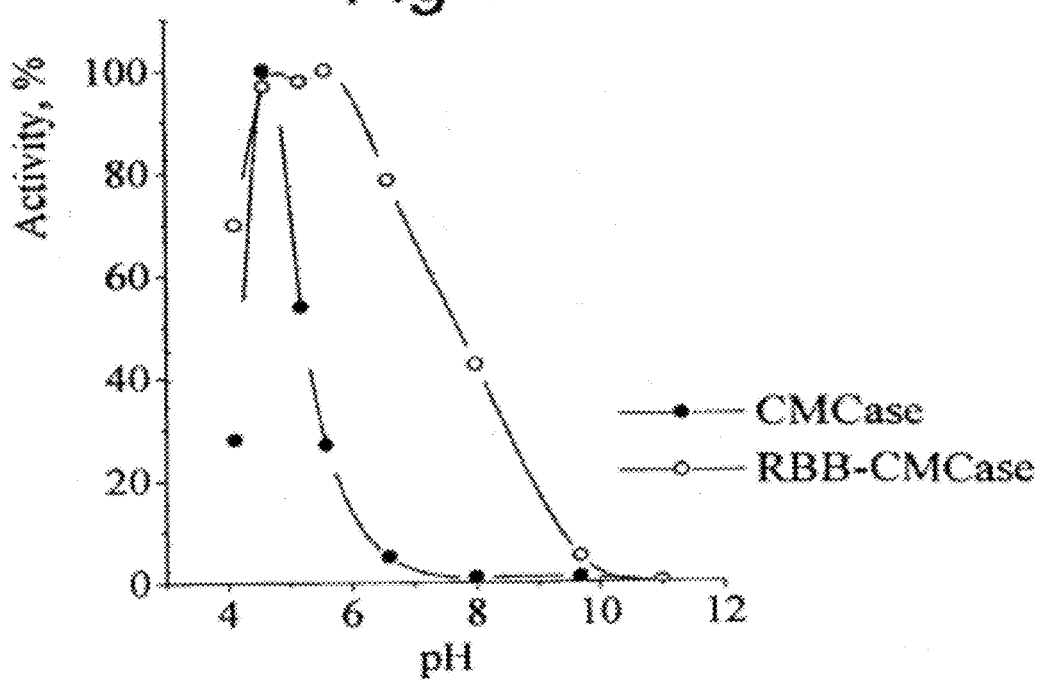

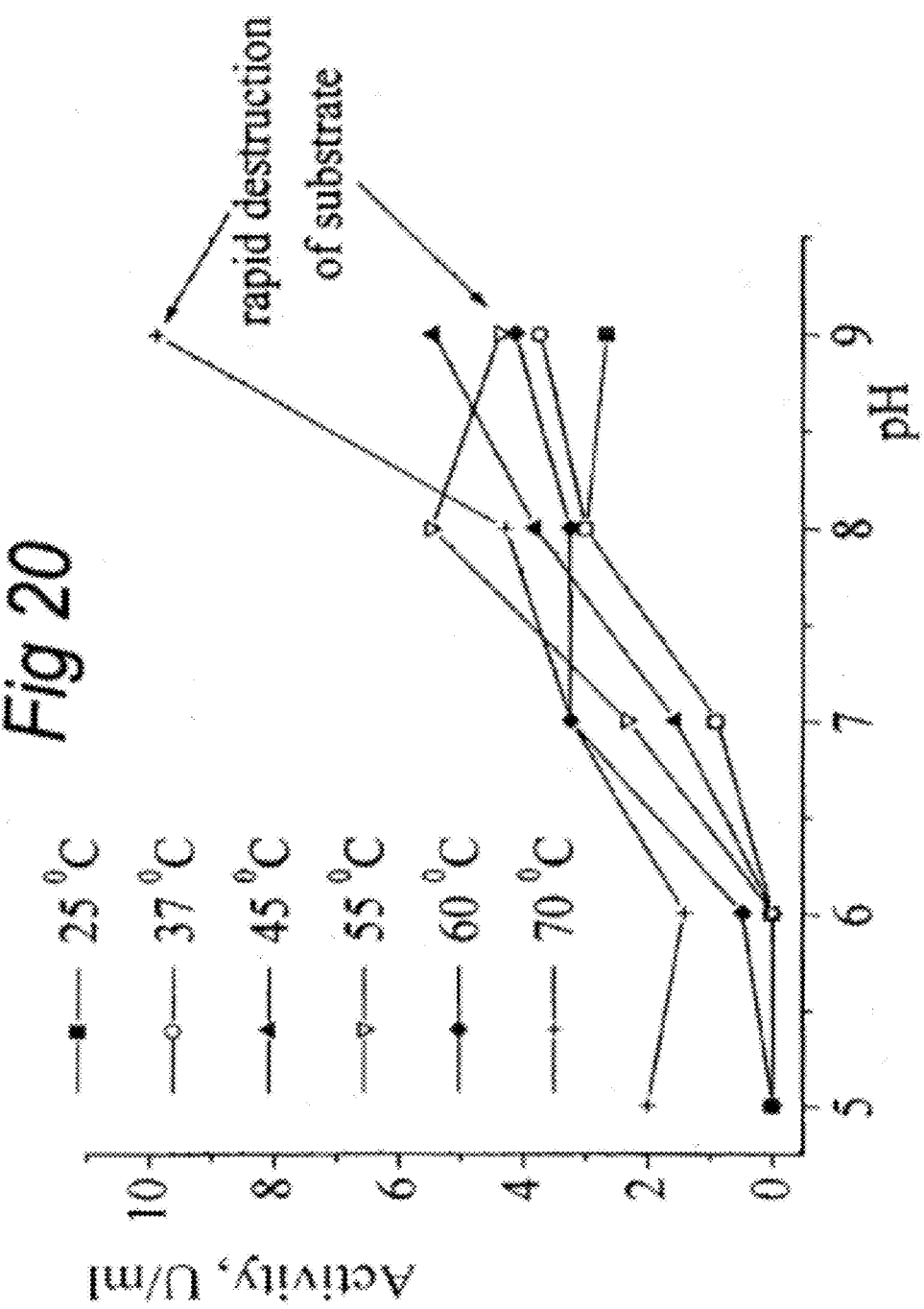

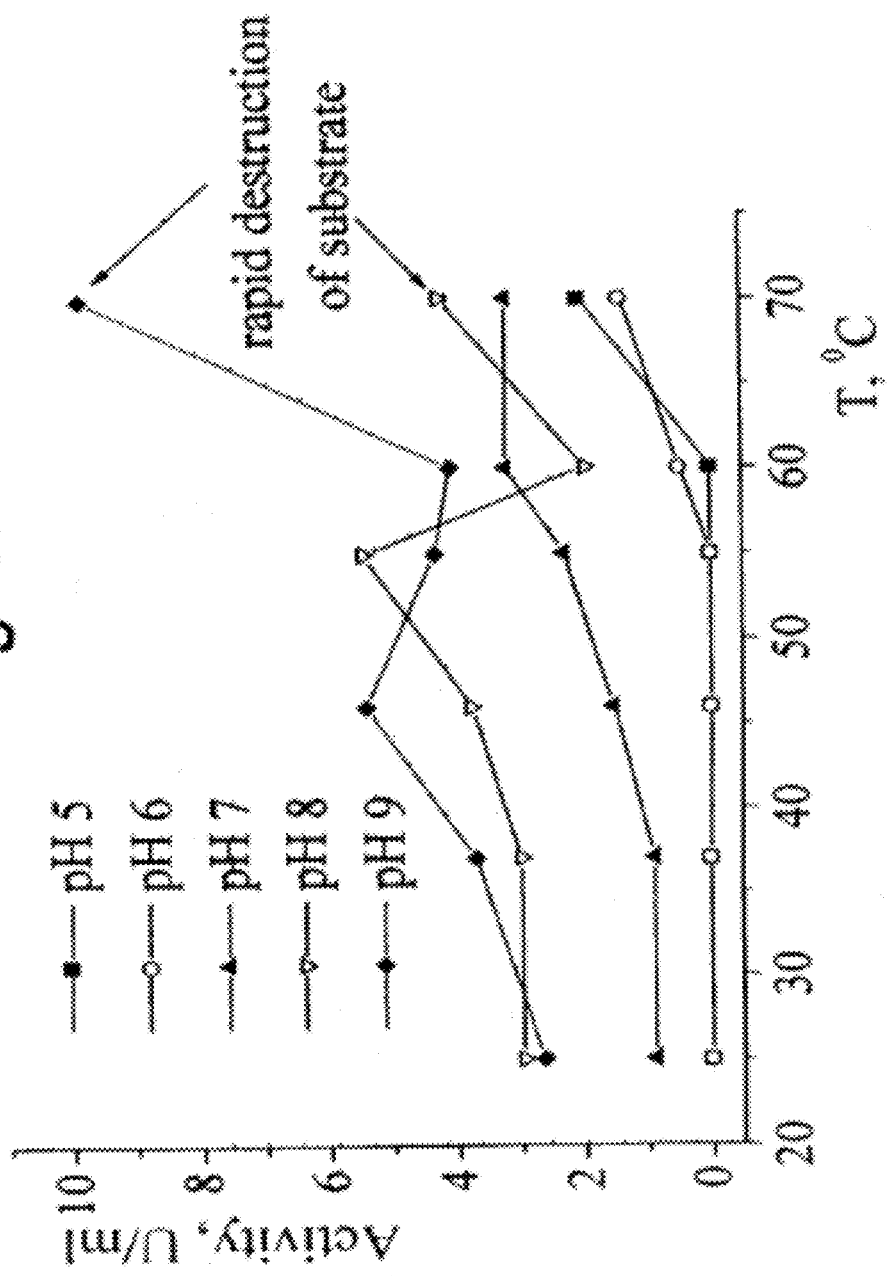

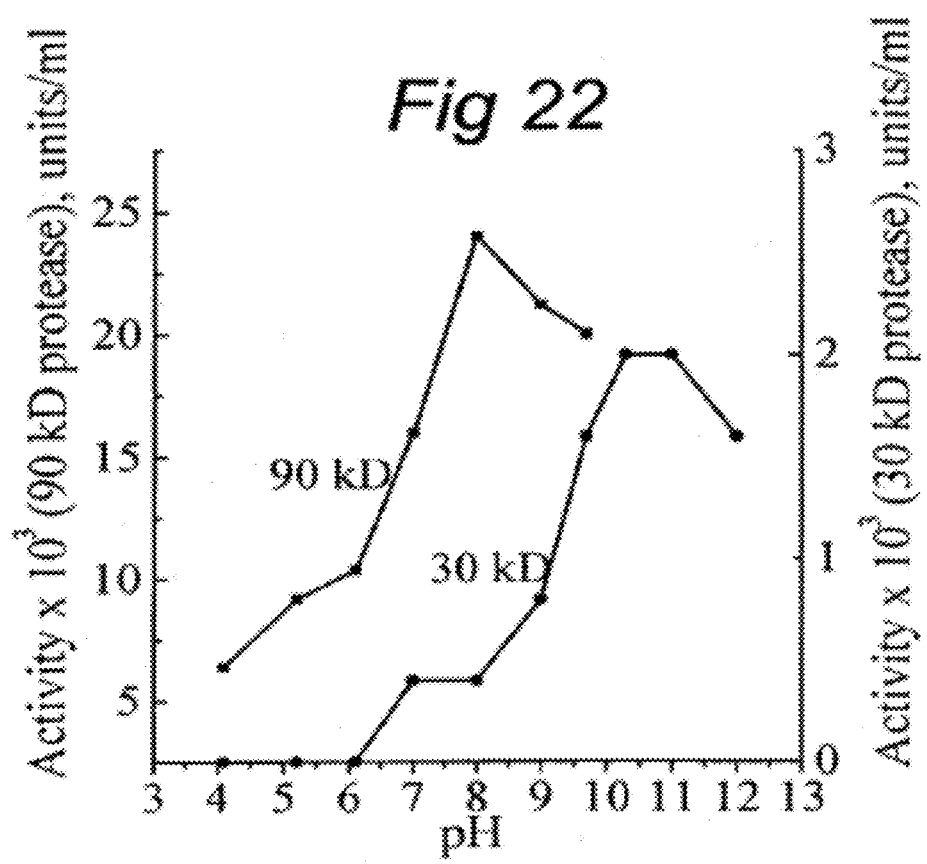

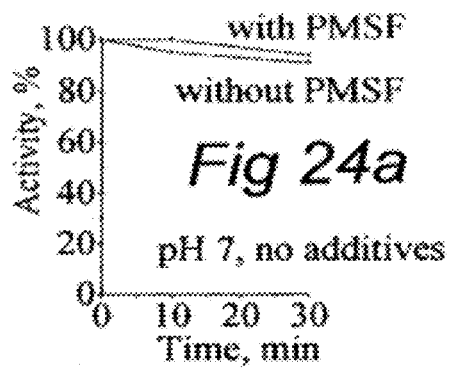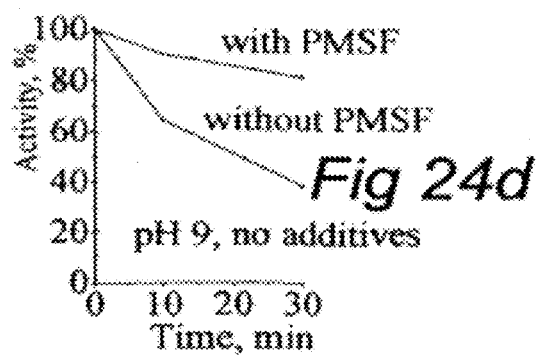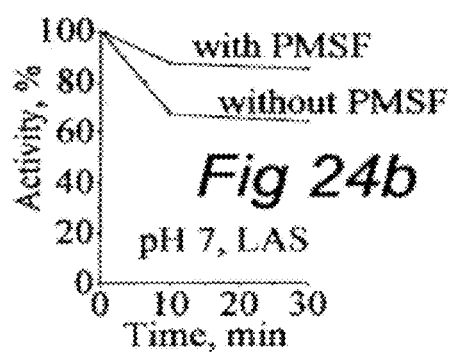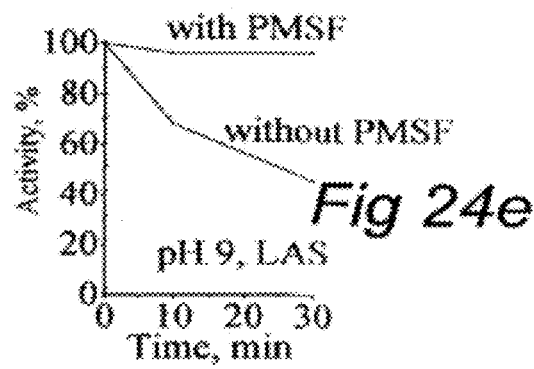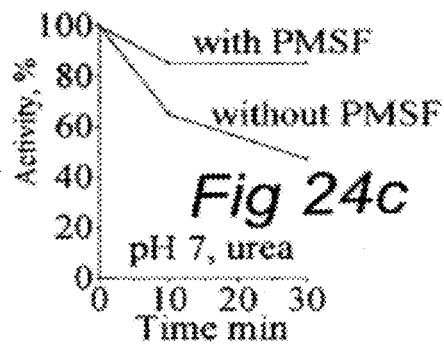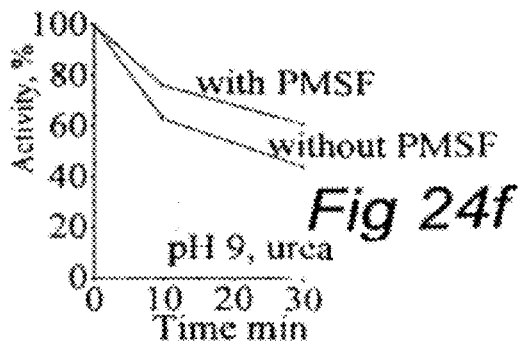

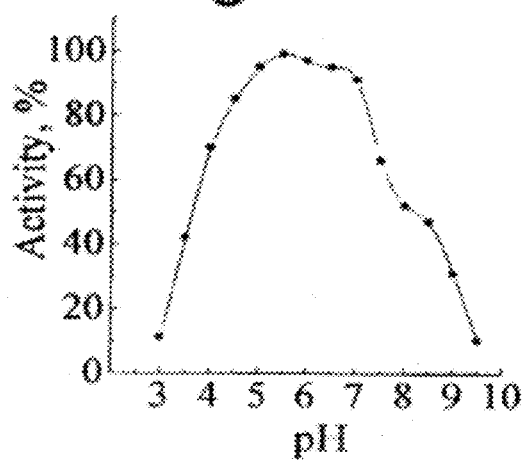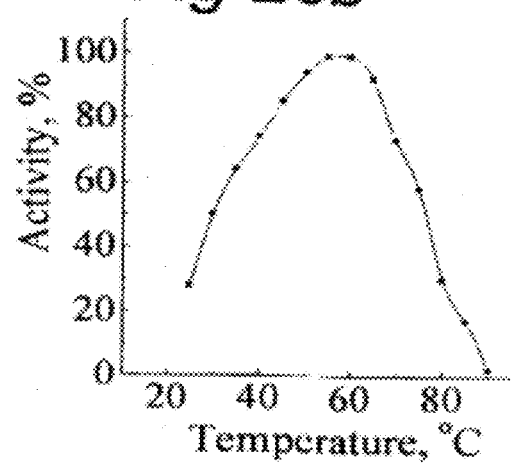

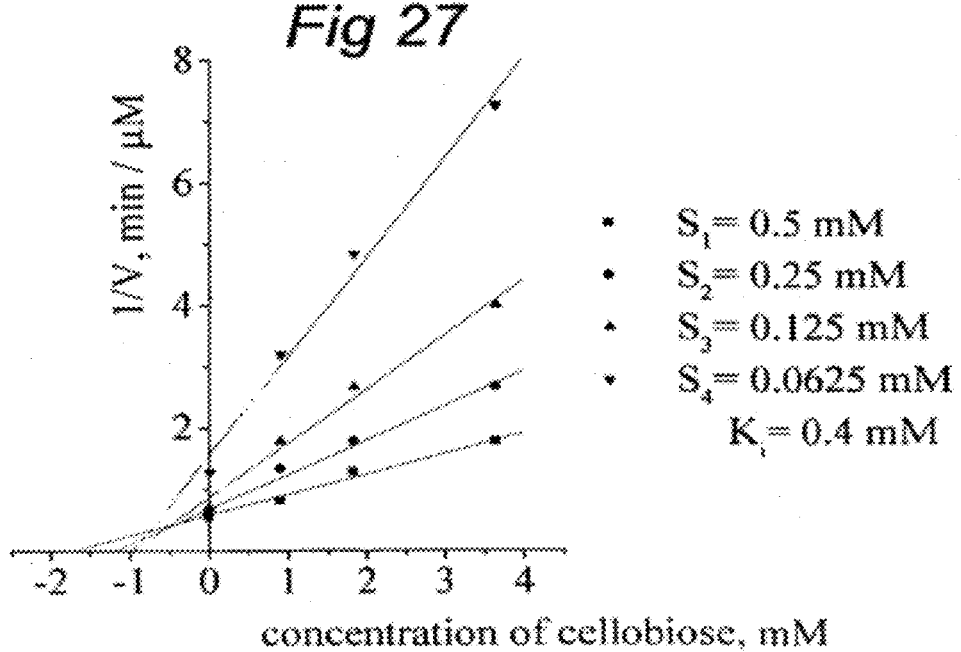

TRANSFORMATION SYSTEM IN THE FIELD OF FILAMENTOUS FUNGAL HOSTS

REFERENCE TO PRIOR APPLICATIONS

This application is a continuation of U.S. application Ser. No. 10/394,568, filed Mar. 21, 2003 now U.S. Pat. No. 7,399,627, which is a continuation of U.S. application Ser. No. 09/548,938, filed Apr. 13, 2000, now U.S. Pat. No. 6,573,086, which is a continuation-in-part of international application PCT/NL99/00618, filed Oct. 6, 1999, which is a continuation-in-part of international application PCT/EP98/06496, filed Oct. 6, 1998, all of which are incorporated herein by reference.

BACKGROUND OF THE INVENTION

A number of hosts for gene expression and methods of transformation have been disclosed in the prior art. Bacteria are often mentioned e.g. *Escherichia coli*. *E. coli* is however a micro-organism incapable of secretion of a number of proteins or polypeptides and as such is undesirable as host cell for production of protein or polypeptide at the industrial level. An additional disadvantage for *E. coli*, which is valid also for bacteria in general, is that prokaryotes cannot provide additional modifications required for numerous eukaryotic proteins or polypeptides to be produced in an active form. Glycosylation of proteins and proper folding of proteins are examples of processing required to ensure an active protein or polypeptide is produced. To ensure such processing one can sometimes use mammalian cells; however, the disadvantage of such cells is that they are often difficult to maintain and require expensive media. Such transformation systems are therefore not practical for production of proteins or polypeptides at the industrial level. They may be cost efficient for highly priced pharmaceutical compounds requiring relatively low amounts, but certainly not for industrial enzymes.

A number of fungal expression systems have been developed e.g. *Aspergillus niger, Aspergillus awamori, Aspergillus nidulans, Trichoderma reesei*. A number of others have been suggested but for various reasons have not found wide-spread acceptance or use. In general terms the ideal host must fulfill a large number of criteria:

- The ideal host must be readily fermented using inexpensive medium.
- The ideal host should use the medium efficiently.
- The ideal host must produce the polypeptide or protein in high yield, i.e. must exhibit high protein to biomass ratio.
- The ideal host should be capable of efficient secretion of the protein or polypeptide.
- The ideal host must enable ease of isolation and purification of the desired protein or polypeptide.
- The ideal host must process the desired protein or polypeptide such that it is produced in an active form not requiring additional activation or modification steps.
- The ideal host should be readily transformed.
- The ideal host should allow a wide range of expression regulatory elements to be used thus ensuring ease of application and versatility.
- The ideal host should allow use of easily selectable markers that are cheap to use.
- The ideal host should produce stable transformants.
- The ideal host should allow cultivation under conditions not detrimental to the expressed protein or polypeptide e.g. low viscosity, low shear.

Fungal systems that have not yet found widespread use are described e.g. in U.S. Pat. No. 5,578,463 by Berka et al suggesting *Neurospora, Podospora, Endothia, Mucor, Cochoibolus* and *Pyricularia* together with *Aspergillus* and *Trichoderma*. However only illustrations of transformation and expression are provided for *Aspergillus* and *Trichoderma* and no details are provided for any of the other suggested hosts.

WO 96/02563 and U.S. Pat. Nos. 5,602,004, 5,604,129 and 5,695,985 to Novo Nordisk describe the drawbacks of *Aspergillus* and *Trichoderma* systems and suggests cultivation conditions for other fungi may be more suited to large scale protein production. The only examples provided for any transformed cultures are those of *Myceliophthora thermophila, Acremonium alabamense, Thielavia terrestris* and *Sporotrichum cellulophilum* strains. The *Sporotrichum* strain is reported to lyse and produce green pigment under fermentation conditions not leading to such results for the other strains. A non-sporulating mutant of *Thielavia terrestris* is described as being the organism of choice by virtue of its morphology. However it is also stated that the protoplasting efficiency of *Thielavia* and *Acremonium* (whereby the *Acremonium* strain used was the imperfect state of the *Thielavia* strain used) is low and that hygromycin was not useful as a selection marker. A large number of others are suggested as being potentially useful by virtue of their morphology but no transformation thereof is described. The suggested strains are *Corynascus, Thermoascus, Chaetomium, Ctenomyces, Scytalidium* and *Talaromyces*. The transformed hosts are mentioned as only producing low levels of the introduced *Humicola* xylanase with *Thielavia* producing the lowest amount; however, the information is ambiguous and could actually infer *Thielavia* was the best embodiment. The nomenclature of this reference is based on the ATCC names of Industrial Fungi of 1994. Thus it is apparent no high degree of heterologous expression was achieved and in fact no positive correlation could be derived between the postulated morphology and the degree of expression. If any correlation could be made, it was more likely to be negative. According to the 1996 ATCC fungal classification *Sporotrichum thermophilum* ATCC 20493 is a *Myceliophthora thermophila* strain. Currently the strain is still identified as *Myceliophthora thermophila*. The unpredicatability of the art is apparent from these recent disclosures.

Also Allison et al (*Curr. Genetics* 21:225-229, 1992) described transformation of *Humicola grisea* var. *thermoidea* using the lithium acetate method and a *Humicola* enzyme-encoding sequence, but no report of expression of heterologous protein from such a strain has been provided.

In 1997 a patent issued to Hawaii Biotechnology Group for transformed *Neurospora* for expression of mammalian peptide such as chymosin. The transformation of auxotrophic *Neurospora crassa* occurred with spheroplasts. Endogenous transcriptional regulatory regions were introduced and cotransformation was carried out. Nothing is mentioned concerning other hosts and other transformation protocols. Nothing is apparent from the disclosure concerning the degree of expression. It is doubtful whether the degree of expression is high, as immunotechniques (which are useful for detecting small amounts of protein) are the only techniques used to illustrate the presence of the protein. No actual isolation of the protein is disclosed.

WO 97/26330 of Novo Nordisk suggests a method of obtaining mutants of filamentous fungal parent cells having an improved property for production of heterologous polypeptide. The method comprises first finding a specific altered morphology followed by assessing whether a transformant produces more heterologous polypeptide than the parent. The method is illustrated only for strains of *Fusarium* A3/5 and *Aspergillus oryzae*. The method is suggested to be applicable for *Aspergillus, Trichoderma, Thielavia, Fusarium, Neurospora, Acremonium, Tolyplocadium, Humicola, Scytalidium, Myceliophthora* or *Mucor*. As stated above the unpredictability in the art and also the unpredictability of the method of the cited application do not provide a generally applicable teaching with a reasonable expectation of success.

BRIEF SUMMARY OF THE INVENTION

The subject invention pertains to a novel transformation system in the field of filamentous fungal hosts for expressing and secreting heterologous proteins or polypeptides. The invention also covers a process for producing large amounts of polypeptide in an economical manner. The system comprises a transformed or transfected fungal strain of the genus *Chrysosporium*, more particularly of *Chrysosporium lucknowense* and mutants or derivatives thereof. It also covers transformants containing *Chrysosporium* coding sequences. Novel mutant *Chrysosporium* strains are disclosed as are novel enzymes derived therefrom. The subject invention further relates to novel enzymes derived from filamentous fungi, especially from strains of the genus *Chrysosporium*, and to coding sequences and expression-regulating sequences for these enzymes.

BRIEF DESCRIPTION OF THE DRAWINGS

FIG. 12: Ion exchange chromatography on Macro Prep Q of non-bound fraction after DEAE-Toyopearl of F-60-31 CF sample.
FIG. 13: pH dependencies of activity of enzymes from non-bound fractions of F-60-31 CF sample.
FIG. 14: Stability of enzymes from non-bound fraction of F-60-31 CF sample at pH 5.5 and 7.5 (60° C.).
FIG. 16: Temperature dependencies of enzymes from non-bound fraction of F-60-31 sample.
FIG. 17: Ion exchange chromatography on Macro Prep Q of bound fractions 50-53 after DEAE-Toyopearl of F-60-8 sample.
FIG. 19: pH dependencies of activity of 48 kD CBH (pI 4.4) from bound fractions of F-60-8, UF-conc.
FIG. 20: Temperature dependencies of activity towards p-nitrophenyl butyrate of F-60-8 UF-conc.
FIG. 21: pH dependencies of activity towards p-nitrophenyl butyrate of F-60-8 UF-conc.
FIG. 22: pH courses of activities of 30 kD (pI 8.9) and 90 kD (pI 4.2) proteases toward C1 proteins (50° C., 30 min. incubation).
FIG. 24: Effect of 90 kD (pI 4.2) "neutral" protease on CMCase activity of the proteins in the bound fraction #44-45 (DEAE-Toyopearl) of F 60-8 UV-conc sample at 50° C.

FIG. 25: Complete hydrolysis of polygalacturonic acid by 65 kD polygalacturonase (pI 4.4): 50° C., pH 4.5; concentration of PGA=5 g/l, concentration of protein=0.1 g/l.

FIG. 26: pH- and temperature dependencies of polygalacturonase activity of F-60-43 UF-conc.

FIG. 27: Inhibition of activity toward MUF-cellobioside by cellobiose for 55 kD CBH (pI 4.4): pH 4.5, 40 C.

FIG. 28: Synergistic effect between 25 kD Endo (pI 4.1) and 55 kD CBH (pI 4.4) toward avicel (40 C, pH 5, 25 min).

FIG. 29: Complete hydrolysis of CMC (a and c) and avicel (b and d) by the enzymes isolated from bound fractions of F-60-8 UF-conc. sample (50° C., pH 5): concentration of CMC and avicel=5 g/l, concentration of 25 kD Endo=0.01 g/l, concentration of 43 kD Endo=0.02 g/l; (a and b) 25 kD Endo (pI 4.1), (c and d) 43 kD Endo (pI 4.2).

FIG. 30: Complete hydrolysis of CMC (a and b) and avicel (c and d) by 55 kD CBH (pI 4.4) without (a and c) and with (b and d) glucono-δ-lactone (50° C., pH 4.5): concentration of CMC and avicel=5 g/l, concentration of protein=0.1 g/l, concentration of glucono-δ-lactone=5 g/l.

FIG. 31: pH-Dependence of CMCase and RBB-CMCase activities of the enzymes isolated from F-60-8 UF-conc. sample: (a) 25 kD Endo (pI 4.1), (b) 43 kD Endo (pI 4.2).

FIG. 32: pH-Dependencies of CMCase and RBB-CMCase activities of 55 kD CBH (pI 4.4).

FIG. 33: Temperature dependencies of CMCase activity (pH 4.5) of the enzymes isolated from bound fractions of F-60-8 UF-conc. sample: (a) 55 kD CBH (pI 4.4), (b) 25 kD Endo (pI 4.1), (c) 43 kD Endo (pI 4.2).

FIG. 34: pH-stability (50° C.) of the enzymes isolated from bound fractions of F-60-8 UF-conc. sample: (a) 55 kD CBH (pI 4.4), (b) 25 kD Endo (pI 4.1), (c) 43 kD Endo (pI 4.2).

FIG. 35: Adsorption of the enzymes isolated from bound fractions of F-60-8 UF-conc. sample.

FIG. 36: Purification scheme of F-60-8 (UF-conc) and F-60-31 CF Samples for C1 Protein Isolation.

DETAILED DESCRIPTION OF THE INVENTION

We now describe an alternative fungal expression system with the simplicity of use of the above-mentioned *Aspergilli* and *Trichoderma* fulfilling the above requirements. The new system has not been taught or suggested in the prior art. The new system according to the invention provides the additional advantages that transformation rates are higher than those for the frequently used *Trichoderma reesei* system. In addition the culture conditions offer the additional bonus of being advantageous for the expressed polypeptide.

We further describe a number of industrially interesting enzymes derived from the novel expressing system, together with full sequence information. We also describe novel promoter systems derived from *Chrysosporium* strains and useful for expressing homologous and heterologous genes.

The present invention is thus also concerned with glycosyl hydrolases of the families 7 (e.g. cellobiohydrolases), 10 (e.g. xylanases) and 12 (e.g. endoglucanases), and glyceraldehyde phosphate dehydrogenases, as identified by their amino acid sequence, as well as peptides derived from these enzymatic proteins, and with nucleic acid sequences encoding these peptides and proteins, as well as, in particular, with regulating sequences related to these genes.

Figure 1:
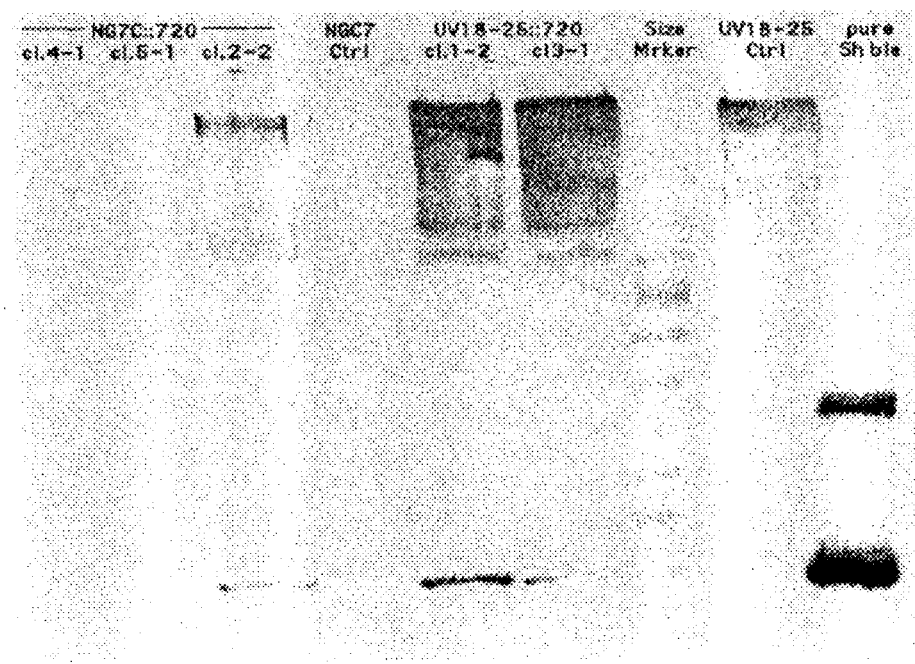
FIG. 1 is a Western blot as described in the Examples

In particular, the present invention pertains to isolated or recombinant enzymic proteins or active parts thereof of the four classes referred to above, including mutants thereof having at least a certain degree of sequence identity as specified in the further disclosure and in the claims, as well as nucleic acid sequences encoding these proteins or parts thereof, and/or nucelic acid sequences regulating their expression. These enzymes are especially: (1) a glycosyl hydrolase of family 7 (cellobiohydrolase, CBH1) having at least 75%, preferably at least 80% or even at least 85% amino acid identity with the sequence of SEQ ID No 1; (2) a glycosyl hydrolase of family 10 (endoxylanase XYLF or XYL1) having at least 70%, preferably at least 75% or even at least 80% amino acid identity with the sequence of SEQ ID No 2; (3) a glycosyl hydrolase family of 12 (endoglucanase, EG3) having at least 65%, preferably at least 70% or even at least 80% amino acid identity with the sequence of SEQ ID No. 3; and (4) a glyceraldehyde phosphate dehydrogenase (GPD1) having at least 86%, preferably at least 90% or even at least 93% amino acid identity with the sequence of SEQ ID No 4. Polypeptides and nucleic acid sequences encoding these polypeptides, having at least 20, preferably at least 30 contiguous amino acids of SEQ ID No's 1-4 are also a preferred part of the invention.

The recombinant enzymes may comprise essentially the complete protein, or a truncated protein having at least part of the enzymatic activity. Such truncated part may be the catalytic domain, or at least about 75% of the amino acids thereof. By way of example, the catalytic domain of the CBH1 according to the invention comprises the aminoacids 20-495 of the aminoacid sequence of SEQ ID No. 1, and the catalytic domain of the XYL1 according to the invention comprises the aminoacids 54-384 of the aminoacid sequence of SEQ ID No. 2. The catalytic domain may or may not be combined with a signal sequence originating from another protein and/or with a carbohydrate-binding domain from another enzymic protein. Alternatively, the cellulose-binding domain of the enzymes of the invention (CBH1 and XYL1) may be fused to catalytic domains of other enzymic proteins.

The nucleic acid sequences according to of the invention may be complete protein-encoding regions or oligonucleotides or, preferentially, expression-regulating sequences. Oligonucleotides may be used also as probes for identifying genes corresponding to, but not identical to the genes of SEQ ID No.'s 1-4; these genes, when fulfilling the percentage identity criteria defined herein, as well as encoding and non-encoding parts thereof and their expression products are also part of the invention.

The invention also pertains to expression systems (cassettes) comprising either an expression-regulating region (including a promoter) of any of the four protein classes fused to a gene encoding another protein of interest, or an encoding region of any of these proteins fused to another expression regulating region, or both the expression-regulating region and the protein-encoding region of these novel proteins. The expression-regulating region comprises at least 60%, preferably at least 70%, more preferably at least 75% or even 80% of the 5'-non-coding region of SEQ ID No.'s 1-4, and/or at least 20, especially at least 40 contiguous nucleotides from these 5' non-coding regions. Terminating sequences similarly derived from the 3' non-coding regions of the genes of the invention are also useful in expressing cassettes, whether combined with homologous or heterologous genes.

These expression systems may be contained in a *Chrysosporium* host, such as a *Chrysosporium lucknowense* host, or in another non-fungal or, preferably, fungal host. Examples of other fungal hosts are other *Chrysosporium* species or strains, *Fusarium* species, *Aspergillus* species etc. Such host may be advantageously a host that does not itself, intrinsically or as a result of the culture conditions, produce a protein corresponding to the protein of interest, so as to simplify the recovery of the protein of interest.

Where reference is made in this specification and in the appending claims to "polypeptides" or "peptides" or "polypeptides of interest" or "peptides of interest" as the products of the expression system of the invention, this term also comprise proteins, i.e. polypeptides having a particular function and/or secondary and/or tertiary structure. Where reference is made to percentage amino acid identity, such identity relates to e complete protein or a to a specific part defined by initial and final amino acid number, as determined by the conventionally used BLAST algorithm.

In the production method of the invention, the pH of the culture medium can be neutral or alkaline thus no longer subjecting the produced protein or polypeptide to aggressive and potentially inactivating acid pH. It is also possible to culture at acid pH such as pH 4 for cases where the protein or polypeptide is better suited to an acidic environment. Suitably culture can occur at a pH between 4.0-10.0. A preference however exists for neutral to alkaline pH as the host strain exhibits better growth at such pH, e.g. between 6 and 9. Growth at alkaline pH which can be from pH 8 up and can even be as high as 10 is also a good alternative for some cases. Also the cultivation temperature of such host strains is advantageous to the stability of some types of produced polypeptide. The cultivation temperature is suitably at a temperature of 25-43° C. A temperature in the range from 40° C. down to 23° C. or 30° C. is also advantageously applied. Clearly such conditions are of particular interest for production of mammalian polypeptides. The selected temperature will depend on cost effectiveness of the cultivation and sensitivity of the polypeptide or cultivation strain. The conditions will be determined by the skilled person without undue burden on a case-by-case basis, as is common in the art.

It has also been ascertained that the biomass and viscosity relations to the amount of protein produced is exceedingly favourable for the host according to the invention. Comparisons have been carried out with *Trichoderma longibrachiatum* (formerly also known as *Trichoderma reesei*) and with *Aspergillus niger*. *Trichoderma longibrachiatum* gave 2.5-5 g/l biomass, *Aspergillus niger* gave 5-10 g/l biomass and the host according to the invention gave 0.5-1 g/l biomass under their respective optimised conditions. This thus offers 5-10 fold improvement over the commercially used strains. These commercial strains are strains which themselves are considered in the art to be high producers of proteins and they are successfully used for commercial protein production. They have been cultured under their optimal conditions developed and run viably in large-scale commercial fermenters. The same strains were used to illustrate enormous improvement in viscosity values for cultures of the host according to the invention. At the end of the fermentation process *Trichoderma longibrachiatum* gave a value of 200-600 cP (Centipoise), *Aspergillus niger* gave a value of 1500-2000 cP and the host according to the invention gave a value below 10 cP. This thus provides at least 20-200 fold improvement for viscosity values over the commercially used strains. A quite surprising further aspect was that the protein levels determined for the host cells according to the invention were much higher than for the commercial *Aspergilli* and *Trichoderma reesei* strains, even with the above mentioned surprisingly low biomass and viscosity levels. In summary an easy to use versatile improved transformation system and expression system with improved culturing conditions has hereby been introduced. The strains according to the invention produce surprisingly higher protein levels under these improved conditions and in addition they do such in a shorter fermenter time.

The subject invention is directed at mutant *Chrysosporium* strains comprising a nucleic acid sequence encoding a heterologous protein or polypeptide, said nucleic acid sequence being operably linked to an expression regulating region and optionally a secretion signal encoding sequence and/or a carrier protein encoding sequence. Preferably a recombinant strain according to the invention will secrete the polypeptide of interest. This will avoid the necessity of disrupting the cell in order to isolate the polypeptide of interest and also minimise the risk of degradation of the expressed product by other components of the host cell.

*Chrysosporium* can be defined by morphology consistent with that disclosed in Barnett and Hunter 1972, Illustrated Genera of Imperfect Fungi, 3rd Edition of Burgess Publishing Company. Other sources providing details concerning classification of fungi of the genus *Chrysosporium* are known e.g. Sutton Classification (Van Oorschot, C. A. N. (1980) "A revision of *Chrysosporium* and allied genera" in Studies in Mycology No. 20 of the CBS in Baarn The Netherlands p1-36). CBS is one of the depository institutes of the Budapest Treaty. According to these teachings the genus *Chrysosporium* falls within the family Moniliaceae which belongs to the order Hyphomycetales. The criteria that can be used are the following:

1. Signs of Hphomycetales order:

Conidia are produced directly on mycelium, on separate sporogenous cells or on distinct conidiophores.

2. Signs of Moniliaceae family:

Both conidia and conidiophores (if present) are hyaline or brightly coloured; conidiophores are single or in loose clusters.

3. Signs of *Chrysosporium* Corda 1833 genus:

Colonies are usually spreading, white, sometimes cream-coloured, pale brown or yellow, felty and/or powdery. Hyphae are mostly hyaline and smooth-walled, with irregular, more or less orthotopic branching. Fertile hyphae exhibit little or no differentiation. Conidia are terminal and lateral, thallic, borne all over the hyphae, sessile or on short protrusions or side branches, subhyaline or pale yellow, thin- or thick-walled, subglobose, clavate, pyriform, orobovoid, 1-celled, rarely 2-celled, truncate. Intercalary conidia are sometimes present, are solitary, occasionally catenate, subhyaline or pale yellow, broader than the supporting hyphae, normally 1-celled, truncate at both ends. Chlamydospores are occasionally present.

Another source providing information on fungal nomenclature is ATCC (US). Their website is may be accessed on the World Wide Web (HTTP protocol) at atcc.org. CBS also has a website located on the World Wide Web (HTTP protocol) at cbs.knaw.n1 providing relevant information. VKM in Moscow is also a reliable source of such information, located on the World Wide Web (HTTP protocol) at bdt.org.br.bdt.msdn.vkm/general. Another source is the United States Department of Agriculture Research Service website (located on an NT webserver rather than the World Wide Web) at ars-grin.gov/fungaldatabases. All these institutions can provide teaching on the distinguishing characteristics of a *Chrysosporium*.

Strains defined as being of *Myceliophthora thermophila* are not considered to define *Chrysosporium* strains according to the definition of the invention. In the past there has been considerable confusion over the nomenclature of some *Myceliophthora* strains. Preferably the *Chrysosporium* according to the invention are those which are clearly distinguishable as such and cannot be confused with *Myceliophthora*, *Sporotrichum* or *Phanerochaete chrysosporium*.

The following strains are defined as *Chrysosporium* but the definition of *Chrysosporium* is not limited to these strains: *C. botryoides, C. carmichaelii, C. crassitunicatum, C. europae, C. evolceannui, C. farinicola, C. fastidium, C. filiforme, C. georgiae, C. globiferum, C. globiferum* var. *articulatum, C. globiferum* var. *niveum, C. hirundo, C. hispanicum, C. holmii, C. indicum, C. inops, C. keratinophilum, C. kreiselii, C. kuzurovianum, C. lignorum, C. lobatum, C. lucknowense, C. lucknowense* Garg 27K, *C. medium, C. medium* var. *spissescens, C. mephiticum, C. merdarium, C. merdarium* var. *roseum, C. minor, C. pannicola, C. parvum, C. parvum* var. *crescens, C. pilosum, C. pseudomerdarium, C. pyriformis, C. queenslandicum, C. sigleri, C. sulfureum, C. synchronum, C. tropicum, C. undulatum, C. vallenarense, C. vespertilium, C. zonatum.*

*C. lucknowense* forms one of the species of *Chrysosporium* that have raised particular interest as it has provided a natural high producer of cellulase proteins (WO 98/15633 and related U.S. Pat. No. 5,811,381, as well as U.S. Pat. No. 6,015,707). The characteristics of this *Chrysosporium lucknowense* are:

Colonies attain 55 mm diameter on Sabouraud glucose agar in 14 days, are cream-coloured, felty and fluffy; dense and 3-5 mm high; margins are defined, regular, and fimbriate; reverse pale yellow to cream-coloured. Hyphae are hyaline, smooth- and thin-walled, little branched. Aerial hyphae are mostly fertile and closely septate, about 1-3.5 μm wide. Submerged hyphae are infertile, about 1-4.5 μm wide, with the thinner hyphae often being contorted. Conidia are terminal and lateral, mostly sessile or on short, frequently conical protrusions or short side branches. Conidia are solitary but in close proximity to one another, 1-4 conidia developing on one hyphal cell, subhyaline, fairly thin- and smooth-walled, mostly subglobose, also clavate orobovoid, 1-celled, 2.5-11×1.5-6 μm, with broad basal scars (1-2 μm). Intercalary conidia are absent. Chlamydospores are absent. ATCC 44006, CBS 251.72, CBS 143.77 and CBS 272.77 are examples of *Chrysosporium lucknowense* strains and other examples are provided in WO 98/15633 and U.S. Pat. No. 5,811,381.

A further strain was isolated from this species with an even higher production capacity for cellulases. This strain is called C1 by its internal notation and was deposited with the International Depository of the All Russian Collection of microorganisms of the Russian Academy of Sciences Bakrushina Street 8, Moscow, Russia 113184 on Aug. 29, 1996, as a deposit according to the Budapest Treaty and was assigned Accession Number VKM F-3500D. It is called *Chrysosporium lucknowense* Garg 27K. The characteristics of the C1 strain are as follows:

Colonies grow to about 55-66 mm diameter in size on potato-dextrose agar in about 7 days; are white-cream-coloured, felty, 2-3 μm high at the center; margins are defined, regular, fimbriate; reverse pale, cream-coloured. Hyphae are hyaline, smooth- and thin-walled, little branched. Aerial hyphae are fertile, septate, 2-3 mm wide. Submerged hyphae are infertile. Conidia are terminal and lateral; sessile or on short side branches; absent; solitary, but in close proximity to one another, hyaline, thin- and smooth-walled, subglobose, clavate or obovoid, 1-celled, 4-10 μm. Chlamydospores are absent. Intercalary conidia are absent.

The method of isolation of the C1 strain is described in WO 98/15633 and U.S. Pat. No. 5,811,381. Strains exhibiting such morphology are included within the definition of *Chrysosporium* according to the invention. Also included within the definition of *Chrysosporium* are strains derived from

*Chrysosporium* predecessors including those that have mutated somewhat either naturally or by induced mutagenesis. In particular the invention covers mutants of *Chrysosporium* obtained by induced mutagenis, especially by a combination of irradiation and chemical mutagenesis.

For example strain C1 was mutagenised by subjecting it to ultraviolet light to generate strain UV13-6. This strain was subsequently further mutated with N-methyl-N'-nitro-N-nitrosoguanidine to generate strain NG7C-19. The latter strain in turn was subjected to mutation by ultraviolet light resulting in strain UV18-25. During this mutation process the morphological characteristics have varied somewhat in culture in liquid or on plates as well as under the microscope. With each successive mutagenesis the cultures showed less of the fluffy and felty appearance on plates that are described as being characteristic of *Chrysosporium*, until the colonies attained a flat and matted appearance. A brown pigment observed with the wild type strain in some media was also less prevalent in mutant strains. In liquid culture the mutant UV18-25 was noticeably less viscous than the wild type strain C1 and the mutants UV13-6 and NG7C-19. While all strains maintained the gross microscopic characteristics of *Chrysosporium*, the mycelia became narrower with each successive mutation and with UV18-25 distinct fragmentation of the mycelia could be observed. This mycelial fragmentation is likely to be the cause of the lower viscosity associated with cultures of UV18-25. The ability of the strains to sporulate decreased with each mutagenic step. The above illustrates that for a strain to belong to the genus *Chrysosporium* there is some leeway from the above morphological definition. At each mutation step production of cellulase and extracellular proteins has in addition also increased, while several mutations resulted in decrease of protease expression. Criteria with which fungal taxonomy can be determined are available from CBS, VKMF and ATCC for example.

In particular the anamorph form of *Chrysosporium* has been found to be suited for the production application according to the invention. The metabolism of the anamorph renders it extremely suitable for a high degree of expression. A teleomorph should also be suitable as the genetic make-up of the anamorphs and teleomorphs is identical. The difference between anamorph and teleomorph is that one is the asexual state and the other is the sexual state. The two states exhibit different morphology under certain conditions.

It is preferable to use non-toxic *Chrysosporium* strains of which a number are known in the art as this will reduce risks to the environment upon large scale production and simplify production procedures with the concomitant reduction in costs.

An expression-regulating region is a DNA sequence recognised by the host *Chrysosporium* strain for expression. It comprises a promoter sequence operably linked to a nucleic acid sequence encoding the polypeptide to be expressed. The promoter is linked such that the positioning vis-à-vis the initiation codon of the sequence to be expressed allows expression. The promoter sequence can be constitutive or inducible. Any expression regulating sequence or combination thereof capable of permitting expression of a polypeptide from a *Chrysosporium* strain is envisaged. The expression regulating sequence is suitably a fungal expression-regulating region e.g. an ascomycete regulating region. Suitably the fungal expression regulating region is a regulating region from any of the following genera of fungi: *Aspergillus, Trichoderma, Chrysosporium* (preferred), *Hansenula, Mucor, Pichia, Neurospora, Tolypocladium, Rhizomucor, Fusarium, Penicillium, Saccharomyces, Talaromyces* or alternative sexual forms thereof like *Emericella, Hypocrea* e.g. the cellobiohydrolase promoter from *Trichoderma*, glucoamylase promoter from *Aspergillus*, glyceraldehyde phosphate dehydrogenase promoter from *Aspergillus*, alcohol dehydrogenase A and alcohol dehydrogenase R promoter of *Aspergillus*, TAKA amylase promoter from *Aspergillus*, phosphoglycerate and cross-pathway control promoters of *Neurospora*, aspartic proteinase promoter of *Rhizomucor miehei*, lipase promoter of *Rhizomucor miehei* and beta-galactosidase promoter of *Penicillium canescens*. An expression regulating sequence from the same genus as the host strain is extremely suitable, as it is most likely to be specifically adapted to the specific host. Thus preferably the expression regulating sequence is one from a *Chrysosporium* strain.

We have found particular strains of *Chrysosporium* to express proteins in extremely large amounts and natural expression regulating sequences from these strains are of particular interest. These strains are internally designated as *Chrysosporium* strain C1, strain UV13-6, strain NG7C-19 and strain UV18-25. They have been deposited in accordance with the Budapest Treaty with the All Russian Collection (VKM) depository institute in Moscow. Wild type C1 strain was deposited in accordance with the Budapest Treaty with the number VKM F-3500 D, deposit date Aug. 29, 1996, C1 UV13-6 mutant was deposited with number VKM F-3632 D, and deposit date Sep. 20, 1998, C1 NG7C-19 mutant was deposited with number VKM F-3633 D and deposit date Sep. 20, 1998 and C1 UV18-25 mutant was deposited with number VKM F-3631 D and deposit date Sep. 2, 1998.

Preferably an expression-regulating region enabling high expression in the selected host is applied. This can also be a high expression-regulating region derived from a heterologous host, such as are well known in the art. Specific examples of proteins known to be expressed in large quantities and thus providing suitable expression regulating sequences for the invention are without being limited thereto hydrophobin, protease, amylase, xylanase, pectinase, esterase, beta-galactosidase, cellulase (e.g. endo-glucanase, cellobiohydrolase) and polygalacturonase. The high production has been ascertained in both solid state and submerged fermentation conditions. Assays for assessing the presence or production of such proteins are well known in the art. The catalogues of Sigma and Megazyme for example provide numerous examples. Megazyme is located at Bray Business Park, Bray, County Wicklow in Ireland. Sigma Aldrich has many affiliates world wide e.g. USA P.O. Box 14508 St. Louis Mo. For cellulase we refer to commercially available assays such as CMCase assays, endoviscometric assays, Avicelase assays, beta-glucanase assays, RBBCMCase assays, Cellazyme C assays. Xylanase assays are also commercially available (e.g. DNS and Megazyme). Alternatives are well known to a person skilled in the art and can be found from general literature concerning the subject and such information is considered incorporated herein by reference. By way of example we refer to "Methods in Enzymology Volume 1, 1955 right through to volumes 297-299 of 1998. Suitably a *Chrysosporium* promoter sequence is applied to ensure good recognition thereof by the host.

We have found that heterologous expression-regulating sequences work as efficiently in *Chrysosporium* as native *Chrysosporium* sequences. This allows well known constructs and vectors to be used in transformation of *Chrysosporium* as well as offering numerous other possibilities for constructing vectors enabling good rates of expression in this novel expression and secretion host. For example standard *Aspergillus* transformation techniques can be used as described for example by Christiansen et al in Bio/Technol. 6:1419-1422 (1988). Other documents providing details of Aspergillus transformation vectors, e.g. U.S. Pat. Nos. 4,816,405, 5,198,345, 5,503,991, 5,364,770 and 5,578,463, EP-B-215.594 (also for Trichoderma) and their contents are incorporated by reference. As extremely high expression rates for cellulase have been ascertained for Chrysosporium strains, the expression regulating regions of such proteins are particularly preferred. We refer for specific examples to the previously mentioned deposited Chrysosporium strains.

A nucleic acid construct comprising a nucleic acid expression regulatory region from Chrysosporium, preferably from Chrysosporium lucknowense or a derivative thereof forms a separate embodiment of the invention as does the mutant Chrysosporium strain comprising such operably linked to a gene encoding a polypeptide to be expressed. Suitably such a nucleic acid construct will be an expression regulatory region from Chrysosporium associated with cellulase or xylanase expression, preferably cellobiohydrolase expression, more specifically expression of a 55 kDa cellobiohydrolase. The Chrysosporium promoter sequences of an endoglucanase of 25 kDa (C1-EG5) and of an endoglucanase of 43 kDa (C1-EG6), wherein the molecular weights are determined according to SDS PAGE (with the molecular weights according to amino acid sequence data being 21.9 kDa and 39.5 kDa), are provided by way of example. Thus, the Chrysosporium promoter sequences of hydrophobin, protease, amylase, xylanase, esterase, pectinase, beta-galactosidase, cellulase (e.g. endoglucanase, cellobiohydrolase) and polygalacturonase are considered to also fall within the scope of the invention. Any of the promoters or regulatory regions of expression of enzymes disclosed in Table A or B can be suitably employed. The nucleic acid sequence according to the invention can suitably be obtained from a Chrysosporium strain according to the invention, such strain being defined elsewhere in the description. The manner in which promoter sequences can be determined are numerous and well known in the art. Nuclease deletion experiments of the region upstream of the ATG codon at the beginning of the relevant gene will provide such sequence. Also for example analysis of consensus sequences can lead to finding a gene of interest. Using hybridisation and amplification techniques one skilled in the art can readily arrive at the corresponding promoter sequences.

The promoter sequences of C1 endoglucanases were identified in this manner, by cloning the corresponding genes, and are given in SEQ ID No.'s 5 (EG5) and 6 (EG6), respectively. Other preferred promoters according to the invention are the 55 kDa cellobiohydrolase (CBH1) promoter and the 30 kDa xylanase (XylF) promoters, as the enzymes are expressed at high level by their own promoters. The corresponding promoter sequences can be identified in a straightforward manner by cloning as described below for the endoglucanase promoters, using the sequence information given in SEQ ID No. 1 (for CBH1) and SEQ ID No. 2 (for XylF), respectively. The promoters of the carbohydrate-degrading enzymes of Chrysosporium, especially C1 promoters, can advantageously be used for expressing desired polypeptides in a host organism, especially a fungal or other microbial host organism. Promoter sequences having at least 60%, preferably at least 70%, most preferably at least 80% nucleotide sequence identity with the sequence given in SEQ ID No's 1 and 2, or with the sequences found for other Chrysosporium genes, are part of the present invention.

For particular embodiments of the recombinant strain and the nucleic acid sequence according to the invention we also refer to the examples. We also refer for the recombinant strains to prior art describing high expression promoter sequences in particular those providing high expression in fungi e.g. such as are disclosed for Aspergillus and Trichoderma. The prior art provides a number of expression regulating regions for use in Aspergillus e.g. U.S. Pat. No. 5,252,726 of Novo and U.S. Pat. No. 5,705,358 of Unilever. The contents of such prior art are hereby incorporated by reference.

The hydrophobin gene is a fungal gene that is highly expressed. It is thus suggested that the promoter sequence of a hydrophobin gene, preferably from Chrysosporium, may be suitably applied as expression regulating sequence in a suitable embodiment of the invention. Trichoderma reesei and Trichoderma harzianum gene sequences for hydrophobin have been disclosed for example in the prior art as well as a gene sequence for Aspergillus fumigatis and Aspergillus nidulans and the relevant sequence information is hereby incorporated by reference (Munoz et al, Curr. Genet. 1997, 32(3):225-230; Nakari-Setala T. et al, Eur. J. Biochem. 1996 15:235 (1-2):248-255, M. Parta et al, Infect. Immun. 1994 62 (10): 4389-4395 and Stringer M. A. et al. Mol. Microbiol. 1995 16(1):33-44). Using this sequence information a person skilled in the art can obtain the expression regulating sequences of Chrysosporium hydrophobin genes without undue experimentation following standard techniques as suggested already above. A recombinant Chrysosporium strain according to the invention can comprise a hydrophobin-regulating region operably linked to the sequence encoding the polypeptide of interest.

An expression regulating sequence can also additionally comprise an enhancer or silencer. These are also well known in the prior art and are usually located some distance away from the promoter. The expression regulating sequences can also comprise promoters with activator binding sites and repressor binding sites. In some cases such sites may also be modified to eliminate this type of regulation. Filamentous fungal promoters in which creA sites are present have been described. Such creA sites can be mutated to ensure the glucose repression normally resulting from the presence of the non-mutated sites is eliminated. Gist-Brocades' WO 94/13820 illustrates this principle. Use of such a promoter enables production of the polypeptide encoded by the nucleic acid sequence regulated by the promoter in the presence of glucose. The same principle is also apparent from WO 97/09438. These promoters can be used either with or without their creA sites. Mutants in which the creA sites have been mutated can be used as expression regulating sequences in a recombinant strain according to the invention and the nucleic acid sequence it regulates can then be expressed in the presence of glucose. Such Chrysosporium promoters ensure derepression in an analogous manner to that illustrated in WO 97/09438. The identity of creA sites is known from the prior art. Alternatively, it is possible to apply a promoter with CreA binding sites that have not been mutated in a host strain with a mutation elsewhere in the repression system e.g. in the creA gene itself, so that the strain can, notwithstanding the presence of creA binding sites, produce the protein or polypeptide in the presence of glucose.

Terminator sequences are also expression-regulating sequences and these are operably linked to the 3' terminus of the sequence to be expressed. Any fungal terminator is likely to be functional in the host Chrysosporium strain according to the invention. Examples are A. nidulans trpC terminator (1), A. niger alpha-glucosidase terminator (2), A. niger glucoamylase terminator (3), Mucor miehei carboxyl protease terminator (U.S. Pat. No. 5,578,463) and the Trichoderma reesei cellobiohydrolase terminator. Naturally Chrysosporium terminator sequences will function in Chrysosporium and are suitable e.g. CBH1 or EG6 terminator.

A suitable recombinant *Chrysosporium* strain according to the invention has the nucleic acid sequence to be expressed operably linked to a sequence encoding the amino acid sequence defined as signal sequence. A signal sequence is an amino acid sequence which when operably linked to the amino acid sequence of the expressed polypeptide allows secretion thereof from the host fungus. Such a signal sequence may be one normally associated with the heterologous polypeptide or may be one native to the host. It can also be foreign to both host and the polypeptide. The nucleic acid sequence encoding the signal sequence must be positioned in frame to permit translation of the signal sequence and the heterologous polypeptide. Any signal sequence capable of permitting secretion of a polypeptide from a *Chrysosporium* strain is envisaged. Such a signal sequence is suitably a fungal signal sequence, preferably an ascomycete signal sequence.

Suitable examples of signal sequences can be derived from yeasts in general or any of the following specific genera of fungi: *Aspergillus, Trichoderma, Chrysosporium, Pichia, Neurospora, Rhizomucor, Hansenula, Humicola, Mucor, Tolypocladium, Fusarium, Penicillium, Saccharomyces, Talaromyces* or alternative sexual forms thereof like *Emericella, Hypocrea*. Signal sequences that are particularly useful are often natively associated with the following proteins a cellobiohydrolase, an endoglucanase, a beta-galactosidase, a xylanase, a pectinase, an esterase, a hydrophobin, a protease or an amylase. Examples include amylase or glucoamylase of *Aspergillus* or *Humicola* (4), TAKA amylase of *Aspergillus oryzae*, alpha-amylase of *Aspergillus niger*, carboxyl peptidase of *Mucor* (U.S. Pat. No. 5,578,463), a lipase or proteinase from *Rhizomucor miehei*, cellobiohydrolase of *Trichoderma* (5), beta-galactosidase of *Penicillium canescens* and alpha mating factor of *Saccharomyces.*

Alternatively the signal sequence can be from an amylase or subtilisin gene of a strain of *Bacillus*. A signal sequence from the same genus as the host strain is extremely suitable as it is most likely to be specifically adapted to the specific host thus preferably the signal sequence is a signal sequence of *Chrysosporium*. We have found particular strains of *Chrysosporium* to excrete proteins in extremely large amounts and naturally signal sequences from these strains are of particular interest. These strains are internally designated as *Chrysosporium* strain C1, strain UV13-6, strain NG7C-19 and strain UV18-25. They have been deposited in accordance with the Budapest Treaty as described elsewhere in this description. Signal sequences from filamentous fungi, yeast and bacteria are useful. Signal sequences of non-fungal origin are also considered useful, particularly bacterial, plant and mammalian.

A recombinant *Chrysosporium* strain according to any of the embodiments of the invention can further comprise a selectable marker. Such a selectable marker will permit easy selection of transformed or transfected cells. A selectable marker often encodes a gene product providing a specific type of resistance foreign to the non-transformed strain. This can be resistance to heavy metals, antibiotics and biocides in general. Prototrophy is also a useful selectable marker of the non-antibiotic variety. Non-antibiotic selectable markers can be preferred where the protein or polypeptide of interest is to be used in food or pharmaceuticals with a view to speedier or less complicated regulatory approval of such a product. Very often the GRAS indication is used for such markers. A number of such markers are available to the person skilled in the art. The FDA e.g. provides a list of such. Most commonly used are selectable markers selected from the group conferring resistance to a drug or relieving a nutritional defect e.g the group comprising amdS (acetamidase), hph (hygromycin phosphotransferase), pyrG (orotidine-5'-phosphate decarboxylase), trpC (anthranilate synthase), argB (ornithine carbamoyltransferase), sC (sulphate adenyltransferase), bar (phosphinothricin acetyltransferase), glufosinate resistance, niaD (nitrate reductase), a bleomycin resistance gene, more specifically Sh ble, sulfonylurea resistance e.g. acetolactate synthase mutation ilv1. Selection can also be carried out by virtue of cotransformation where the selection marker is on a separate vector or where the selection marker is on the same nucleic acid fragment as the polypeptide-encoding sequence for the polypeptide of interest.

As used herein the term heterologous polypeptide is a protein or polypeptide not normally expressed and secreted by the *Chrysosporium* host strain used for expression according to the invention. The polypeptide can be of plant or animal (vertebrate or invertebrate) origin e.g. mammalian, fish, insect, or micro-organism origin, with the proviso it does not occur in the host strain. A mammal can include a human. A micro-organism comprises viruses, bacteria, archaebacteria and fungi i.e. filamentous fungi and yeasts. Bergey's Manual for Bacterial Determinology provides adequate lists of bacteria and archaebacteria. For pharmaceutical purposes quite often a preference will exist for human proteins thus a recombinant host according to the invention forming a preferred embodiment will be a host wherein the polypeptide is of human origin. For purposes such as food production suitably the heterologous polypeptide will be of animal, plant or algal origin. Such embodiments are therefore also considered suitable examples of the invention. Alternative embodiments that are useful also include a heterologous polypeptide of any of bacterial, yeast, viral, archaebacterial and fungal origin. Fungal origin is most preferred.

A suitable embodiment of the invention will comprise a heterologous nucleic acid sequence with adapted codon usage. Such a sequence encodes the native amino acid sequence of the host from which it is derived, but has a different nucleic acid sequence, i.e. a nucleic acid sequence in which certain codons have been replaced by other codons encoding the same amino acid but which are more readily used by the host strain being used for expression. This can lead to better expression of the heterologous nucleic acid sequence. This is common practice to a person skilled in the art. This adapted codon usage can be carried out on the basis of known codon usage of fungal vis-à-vis non-fungal codon usage. It can also be even more specifically adapted to codon usage of *Chrysosporium* itself The similarities are such that codon usage as observed in *Trichoderma, Humicola* and *Aspergillus* should enable exchange of sequences of such organisms without adaptation of codon usage. Details are available to the skilled person concerning the codon usage of these fungi and are incorporated herein by reference.

The invention is not restricted to the above mentioned recombinant *Chrysosporium* strains, but also covers a recombinant *Chrysosporium* strain comprising a nucleic acid sequence encoding a homologous protein for a *Chrysospo-* rium strain, said nucleic acid sequence being operably linked to an expression-regulating region and said recombinant strain expressing more of said protein than the corresponding non-recombinant strain under the same conditions. In the case of homologous polypeptide of interest such is preferably a neutral or alkaline enzyme like a hydrolase, a protease or a carbohydrate degrading enzyme as already described elsewhere. The polypeptide may also be acidic. Preferably the recombinant strain will express the polypeptide in greater amounts than the non-recombinant strain. All comments mentioned vis-à-vis the heterologous polypeptide are also valid (mutatis mutandis) for the homologous polypeptide cellulase.

Thus the invention also covers genetically engineered *Chrysosporium* strains wherein the sequence that is introduced can be of *Chrysosporium* origin. Such a strain can, however, be distinguished from natively occurring strains by virtue of for example heterologous sequences being present in the nucleic acid sequence used to transform or transfect the *Chrysosporium*, by virtue of the fact that multiple copies of the sequence encoding the polypeptide of interest are present or by virtue of the fact that these are expressed in an amount exceeding that of the non-engineered strain under identical conditions or by virtue of the fact that expression occurs under normally non-expressing conditions. The latter can be the case if an inducible promoter regulates the sequence of interest contrary to the non-recombinant situation or if another factor induces the expression than is the case in the non-engineered strain. The invention as defined in the preceding embodiments is not intended to cover naturally occurring *Chrysosporium* strains. The invention is directed at strains derived through engineering either using classical genetic technologies or genetic engineering methodologies.

All the recombinant strains of the invention can comprise a nucleic acid sequence encoding a heterologous protein selected from carbohydrate-degrading enzymes (cellulases, xylanases, mannanases, mannosidases, pectinases, amylases, e.g. glucoamylases, α-amylases, alpha- and beta-galactosidases, α- and β-glucosidases, β-glucanases, chitinases, chitanases), proteases (endoproteases, amino-proteases, amino- and carboxy-peptidases, keratinases), other hydrolases (lipases, esterases, phytases), oxidoreductases (catalases, glucose-oxidases) and transferases (transglycosylases, transglutaminases, isomerases and invertases).

TABLE A pH range where enzymes retain activity and/or stability

| Sample | pH range retaining >50% enzymatic activity | | | pH range retaining >70% enzymatic activity | | | Stability (20 h, 50° C.) % from max pH 7.5/8 |
|---|---|---|---|---|---|---|---|
| | CMCase | RBB-CMCase | Other substrates | CMCase | RBB-CMCase | Other substrates | |
| 30 Kd protease (alkaline) 30 kD | — | — | 12.5 | — | — | 12.0 | — |
| Xyl (alkaline) | — | — | 10.0 | — | — | 8.5 | 80 |
| 51 kD Xyl | — | — | 8.0 | — | — | 7.5 | — |
| 60 kD Xyl | — | — | 9.5 | — | — | 9.0 | 85 |
| 45 kD endo | 7.0 | 8.0 | — | 6.5 | 7.0 | — | 75 |
| 55 kD endo | 8.0 | 8.0 | — | 7.0 | 7.0 | — | 55 |
| 25 kD(21.8 kD*)endo | 7.5 | 10.0 | — | 6.5 | 9.0 | — | 80 |
| 43 kD(39.6 kD*)endo | 8.0 | 8.0 | — | 7.2 | 7.2 | — | — |
| 45 kD α,ι-Gal/β-Gluc | — | — | 6.8 | — | — | 5.7 | — |
| 48 kD CBH with β-Gluc traces | 5.2 | 7.5 | 8.0 | 5.0 | 6.8 | — | — |
| 55 kD CBH | 8.0 | 9.0 | — | 7.4 | 8.5 | — | 70 |
| 65 kD PGU | — | — | 8.0 | — | — | 7.3 | — |
| 90 kD protease | — | — | 9.0 | — | — | 9.0 | — |
| 100 kD esterase | — | — | 9.0 | — | — | 9.0 | — |

* molecular weights (by MALDI)

Note:
* all other molecular weights by SDS PAGE
* enzymes were taken in equal protein contents
* xyl = xylanase
* endo = endoglucanase
* gal = galactosidase
* gluc = glucosidase
* CBN = cellbiohydrolase
* PGU = polygalacturonase

TABLE B

Activities of enzymes isolated from ultrafiltrate from 18-25 strain toward different substrates (pH 5), units/mg protein

| Sample | pI | CMC 50° C. | RBB-CMC 40° C. | CMC-41 40° C. | FP 50° C. | CMC (visc) 40° C. | b-Glucan 50° C. | pNP-a G 40° C. | pNP-b G 40° C. | Cellobiose 40° C. | Avicel 40° C. | MUF cellobioside 40° C. |
|---|---|---|---|---|---|---|---|---|---|---|---|---|
| 30 kD protease | 8.9 | 0 | 0 | 0 | 0 | 0 | 0 | — | 0 | 0 | 0 | 0 |
| 30 kD Xyl | 9.1 | 0.1 | 2 | 0.1 | 0.16 | 0.1 | 0 | — | 0 | — | 0 | 0 |
| 51 kD Xyl | 8.7 | 0.1 | 4.2 | — | 0.19 | — | 0 | — | 0 | — | 0 | 0 |
| 60 kD Xyl | 4.7 | 0 | — | — | 0 | — | 0 | — | — | 0 | 0 | 0.14 |
| 45 kD endo | 6 | 51 | 86 | 7.6 | 0.2 | 47 | 36 | — | 0 | — | 0.5 | 0 |

TABLE B-continued

Activities of enzymes isolated from ultrafiltrate from 18-25 strain toward different substrates (pH 5), units/mg protein

| | | | | | | | | | | | | |
|---|---|---|---|---|---|---|---|---|---|---|---|---|
| 55 kD endo | 4.9 | 47 | 94 | 7.7 | 0.3 | 39 | 25 | — | 0 | — | 0.5 | 0 |
| 25 kD (21.8 kD*) endo | 4.1 | 19 | 15 | 3.9 | 0.3 | 11 | 3.8 | — | 0 | 0 | 0.05 | 0 |
| 43 kD (39.6 kD*) endo | 4.2 | 0.43 | 0.2 | 0.1 | 0 | 0.2 | 0.2 | — | 0 | 0 | 0 | 0 |
| 45 kD a,b-Gal/b-Gluc | 4.2 | 0 | 0 | 0 | 0 | 0.01 | 0.01 | 0 | 0.4 | 0.06 | 0 | 0 |
| 40 kD CBH with b-Gluc traces + glucono-d-lactone | 4.4 | 0.67 | 1.3 | 1.2 | 0.4 | 0.8 | 0.77 | 0 | 1.70 | 0.08 | 0 | 0.2 |
| 55 kD CBH with b-Gluc traces + glucono-d-lactone | 4.4 | 0.7 | 0.16 | 0.27 | 0.4 | 0.1 | 0.1 | — | 0.050 | 0.08 | 0.46 | 0.2 0.14 |
| 65 kD PGU | 4.4 | 0 | 0 | 0 | 0 | 0 | 0 | — | 0 | 0 | 0 | 0 |
| 90 kD protease | 4.2 | — | — | — | — | — | — | — | — | — | — | — |
| 100 kD esterase | 4.5 | 0 | 0 | 0 | 0 | 0 | 0 | — | 0 | 0 | 0 | 0 |

| Sample | MUF-lactoside 40° C. | MUF-xyloside 40° C. | Lactose 40° C. | Xylan 50° C. | Polygalacturonic acid 50° C. | MUF-glucoside 40° C. | Galactomannan 50° C. | pNP-a galactoside 40° C. | pNP-b galactoside 40° C. | Dyed casein** 50° C. | pNP butyrate 60° C. |
|---|---|---|---|---|---|---|---|---|---|---|---|
| 30 kD protease | 0 | 0 | 0 | 0 | 0 | 0 | 0 | 0 | 0 | 0.4 | 0 |
| 30 kD Xyl | 0 | 0 | — | 25 | 0 | 0 | 0 | 0 | — | 0 | 0 |
| 51 kD Xyl | 0 | 0 | — | 19 | 0 | 0 | 0 | 0 | — | 0 | 0 |
| 60 kD Xyl | 0.02 | 0.04 | — | 16.3 | 0 | 0 | 0 | 0 | 0 | 0 | 0 |
| 45 kD endo | 0 | 0 | — | 1 | — | 0 | 1.8 | 0 | — | 0 | 0 |
| 55 kD endo | 0 | 0 | — | 0 | — | 0 | 0.4 | 0 | — | 0 | 0 |
| 25 kD (21.8 kD*) endo | 0 | — | 0 | 0.03 | 0 | — | 0 | 0 | 0 | 0 | 0 |
| 43 kD (39.6 kD*) endo | 0 | — | 0 | 0 | 0 | — | 0 | 0 | 0 | 0 | 0 |
| 45 kD a,b-Gal/b-Gluc | 0 | — | 0.01 | 0 | 0.1 | 0.1 | 0.2 | 0.2 | 0.03 | 0 | 1.7 |
| 40 kD CBH with b-Gluc traces + glucono-d-lactone | 0.36 0.36 | — | 0 | 0 | 0.1 | 0.4 | 0 | 0 | 0 | 0 | 2.3 |
| 55 kD CBH with b-Gluc traces + glucono-d-lactone | 0.7 0.6 | — | 0 | 0.1 | 0 | — | 0 | 0 | 0 | 0 | 0 |
| 65 kD PGU | 0 | — | 0 | 0 | 1 | — | 0 | 0 | 0 | 0 | 0 |
| 90 kD protease | — | — | — | — | — | — | — | — | — | 0.01 | — |
| 100 kD esterase | 0 | — | 0 | 0 | 0 | 0 | 0 | 0 | 0 | 0 | 0.8 |

*molecular weights, (by MALDI)
**activity toward dyed casein was expressed in arbitrary units/mg The most interesting products to be produced according to invention are cellulases, xylanases, pectinases, lipases and proteases, wherein cellulases and xylanases cleave beta-1,4-bonds, and cellulases comprise endoglucanases, cellobiohydrolases and beta-glucosidases. These proteins are extremely useful in various industrial processes known in the art. Specifically for cellulases we refer e.g. to WO 98/15633 describing cellobiohydrolases and endoglucanases of use. The contents of said application are hereby incorporated by reference. We also refer to Tables A and B providing further details of interesting *Chrysosporium* proteins.

It was found according to the invention, that *Chrysosporium* mutants can be made that have reduced expression of protease, thus making them even more suitable for the production of proteinaceous products, especially if the proteinaceous product is sensitive to protease activity. Thus the invention also involves a mutant *Chrysosporium* strain which produces less protease than non-mutant *Chrysosporium* strain, for example less than *C. lucknowense* strain C1 (VKM F-3500 D). In particular the protease activity of such strains is less than half the amount, more in particular less than 30% of the amount produced by C1 strain. The decreased protease activity can be measured by known methods, such as by measuring the halo formed on skim milk plates or BSA degradation.

An embodiment of the invention that is of particular interest is a recombinant *Chrysosporium* according to the invention wherein the nucleic acid sequence encoding the polypeptide of interest encodes a polypeptide that is inactivated or unstable at acid pH i.e. pH below 6, even below 5.5, more suitably even below pH 5 and even as low as or lower than pH 4. This is a particularly interesting embodiment, as the generally disclosed fungal expression systems are not cultured under conditions that are neutral to alkaline, but are cultured at acidic pH. Thus the system according to the invention provides a safe fungal expression system for proteins or polypeptides that are susceptible to being inactivated or are unstable at acid pH.

Quite specifically a recombinant strain as defined in any of the embodiments according to the invention, wherein the nucleic acid sequence encoding the polypeptide of interest encodes a protein or polypeptide exhibiting optimal activity and/or stability at a pH above 5, preferably at neutral or alkaline pH (i.e. above 7) and/or at a pH higher than 6, is considered a preferred embodiment of the invention. More than 50%, more than 70% and even more than 90% of optimal activities at such pH values are anticipated as being particularly useful embodiments. A polypeptide expressed under the cultivation conditions does not necessarily have to be active at the cultivation conditions, in fact it can be advantageous for it to be cultured under conditions under which it is inactive as its active form could be detrimental to the host. This is the case for proteases for example. What is however required is for the protein or polypeptide to be stable under the cultivation conditions. The stability can be thermal stability. It can also be stability against specific compositions or chemicals, such as are present for example in compositions or processes of production or application of the polypeptide or protein of interest. Linear alkylbenzene sulfonate (LAS) in detergent compositions comprising cellulases or lipases, etc. is an example of a chemical often detrimental to proteins. The time periods of use in applications can vary from short to long exposure so stability can be over a varying length of time varying per application. The skilled person will be able to ascertain the correct conditions on a case by case basis. One can use a number of commercially available assays to determine the optimal activities of the various enzymatic products. The catalogues of Sigma and Megazyme for example show such. Specific examples of tests are mentioned elsewhere in the description. The manufacturers provide guidance on the application.

We have surprisingly found that a *Chrysosporium* strain that can be suitably used to transform or transfect with the sequence of interest to be expressed is a strain exhibiting relatively low biomass. We have found that *Chrysosporium* strains having a biomass two to five times lower than that of *Trichoderma reesei* when cultured to a viscosity of 200-600 cP at the end of fermentation and exhibiting a biomass of 10 to 20 times lower than that of *Aspergillus niger* when cultured to a viscosity of 1500-2000 cP under corresponding conditions, i.e. their respective optimal cultivation conditions can provide a high level of expression. This level of expression far exceeds that of the two commercial reference strains at a much lower biomass and at much lower viscosity. This means that the yield of expression of such *Chrysosporium* strains will be appreciably higher than from *Aspergillus niger* and *Trichoderma reesei*. Such a transformed or transfected *Chrysosporium* strain forms a suitable embodiment of the invention.

We find a biomass of 0.5-1.0 g/l for *Chrysosporium* strain C1 (18-25) as opposed to 2.5-5.5 g/l for *Trichoderma reesei* and 5-10 g/l of *Aspergillus niger* under the above described conditions. In the Examples we provide details of this process.

In a suitable embodiment a recombinant *Chrysosporium* strain according to the invention produces protein or polypeptide in at least the amount equivalent to the production in moles per liter of cellulase by the strain UV13-6 or NG7C-19, and most preferably at least equivalent to or higher than that of the strain UV18-25 under the corresponding or identical conditions, i.e. their respective optimal cultivation conditions.

Unexpectedly we have also found that expression and secretion rates are exceedingly high when using a *Chrysosporium* strain exhibiting the mycelial morphology of strain UV18-25 i.e. fragmented short mycelia. Thus a recombinant strain according to the invention will preferably exhibit such morphology. The invention however also covers non-recombinant strains or otherwise engineered strains of *Chrysosporium* exhibiting this novel and inventive characteristic. Also covered by the invention is a recombinant *Chrysosporium* strain in any of the embodiments described according to the invention further exhibiting reduced sporulation in comparison to C1, preferably below that of strain UV13-6, preferably below that of NG7C-19, preferably below that of UV18-25 under equivalent fermenter conditions. Also covered by the invention is a recombinant *Chrysosporium* strain in any of the embodiments described according to the invention further exhibiting at least the amount of protein production ratio to biomass in comparison to C1, preferably in comparison to that of any of strains UV13-6, NG7C-19 and UV18-25 under equivalent fermenter conditions. The invention however also covers non-recombinant strains or otherwise engineered strains of *Chrysosporium* exhibiting this novel and inventive characteristic as such or in combination with any of the other embodiments.

Another attractive embodiment of the invention also covers a recombinant *Chrysosporium* strain exhibiting a viscosity below that of strain NG7C-19, preferably below that of UV18-25 under corresponding or identical fermenter conditions. The invention however also covers non-recombinant strains or otherwise engineered strains of *Chrysosporium* exhibiting this novel and inventive characteristic as such or in combination with any of the other embodiments. We have determined that the viscosity of a culture of UV18-25 is below 10 cP opposed to that of *Trichoderma reesei* being of the order 200-600 cP, with that of *Aspergillus niger* being of the order 1500-2000 cP under their respective optimal culture conditions at the end of fermentation. The process used for such determination is provided in the examples.

Viscosity can be assessed in many cases by visual monitoring. The fluidity of the substance can vary to such a large extent that it can be nearly solid, sauce like or liquid. Viscosity can also readily be ascertained by Brookfield rotational viscometry, use of kinematic viscosity tubes, falling ball viscometer or cup type viscometer. The yields from such a low viscosity culture are higher than from the commercial known higher viscosity cultures per time unit and per cell.

The processing of such low viscosity cultures according to the invention is advantageous in particular when the cultures are scaled up. The subject *Chrysosporium* strains with the low viscosity perform very well in cultures as large as up to 150,000 liter cultures. Thus any culture size up to 150,000 liters provides a useful embodiment of the invention. Any other conventional size of fermentation should be carried out well with the strains according to the invention. The reasoning behind this is that problems can arise in large scale production with the formation of aggregates that have mycelia that are too dense and/or are unevenly distributed. The media as a result cannot be effectively utilised during the culture thus leading to an inefficient production process in particular in large scale fermentations i.e. over 150,000 liters. Aeration and mixing become problematic leading to oxygen and nutrient starvation and thus reduced concentration of productive biomass and reduced yield of polypeptide during the culture and/or can result in longer fermentation times. In addition high viscosity and high shear are not desirable in commercial fermentation processes and in current commercial processes they are the production limiting factors. All these negative aspects can be overcome by the *Chrysosporium* host according to the invention which exhibits much better characteristics than *Trichoderma reesei*, *Aspergillus niger* and *Aspergillus oryzae* that are commercially used in this respect i.e. exhibits better protein production levels and viscosity properties and biomass figures.

A *Chrysosporium* strain selected from C1, UV13-6, NG7C-19 and UV18-25 illustrates various aspects of the invention exceedingly well. The invention however also covers recombinant strains or otherwise engineered strains of *Chrysosporium* derived from the four deposited strains that also exhibit any of the novel and inventive characteristics as such or in combination. The deposit data for these strains have been presented elsewhere in the description. The invention also covers recombinant strains or otherwise engineered strains of *Chrysosporium* derived from the four deposited strains that also exhibit any of the novel and inventive characteristics as such or in combination. A *Chrysosporium* strain according to the invention also comprises a strain exhibiting under the corresponding culture conditions a biomass at least twice as low as that of *Trichoderma reesei*, suitably even more up to 5 times lower than that of *Trichoderma reesei*, specifically of a *Trichoderma reesei* exhibiting a viscosity of 200-600 cP as disclosed under the conditions of the examples. A *Chrysosporium* strain according to the invention also comprises a strain producing the polypeptide in at least the amount in moles per liter of cellulase by the strain C1, UV13-6, NG7C-19 or UV18-25 under the corresponding or identical conditions.

*Chrysosporium* strains according to the invention are further preferred if they exhibit optimal growth conditions at neutral to alkaline pH and temperatures of 25-43° C. A preference can exist for neutral and even for alkaline pH. Such production conditions are advantageous to a number of polypeptides and proteins, in particular those susceptible to attack by acidic pH or those that are inactive or unstable at low temperatures. It is however also an embodiment of the invention to include *Chrysosporium* strains that can be cultured at acidic pH as this can be useful for certain proteins and polypeptides. A suitable acidic pH lies from 7.0. An acidic pH lower than 6.5 is envisaged as providing a good embodiment of the invention. A pH around 5.0-7.0 is also a suitable embodiment. A neutral pH can be 7.0 or around 7 e.g. 6.5-7.5. As stated elsewhere the pH of optimal interest depends on a number of factors that will be apparent to the person skilled in the art. A pH higher than 7.5 is alkaline, suitably between 7.5-9.0 can be used.

When comparing data of strains according to the invention with other strains perhaps having other optimal conditions (e.g. *Aspergillus* and *Trichoderma*) for viscosity measurements, biomass determination or protein production comparisons should be made using the relevant optimal conditions for the relevant strain. This will be obvious to the person skilled in the art.

A *Chrysosporium* strain according to any of the abovementioned embodiments of the invention, said strain further exhibiting production of one or more of the fungal enzymes selected from the carbohydrate-degrading enzymes, proteases, other hydrolases, oxidoreductase, and transferases mentioned above is considered a particularly useful embodiment of the invention. The most interesting products are specifically cellulases, xylanases, pectinases, lipases and proteases. Also useful as embodiment of the invention however is a *Chrysosporium* strain exhibiting production of one or more fungal enzymes that exhibit neutral or alkaline optimal stability and/or activity, preferably alkaline optimal stability and/or activity, said enzyme being selected from carbohydrate-degrading enzymes, hydrolases and proteases, preferably hydrolases and carbohydrate-degrading enzymes. In the case of non-recombinant *Chrysosporium*, such enzymes are suitably other than cellulase as disclosed in WO 98/15633. Enzymes of particular interest are xylanases, proteases, esterases, alpha-galactosidases, beta-galactosidases, beta-glucanases and pectinases. The enzymes are not limited to the aforementioned. The comments vis-à-vis stability and activity elsewhere in the description are valid here also.

The invention also covers a method of producing a polypeptide of interest, said method comprising culturing a *Chrysosporium* strain in any of the embodiments according to the invention under conditions permitting expression and preferably secretion of the polypeptide and recovering the subsequently produced polypeptide of interest.

Where protein or polypeptide is mentioned, variants and mutants e.g. substitution, insertion or deletion mutants of naturally occurring proteins are intended to be included that exhibit the activity of the non-mutant. The same is valid vis-à-vis the corresponding nucleic acid sequences. Processes such as gene shuffling, protein engineering and directed evolution, site directed mutagenesis and random mutagenesis are processes through which such polypeptides, variants or mutants can be obtained. U.S. Pat. No. 5,223,409, U.S. Pat. No. 5,780,279 and U.S. Pat. No. 5,770,356 provide teaching of directed evolution. Using this process a library of randomly mutated gene sequences created for example by gene shuffling via error prone PCR occurs in any cell type. Each gene has a secretion region and an immobilising region attached to it such that the resulting protein is secreted and stays fixed to the host surface. Subsequently conditions are created that necessitate the biological activity of the particular polypeptide. This occurs for a number of cycles ultimately leading to a final gene with the desired characteristics. In other words a speeded up directed process of evolution. U.S. Pat. No. 5,763,192 also describes a process for obtaining DNA, RNA, peptides, polypeptides or protein by way of synthetic polynucleotide coupling stochastically generated sequences, introduction thereof into a host followed by selection of the host cell with the corresponding predetermined characteristic.

Another application of the method of the present invention is in the process of "directed evolution", wherein novel protein-encoding DNA sequences are generated, the encoded proteins are expressed in a host cell, and those sequences encoding proteins having a desired characteristic are mutated and expressed again. The process is repeated for a number of cycles until a protein with the desired characteristics is obtained. Gene shuffling, protein engineering, error-prone PCR, site-directed mutagenesis, and combinatorial and random mutagenesis are examples of processes through which novel DNA sequences encoding exogenous proteins can be generated. U.S. Pat. Nos. 5,223,409, 5,780,279 and 5,770,356 provide teaching of directed evolution. See also Kuchner and Arnold, Trends in Biotechnology, 15:523-530 (1997); Schmidt-Dannert and Arnold, Trends in Biotech., 17:135-136 (1999); Arnold and Volkov, Curr. Opin. Chem. Biol., 3:54-59 (1999); Zhao et al., Manual of Industrial Microbiology and Biotechnology, 2nd Ed., (Demain and Davies, eds.) pp. 597-604, ASM Press, Washington D.C., 1999; Arnold and Wintrode, Encyclopedia of Bioprocess Technology: Fermentation, Biocatalysis, and Bioseparation, (Flickinger and Drew, eds.) pp. 971-987, John Wiley & Sons, New York, 1999; and Minshull and Stemmer, Curr. Opin. Chem. Biol. 3:284-290.

An application of combinatorial mutagenesis is disclosed in Hu et al., Biochemistry. 1998 37:10006-10015. U.S. Pat. No. 5,763,192 describes a process for obtaining novel protein-encoding DNA sequences by stochastically generating synthetic sequences, introducing them into a host, and selecting host cells with the desired characteristic. Methods for effecting artificial gene recombination (DNA shuffling) include random priming recombination (Z. Shao, et al., Nucleic Acids Res., 26:681-683 (1998)), the staggered extension process (H. Zhao et al., Nature Biotech., 16:258-262 (1998)), and heteroduplex recombination (A. Volkov et al., Nucleic Acids Res., 27:e18 (1999)). Error-prone PCR is yet another approach (Song and Rhee, Appl. Environ. Microbiol. 66:890-894 (2000)).

There are two widely-practiced methods of carrying out the selection step in a directed evolution process. In one method, the protein activity of interest is somehow made essential to the survival of the host cells. For example, if the activity desired is a cellulase active at pH 8, a cellulase gene could be mutated and introduced into the host cells. The transformants are grown with cellulose as the sole carbon source, and the pH raised gradually until only a few survivors remain. The mutated cellulase gene from the survivors, which presumably encodes a cellulase active at relatively high pH, is subjected to another round of mutation, and the process is repeated until transformants that can grow on cellulose at pH 8 are obtained. Thermostable variants of enzymes can likewise be evolved, by cycles of gene mutation and high-temperature culturing of host cells (Liao et al., Proc. Natl. Acad. Sci. USA 83:576-580 (1986); Giver et al., Proc. Natl. Acad. Sci. USA. 95:12809-12813 (1998).

An alternative to the massively parallel "survival of the fittest" approach is serial screening. In this approach, individual transformants are screened by traditional methods, such as observation of cleared or colored zones around colonies growing on indicator media, calorimetric or fluorometric enzyme assays, immunoassays, binding assays, etc. See for example Joo et al., Nature 399:670-673 (1999), where a cytochrome P450 monooxygenase not requiring NADH as a cofactor was evolved by cycles of mutation and screening; May et al., Nature Biotech. 18:317-320 (2000), where a hydantoinase of reversed stereoselectivity was evolved in a similar fashion; and Miyazaki et al., J. Mol. Biol. 297:1015-1026 (2000), where a thermostable subtilisin was evolved.

Standard cloning and protein or polypeptide isolation techniques can be used to arrive at the required sequence information. Parts of known sequences can be used as probes to isolate other homologues in other genera and strains. The nucleic acid sequence encoding a particular enzyme activity can be used to screen a *Chrysosporium* library for example. A person skilled in the art will realise which hybridisation conditions are appropriate. Conventional methods for nucleic acid hybridisation construction of libraries and cloning techniques are described in Sambrook et al (Eds) (1989) In "Molecular Cloning. A Laboratory Manual" Cold Spring Harbor Press, Plainview, N.Y., and Ausubel et al (Eds) "Current Protocols in Molecular Biology" (1987) John Wiley and Sons, New York. The relevant information can also be derived from later handbooks and patents, as well as from various commercially available kits in the field.

In an alternative embodiment, said method comprises culturing a strain according to the invention under conditions permitting expression and preferably secretion of the protein or polypeptide or precursor thereof and recovering the subsequently produced polypeptide and optionally subjecting the precursor to additional isolation and purification steps to obtain the polypeptide of interest. Such a method may suitably comprise a cleavage step of the precursor into the polypeptide or precursor of interest. The cleavage step can be cleavage with a Kex-2 like protease, any basic amino acid paired protease or Kex-2 for example when a protease cleavage site links a well secreted protein carrier and the polypeptide of interest. A person skilled in the art can readily find Kex-2-like protease sequences as consensus sequence details for such are available and a number of alternatives have already been disclosed e.g. furin.

Suitably in a method for production of the polypeptide according to any of the embodiments of the invention the cultivation occurs at pH higher than 5, preferably 5-10, more preferably 6-9. Suitably in such a method the cultivation occurs at a temperature between 25-43° C., preferably 30-40° C. The *Chrysosporium* strain used in the method according to the invention is quite suitably a recombinant *Chrysosporium* strain according to any of the embodiments disclosed. The method according to the invention in such a case can further be preceded by the step of production of a recombinant *Chrysosporium* strain according to the invention. The selection of the appropriate conditions will depend on the nature of the polypeptide to be expressed and such selection lies well within the realm of normal activity of a person skilled in the art.

The method of production of a recombinant *Chrysosporium* strain according to the invention is also part of the subject invention. The method comprises stably introducing a nucleic acid sequence encoding a heterologous or homologous polypeptide into a *Chrysosporium* strain, said nucleic acid sequence being operably linked to an expression regulating region, said introduction occurring in a manner known per se for transforming filamentous fungi. As stated above numerous references hereof are available and a small selection has been cited. The information provided is sufficient to enable the skilled person to carry out the method without undue burden. The method comprises introduction of a nucleic acid sequence comprising any of the nucleic acid elements described in the various embodiments of the recombinant *Chrysosporium* according to the invention as such or in combination.

By way of example the introduction can occur using the protoplast transformation method. The method is described in the examples. Alternative protoplast or spheroplast transformation methods are known and can be used as have been described in the prior art for other filamentous fungi. Details of such methods can be found in many of the cited references and are thus incorporated by reference. A method according to the invention suitably comprises using a non-recombinant strain of *Chrysosporium* according to the invention as starting material for introduction of the desired sequence encoding the polypeptide of interest.

The subject invention also covers a method of producing *Chrysosporium* enzyme, said method comprising culturing a *Chrysosporium* strain according to any of the embodiments of the invention as described above in or on a cultivation medium at pH higher than 5, preferably 5-10, more preferably 6-9, suitably 6-7.5, 7.5-9 as examples of neutral and alkaline pH ranges.

The subject invention also covers such a method using a cultivation medium at a temperature between 25-43° C., preferably 30-40° C. The combination of preferred pH and temperature is an especially preferred embodiment of the method of producing *Chrysosporium* enzyme according to the invention.

More in general the invention further covers a method of producing enzymes exhibiting neutral or alkaline optimal activity and/or stability, preferably alkaline optimal activity and/or stability. The preferred ranges vis-à-vis pH and optimal activity as well as assays with which to determine such have been provided elsewhere in the description. The enzyme should be selected from carbohydrate-degrading enzymes, proteases, other hydrolases, oxidoreductases, and transferases, as described above, said method comprising cultivating a host cell transformed or transfected with the corresponding enzyme-encoding nucleic acid sequence. Suitably such an enzyme will be a *Chrysosporium* enzyme. A suitable method such as this comprises production specifically of cellulase, xylanase, pectinase, lipase and protease, wherein cellulase and xylanase cleave β-1,4-bonds and cellulase comprises endoglucanase, cellobiohydrolase and β-glucosidase. The method according to the invention can comprise cultivating any *Chrysosporium* host according to the invention comprising nucleic acid encoding such aforementioned enzymes. Suitably the production of non-recombinant *Chrysosporium* hosts according to the invention is directed at production of carbohydrate degrading enzymes, hydrolases and proteases. In such a case the enzyme is suitably other than a cellulase. Suitable examples of products to be produced are given in Tables A and B. Methods of isolating are analogous to those described in WO 98/15633 and are incorporated by reference.

The enzymes produced by *Chrysosporium* strains according to the invention are also covered by the invention. Enzymes of *Chrysosporium* origin as can be isolated from non-recombinant *Chrysosporium* strains according to the invention are also covered. They exhibit the aforementioned stability, activity characteristics. Suitably they are stable in the presence of LAS. In particular proteases with pI 4-9.5, proteases with a MW of 25-95 kD, xylanases with pI between 4.0 and 9.5, xylanases with MW between 25 and 65 kD, endoglucanases with a pI between 3.5 and 6.5, endoglucanases with MW of 25-55 kDa, β-glucosidases, α,β-galactosidases with a pI of 4-4.5, β-glucosidases, α,β-galactosidases with a MW of 45-50 kDa, cellobiohydrolases of pI 4-5, cellobiohydrolases of MW 45-75 kDa, e.g. a MW of 55 kD and pI 4.4, polygalacturonases, with a pI of 4.0-5.0 polygalacturonase of 60-70 kDa, e.g. 65 kDa, esterases with a pI 4-5, and esterases with a MW of 95-105 kDa with the afore-mentioned stability, activity characteristics are claimed. The molecular weights (MW) are those determined by SDS-PAGE. The non-recombinant i.e. natively occurring enzyme is other than cellulase as disclosed in WO 98/15633. An enzyme as disclosed in WO 98/15633 is excluded. Enzymes according to the invention are represented by the enzymes of Table B. Enzymes with combinations of the pI values and molecular weights mentioned above are also covered.

The invention is also concerned with the (over)production of non-protein products by the mutant (recombinant) strains of the invention. Such non-protein products include primary metabolites such as organic acids, amino acids, and secondary metabolites such as antibiotics, e.g. penicillins and cephalosporins, and other therapeutics. These products are the result of combinations of biochemical pathways, involving several fungal genes of interest. Fungal primary and secondary metabolites and procedures for producing these metabolites in fungal organisms are well known in the art. Examples of the production of primary metabolites have been described by Mattey M., The Production of Organic Acids, *Current Reviews in Biotechnology*, 12, 87-132 (1992). Examples of the production of secondary metabolites have been described by Penalva et al. The Optimization of Penicillin Biosynthesis in Fungi, *Trends in Biotechnology* 16, 483-489 (1998).

EXAMPLES

Examples of Biomass and Viscosity Determinations

The following operating parameter data ranges have been determined for fungal fermentations using three different fungal organisms. The three fungal organisms compared are: *Trichoderma longibrachiatum* (formerly *T. reesei*), *Aspergillus niger* and *Chrysosporium lucknowense* (UV18-25).

Viscosity:

Viscosity is determined on a Brookfield LVF viscometer using the small sample adapter and spindle number 31.

Turn the water-circulating pump on 5 minutes prior to viscometer use to equilibrate the water jacket. The water bath temperature should be 30° C.

Obtain a fresh sample of fermentation broth and place 10 ml of the broth in the small sample spindle. Select the spindle speed to give a reading in the range 10-80. Wait four (4) minutes and take the reading from the viscometer scale. Multiply the reading by the factor given below to get the viscosity in centipoise (cP).

| Spindle Speed | Multiplication Factor |
|---|---|
| 6 | 50 |
| 12 | 25 |
| 30 | 10 |
| 60 | 5 |

The following viscosity ranges have been determined for fermentations using the specified fungal organism using the above procedure:

|  | Viscosity in cP |
|---|---|
| *T. longibrachiatum* | 200-600 |
| *A. niger* | 1,500-2,000 |
| *C. lucknowense* (UV18-25) | LT 10 |

Biomass:

Biomass is determined by the following procedure:

Preweigh 5.5 cm filter paper (Whatman 54) in an aluminium weighing dish.

Filter 5.0 ml whole broth through the 5.5 cm paper on a Buchner funnel, wash the filter cake with 10 ml deionised water, place the washed cake and filter in a weighing pan and dry overnight at 60° C.

Finish drying at 100° C. for 1 hour, then place in desiccator to cool.

Measure the weight of dried material. Total biomass (g/l) is equal to the difference between the initial and finals weights multiplied by 200. The following biomass ranges have been determined for fermentations using the specified fungal organism using the above procedure:

|  | Biomass in g/l |
|---|---|
| *T. longibrachiatum* | 2.5-5 |
| *A. niger* | 5-10 |
| *C. lucknowense* (UV18-25) | 0.5-1 |

Protein:

Protein levels were determined using the BioRad Bradford Assay Procedure from BioRad Laboratories. Protein levels were highest for the *Chrysosporium*.

The data presented above represent values determined 48 hours into the fermentation process until fermentation end; All values of *Aspergilli* and *Trichoderma* are for commercially relevant fungal organisms and reflect actual commercial data.

A fungal strain such as *C. lucknowense* (UV18-25) has the advantage that the low viscosity permits the use of lower power input and/or shear in the fermentation to meet oxygen demands for those cases where shear stress on the product may be detrimental to productivity due to physical damage of the product molecule. The lower biomass production at high protein production indicates a more efficient organism in the conversion of fermentation media to product. Thus the *Chrysosporium* provides better biomass and viscosity data whilst also delivering at least as much protein, and in fact a lot more protein than the two commercially used systems which obviously are better than for typically deposited *Aspergillus* or *Trichoderma reesei* strains in general public collections.

The high protein production with low biomass concentration produced by *C. lucknowense* (UV18-25) would allow development of fermentation conditions with higher multiples of increase in biomass, if increasing biomass results in increased productivity, for the desired product before reaching limiting fermentation conditions. The present high levels of biomass and viscosity produced by the *T. longibrachiatum* and *A. niger* organisms restrict the increase of biomass as the present levels of biomass and viscosity are near limiting practical fermentation conditions.

Examples of Transformation Comparing *Chrysosporium*, *Trichoderma* and *Tolypocladium* Geodes Two untransformed *Chrysosporium* C1 strains and one *Trichoderma reesei* reference strain were tested on two media (Gs pH 6.8 and Pridham agar, PA, pH 6,8). To test the antibiotic resistance level spores were collected from 7 day old PDA plates. Selective plates were incubated at 32° C. and scored after 2, 4, and 5 days. It followed that the C-1 strains NG7C-19 and UV18-25 clearly have a low basal resistance level both to phleomycin and hygromycin. This level is comparable to that for a reference *T. reesei* commonly used laboratory strain. Thus there is clear indication these two standard fungal selectable markers can be used well in *Chrysosporium* strains. Problems with other standard fungal selectable markers should not be expected.

Selection of Sh-ble (phleomycin-resistance) transformed *Chrysosporium* strains was successfully carried out at 50 μg/ml. This was also the selection level used for *T. reesei* thus showing that differential selection can be easily achieved in *Chrysosporium*. The same comments are valid for transformed strains with hygromycin resistance at a level of 150 μg/ml.

TABLE C

| | Gs (pH 6.8) | | | Pridham Agar (PA, pH 6.8) | | |
|---|---|---|---|---|---|---|
| | NG7C-19 | UV18-25 | T.r.11D5 | NG7C-19 | UV18-25 | T.r.11D5 |
| Phleomycin | 7.5 μg/ml | 10 μg/ml | 5-7.5 μg/ml | 2.5 μg/ml | 10 μg/ml | 2.5 μg/ml |
| Hygromycin | 7.5-10 μg/ml | 10 μg/ml | 10 μg/ml | 15 μg/ml | 25 μg/ml | 15 μg/ml |

TABLE D

Transformation efficiency (using 10 μg of reference plasmid pAN8-1)

| | T. reesei | NG7C-19 | UV18-25 |
|---|---|---|---|
| Viability | 106/200 μl | 5 × 106/200 μl | 5 × 106/200 μl |
| Transformants Per 200 μl | 2500 | 104 | 104 |
| Transformants per 106 viable cells | 2500 | 2000 | 2000 |

The results show that the *Chrysosporium* transformants viability is superior to that of *Trichoderma*. The transformability of the strains is comparable and thus the number of transformants obtained in one experiment lies 4 times higher for *Chrysosporium* than for *T. reesei*. Thus the *Chrysosporium* transformation system not only equals the commonly used *T. reesei* system, but even outperforms it. This improvement can prove especially useful for vectors that are less transformation efficient than pAN8-1. Examples of such less efficient transformation vectors are protein carrier vectors for production of non-fungal proteins which generally yield 10 times fewer transformants.

A number of other transformation and expression vectors were constructed with homologous *Chrysosporium* protein encoding sequences and also with heterologous protein encoding sequences for use in transformation experiments with *Chrysosporium*. The vector maps are provided in the FIGS. 6-11.

The homologous protein to be expressed was selected from the group of cellulases produced by *Chrysosporium* and consisted of endoglucanase 6 which belongs to family 6 (MW 43

The protoplast transformation technique was used on *Chrysosporium* based on the most generally applied fungal transformation technology. All spores from one 90 mm PDA plate were recovered in 8 ml IC1 and transferred into a shake flask of 50 ml IC1 medium for incubation for 15 hours at 35° C. and 200 rpm. After this the culture was centrifuged, the pellet was washed in MnP, brought back into solution in 10 ml MnP and 10 mg/ml Caylase $C_3$ and incubated for 30 minutes at 35° C. with agitation (150 rpm).

The solution was filtered and the filtrate was subjected to centrifugation for 10 minutes at 3500 rpm. The pellet was washed with 10 ml MnPCa$^{2+}$. This was centrifuged for 10 minutes at 25° C. Then 50 microliters of cold MPC was added. The mixture was kept on ice for 30 minutes whereupon 2.5 ml PMC was added. After 15 minutes at room temperature 500 microliters of the treated protoplasts were mixed to 3 ml of MnR Soft and immediately plated out on a MnR plate containing phleomycin or hygromycin as selection agent. After incubation for five days at 30° C. transformants were analysed (clones become visible after 48 hours). Transformation efficiency was determined using 10 microgrammes of reference plasmid pAN8-1[19]. The results are presented in the following Table D.

kDa) and the heterologous protein was endoglucanase 3 which belongs to family 12 (MW 25 kDa) of *Penicillium*.

pF6g comprises *Chrysosporium* endoglucanase 6 promoter fragment linked to endoglucanase 6 signal sequence in frame with the endoglucanase 6 open reading frame followed by the endoglucanase 6 terminator sequence. Transformant selection is carried out by using cotransformation with a selectable vector.

pUT1150 comprises *Trichoderma reesei* cellobiohydrolase promoter linked to endoglucanase 6 signal sequence in frame with the endoglucanase 6 open reading frame followed by the *T. reesei* cellobiohydrolase terminator sequence. In addition this vector carries a second expression cassette with a selection marker i.e. the phleomycin resistance gene (Sh-ble gene).

pUT1152 comprises *Aspergillus nidulans* glyceraldehyde-3-phosphate dehydrogenase A promoter linked to endoglucanase 6 signal sequence in frame with the endoglucanase 6 open reading frame followed by the *A. nidulans* anthranilate synthase (trpC) terminator sequence. In addition this vector carries a second expression cassette with a selection marker i.e. the phleomycin resistance gene (Sh-ble gene).

pUT1155 comprises *A. nidulans* glyceraldehyde-3-phosphate dehydrogenase A promoter linked to *Trichoderma* reesei cellobiohydrolase signal sequence in frame with the carrier protein Sh-ble which in turn is linked in frame to the endoglucanase 6 open reading frame followed by the *A. nidulans* trpC terminator sequence. This vector uses the technology of the carrier protein fused to the protein of interest which is known to very much improve the secretion of the protein of interest.

pUT1160 comprises *Aspergillus nidulans* glyceraldehyde-3-phosphate dehydrogenase A promoter linked to *Trichoderma reesei* cellobiohydrolase signal sequence in frame with the carrier protein Sh-ble which in turn is linked in frame to the endoglucanase 3 open reading frame of *Penicillium* followed by the *A. nidulans* trpC terminator sequence.

pUT1162 comprises *Trichoderma reesei* cellobiohydrolase promoter linked to endoglucanase 3 signal sequence in frame with the endoglucanase 3 open reading frame of *Penicillium* followed by the *T. reesei* cellobiohydrolase terminator sequence. In addition this vector carries a second expression cassette with a selection marker i.e. the phleomycin resistance gene (Sh-ble gene).

Further examples of expression systems include a *Chrysosporium* endoglucanase 3 promoter fragment linked to endoglucanase 3 signal sequence in frame with the endoglucanase 3 open reading frame followed by the endoglucanase 3 terminator sequence. Transformant selection is carried out by using cotransformation with a selectable vector.

Another example is a *Chrysosporium lucknowense* cellobiohydrolase promoter linked to *Penicillium* endoglucanase 3 signal sequence in frame with the *Penicillium* endoglucanase 3 open reading frame followed by the *Chrysosporium* cellobiohydrolase terminator sequence. In addition this vector carries a second expression cassette with a selection marker i.e. the aceetamidase S gene (AmdS gene).

A further example comprises *Chrysosporium* glyceraldehyde-3-phosphate dehydrogenase 1 promoter linked to the *Aspergillus niger* glucoamylase signal sequence and the glucoamylase open reading frame fused to the human Interleukine 6 open reading frame. In addition this vector carries a second expression cassette with a selection marker i.e. the AmdS gene.

A still further example is a *Aspergillus nidulans* glyceraldehyde-3-phosphate dehydrogenase A promoter linked to the endoglucanase 5 open reading frame followed by a *Aspergillus nidulans* terminator sequence.

TABLE E

Comparative transformations

| Vector | Strain | Transformation | No of transf. | Tested in liquid culture |
|---|---|---|---|---|
| pUT1150 | UV18-25 | selection phleo | 285 | 5 |
|  | T. geodes | selection phleo | 144 | 5 |
| pUT1152 | UV18-25 | cotransformation pAN8.1 | 398 | 5 |
|  | T. geodes | cotransformation pAN8.1 | 45 | 4 |
| pF6g | UV18-25 | cotransformation pAN8.1 | 252 | 6 |
|  | T. geodes | cotransformation pAN8.1 | 127 | 5 |
| pUT1162 | UV18-25 | selection phleo | >400 |  |
|  | T. geodes | Not done yet |  |  |

Table E shows the results of transformation of both *Chrysosporium* UV18-25 and *Tolypocladium geodes*. The transformation protocol used is described in the section for heterologous transformation.

Examples of Heterologous and Homologous Expression of *Chrysosporium* Transformants C1 strains (NG7C-19 and/or UV18-25) have been tested for their ability to secrete various heterologous proteins: a bacterial protein (*Streptoalloteichus hindustanus* phleomycin-resistance protein, Sh ble), a fungal protein (*Trichoderma reesei* xylanase II, XYN2) and a human protein (the human lysozyme, HLZ).

The details of the process are as follows:

[1] C1 Secretion of *Streptoalloteichus hindustanus* Phleomycin-Resistance Protein (Sh ble).

C1 strains NG7C-19 and UV18-25 have been transformed by the plasmid pUT720[1]. This vector presents the following fungal expression cassette:

*Aspergillus nidulans*_glyceraldehyde-3-phosphate dehydrogenase (gpdA) promoter[2]

A synthetic *Trichoderma reesei* cellobiohydrolase I (cbh1) signal sequence[1,3]

*Streptoalloteichus hindustanus* phleomycin-resistance gene Sh ble[4]

*Aspergillus nidulans* tryptophan-synthase (trpC) terminator[5]

Figure 2:
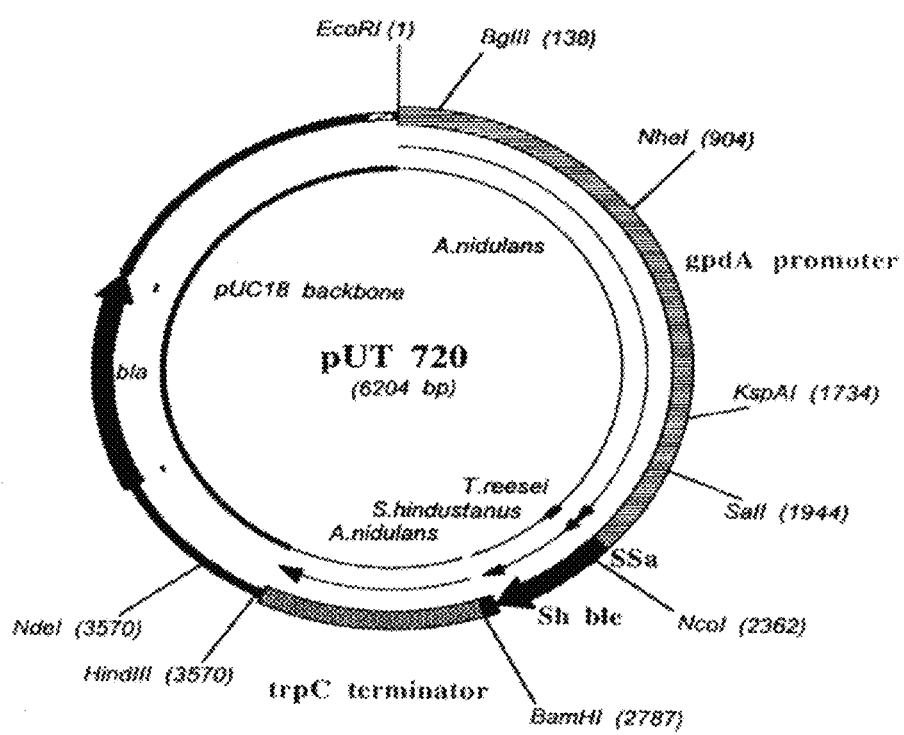
FIG. 2 is a pUT720 map

The vector also carries the beta-lactamase gene (bla) and *E. coli* replication origin from plasmid pUC18[6]. The detailed plasmid map is provided in FIG. 2.

C1 protoplasts were transformed according to Durand et al.[7] adapted to C1 (media & solutions composition is given elsewhere): All spores from one 90 mm PDA plate of untransformed C1 strain were recovered in 8 ml IC1 and transferred into a shake flask with 50 ml IC1 medium for incubation 15 hours at 35° C. and 150 rpm. Thereupon, the culture was spun down, the pellet washed in MnP, resolved in 10 ml MnP+10 mg/ml Caylase $C_3$, and incubated 30 min at 35° C. with agitation (150 rpm). The solution was filtered and the filtrate was centrifuged 10 min at 3500 rpm. The pellet was washed with 10 ml $MnPCa^{2+}$. This was spun down 10 min at 3500 rpm and the pellet was taken up into 1 ml $MnPCa^{2+}$. 10 µg of pUT720 DNA were added to 200 µl of protoplast solution and incubated 10 min at room temperature (~20° C.). Then, 50 µl of cold MPC was added. The mixture was kept on ice for 30 min whereupon 2.5 ml PMC was added. After 15 min at room temperature 500 µl of the treated protoplasts were mixed to 3 ml of MnR Soft and immediately plated out on a MnR plate containing phleomycin (50 µg/ml at pH6.5) as selection agent. After 5 days incubation at 30° C., transformants were analysed (clones start to be visible after 48 hours).

The Sh ble production of C1 transformants (phleomycin-resistant clones) was analysed as follows: Primary transformants were toothpicked to GS+phleomycin (5 µg/ml) plates and grown for 5 days at 32° C. for resistance verification. Each validated resistant clone was subcloned onto GS plates. Two subclones per transformant were used to inoculate PDA plates in order to get spores for liquid culture initiation. The liquid cultures in IC1 were grown 5 days at 27° C. (shaking 200 rpm). Then, the cultures were centrifuged (5000 g, 10 min.) and 500 µl of supernatant were collected. From these samples, the proteins were precipitated with TCA and resuspended in Western Sample Buffer to 4 mg/ml of total proteins (Lowry Method[8]). 10 µl (about 40 µg of total proteins) were loaded on a 12% acrylamide/SDS gel and run (BioRad Mini Trans-Blot system). Western blotting was conducted according to BioRad instructions (Schleicher & Schull 0.2 µm membrane) using rabbit anti-Sh ble antiserum (Cayla Cat. Ref #ANTI-0010) as primary antibody.

The results are shown in FIG. 1 and Table F:

TABLE F

Sh ble estimated production levels in C1

| | Estimated Sh ble quantity on the Western blot | Estimated Sh ble concentration in the production media |
|---|---|---|
| Untransformed NG7C-19 | Not detectable | |
| NG7C-19::720 clone 4-1 | 25 ng | 0.25 mg/l |
| NG7C-19::720 clone 5-1 | 25 ng | 0.25 mg/l |
| NG7C-19::720 clone 2-2 | 250 ng | 2.5 mg/l |
| Untransformed UV18-25 | Not detectable | |
| UV18-25::720 clone 1-2 | 500 ng | 5 mg/l |
| UV18-25::720 clone 3-1 | 250 ng | 2.5 mg/l |

These data show that:

1) The heterologous transcription/translation signals from pUT720 are functional in *Chrysosporium*.

2) The heterologous signal sequence of pUT720 is functional in *Chrysosporium*.

3) *Chrysosporium* can be used a host for the secretion of an heterologous bacterial protein.

[2] C1 Secretion of the Human Lysozyme (HLZ).

C1 strains NG7C-19 and UV18-25 have been transformed by the plasmid pUT970G[9]. This vector presents the following fungal expression cassette:

*Aspergillus nidulans*_glyceraldehyde-3-phosphate dehydrogenase (gpdA) promoter[2]

A synthetic *Trichoderma_reesei* cellobiohydrolase I (cbh1) signal sequence[1,3]

*Streptoalloteichus hindustanus* phleomycin-resistance gene Sh ble[4] used as carrier-protein[10]

*Aspergillus niger* glucoamylase (glaA2) hinge domain cloned from plasmid pAN56-2[11,12]

A linker peptide (LGERK) featuring a KEX2-like protease cleavage site[1]

A synthetic human lysozyme gene (hlz)[10]

*Aspergillus nidulans* tryptophan-synthase (trpC) terminator[5]

Figure 3:
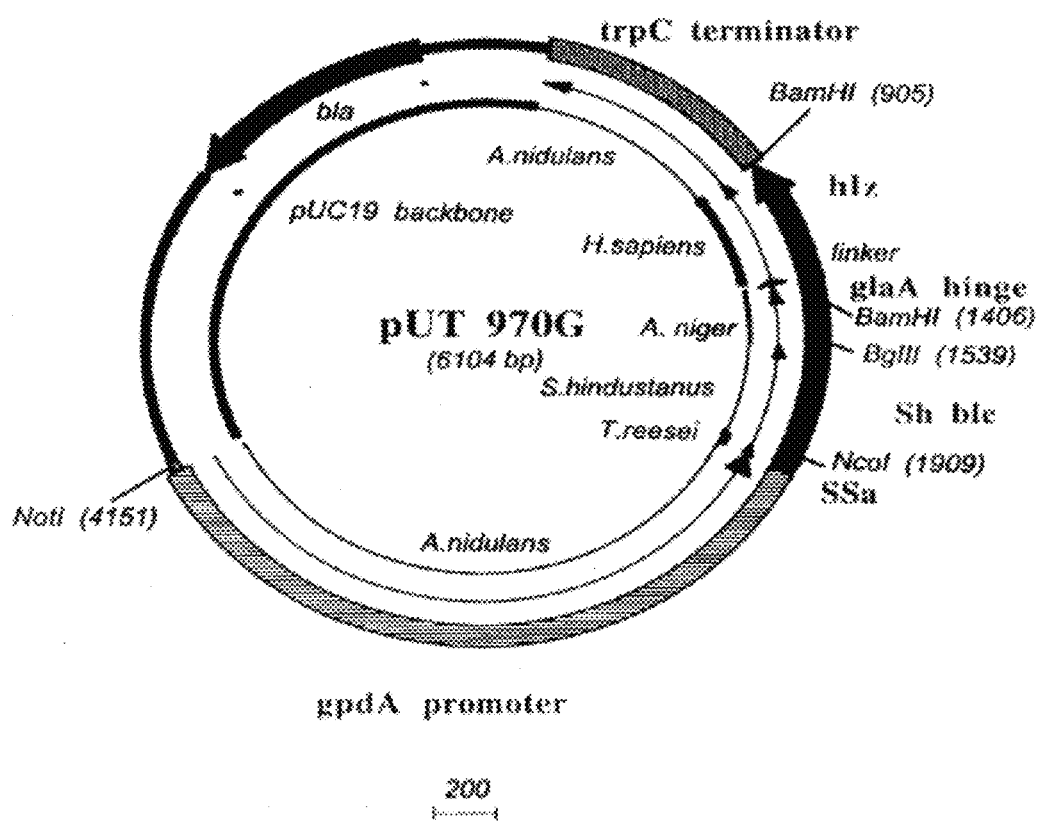
FIG. 3 is a pUT970G map

The vector also carries the beta-lactamase gene (bla) and *E. coli* replication origin from plasmid pUC18[6]. The detailed plasmid map is provided in FIG. 3.

C1 protoplasts were transformed with plasmid pUT970G following the same procedure already described in example 1. The fusion protein (Sh ble::GAM hinge::HLZ) is functional with respect to the phleomycin-resistance thus allowing easy selection of the C1 transformants. Moreover, the level of phleomycin resistance correlates roughly with the level of hlz expression.

The HLZ production of C1 transformants (phleomycin-resistant clones) was analysed by lysozyme-activity assay as follow: Primary transformants were toothpicked to GS+phleomycin (5 µg/ml) plates (resistance verification) and also on LYSO plates (HLZ activity detection by clearing zone visualisation[1, 10]). Plates were grown for 5 days at 32° C. Each validated clone was subcloned onto LYSO plates. Two subclones per transformant were used to inoculate PDA plates in order to get spores for liquid culture initiation. The liquid cultures in IC1 were grown 5 days at 27° C. (shaking 180 rpm). Then, the cultures were centrifuged (5000 g, 10 min.). From these samples, lysozyme activity was measured according to Mörsky et al.[13]

TABLE G

Active HLZ production levels in C1

| | Active HLZ concentration in culture media |
|---|---|
| Untransformed NG7C-19 | 0 mg/l |
| NG7C-19::970G clone 4 | 4 mg/l |
| NG7C-19::970G clone 5 | 11 mg/l |
| Untransformed UV18-25 | 0 mg/l |
| UV18-25::970G clone 1 | 8 mg/l |
| UV18-25::970G clone 2 | 4 mg/l |
| UV18-25::970G clone 3 | 2 mg/l |
| UV18-25::970G clone 2 | 2.5 mg/l |

These data show that:

1) Points 1 & 2 from example 1 are confirmed.

2) Sh ble is functional in *Chrysosporium* as resistance-marker.

3) Sh ble is functional in *Chrysosporium* as carrier-protein.

4) The KEX2-like protease cleavage site is functional in *Chrysosporium* (otherwise HLZ wouldn't be active).

5) *Chrysosporium* can be used as host for the secretion of a heterologous mammalian protein.

[3] C1 Secretion of *Trichoderma reesei* Xylanase II (XYN2).

C1 strain UV18-25 has been transformed by the plasmids pUT1064 and pUT1065.

pUT1064 presents the two following fungal expression cassettes:

The first cassette allows the selection of phleomycin-resistant transformants:

*Neurospora crassa*_cross-pathway control gene 1 (cpc-1) promoter[14]

*Streptoalloteichus hindustanus* phleomycin-resistance gene Sh ble[4]

*Aspergillus nidulans* tryptophan-synthase (trpC) terminator[5]

The second cassette is the xylanase production cassette:

*T. reesei*_strain TR2 cbh1 promoter[15]

*T. reesei*_strain TR2 xyn2 gene (including its signal sequence)[16]

*T. reesei*_strain TR2 cbh1 terminator[15]

Figure 4:
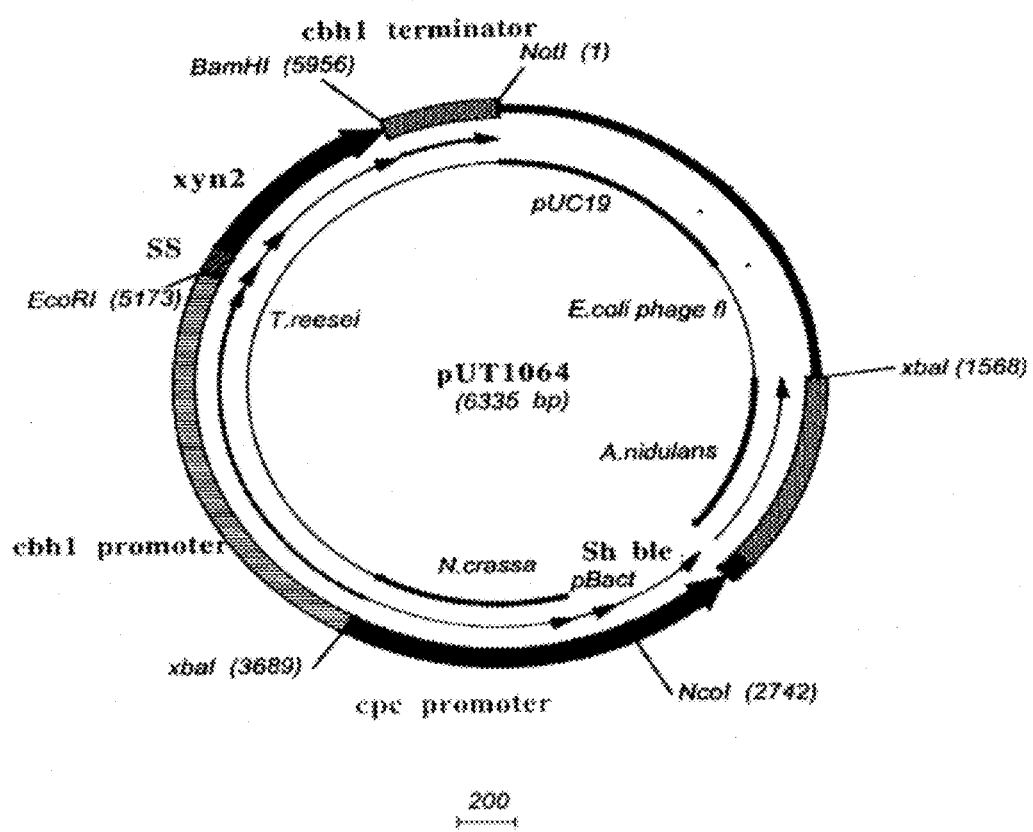
FIG. 4 is a pUT1064 map

The vector also carries an *E. coli* replication origin from plasmid pUC19[6]. The plasmid detailed map is provided in FIG. 4.

pUT1065 presents the following fungal expression cassette:

*A. nidulans*_glyceraldehyde-3-phosphate dehydrogenase (gpdA) promoter[2]

A synthetic *T._reesei* cellobiohydrolase I (cbh1) signal sequence[1,3]

*S. hindustanus* phleomycin-resistance gene Sh ble[4] used as carrier-protein[10]

A linker peptide (SGERK) featuring a KEX2-like protease cleavage site[1]

*T. reesei*_strain TR2xyn2 gene (without signal sequence)[16]

*A. nidulans* tryptophan-synthase (trpC) terminator[5]

Figure 5:
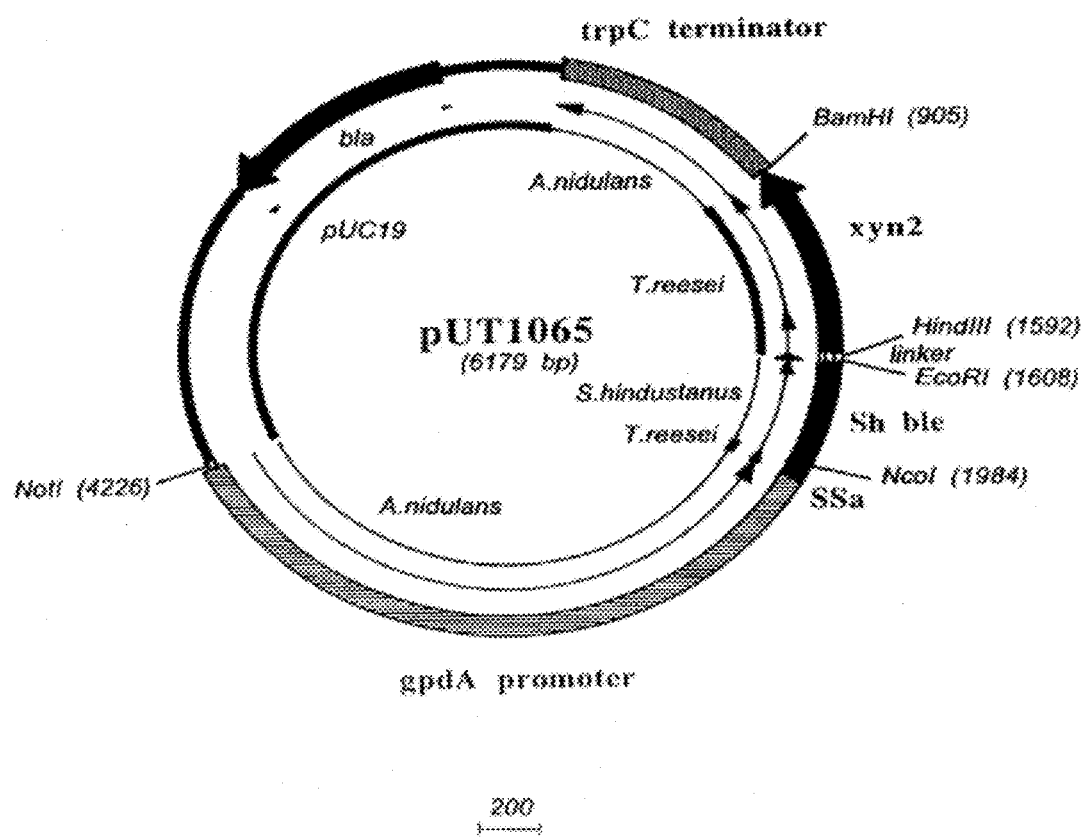
FIG. 5 is a pUT1065 map
Figure 6:
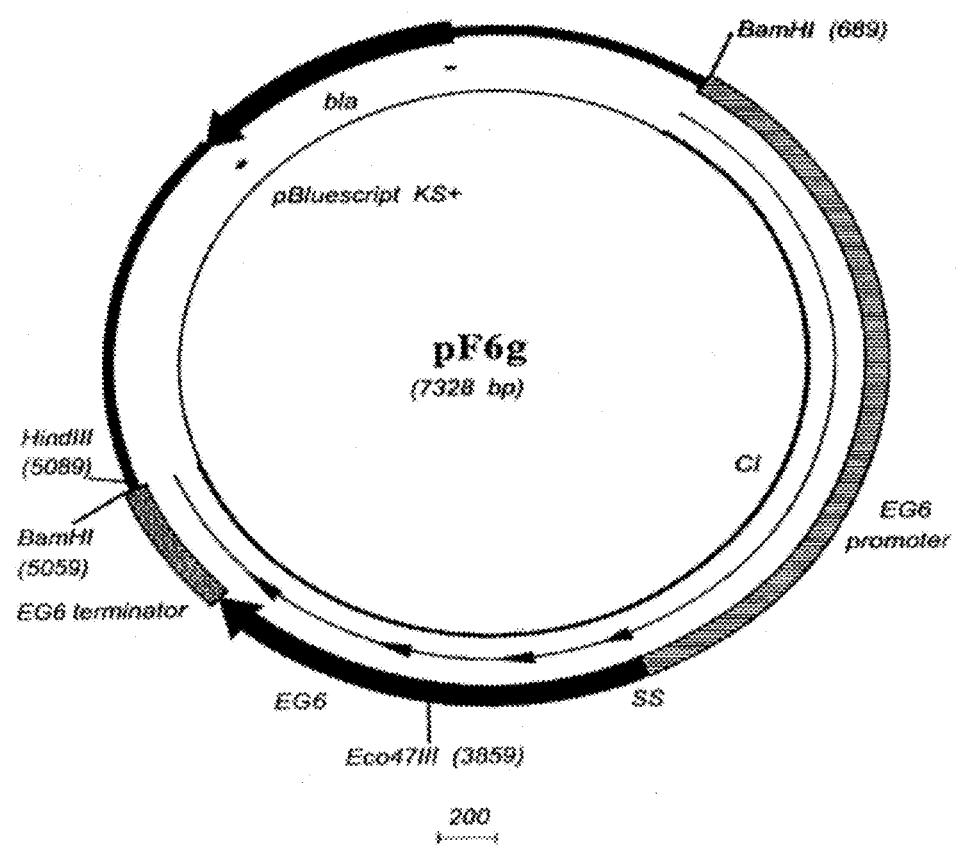
FIG. 6 is a pF6g map
Figure 7:
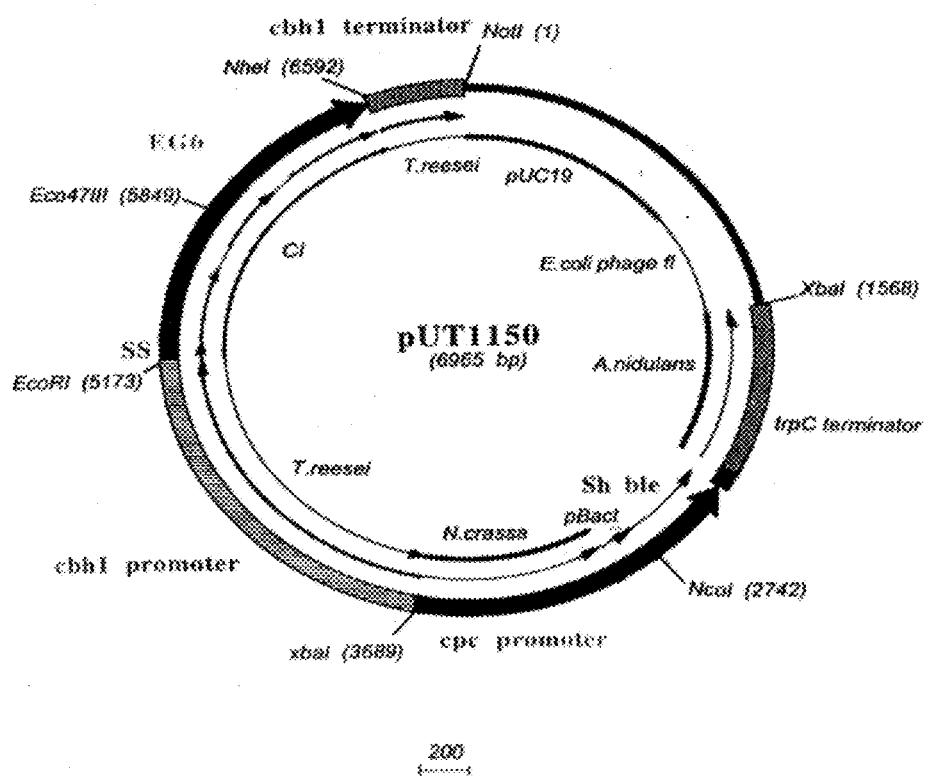
FIG. 7 is a pUT1150 map
Figure 8:
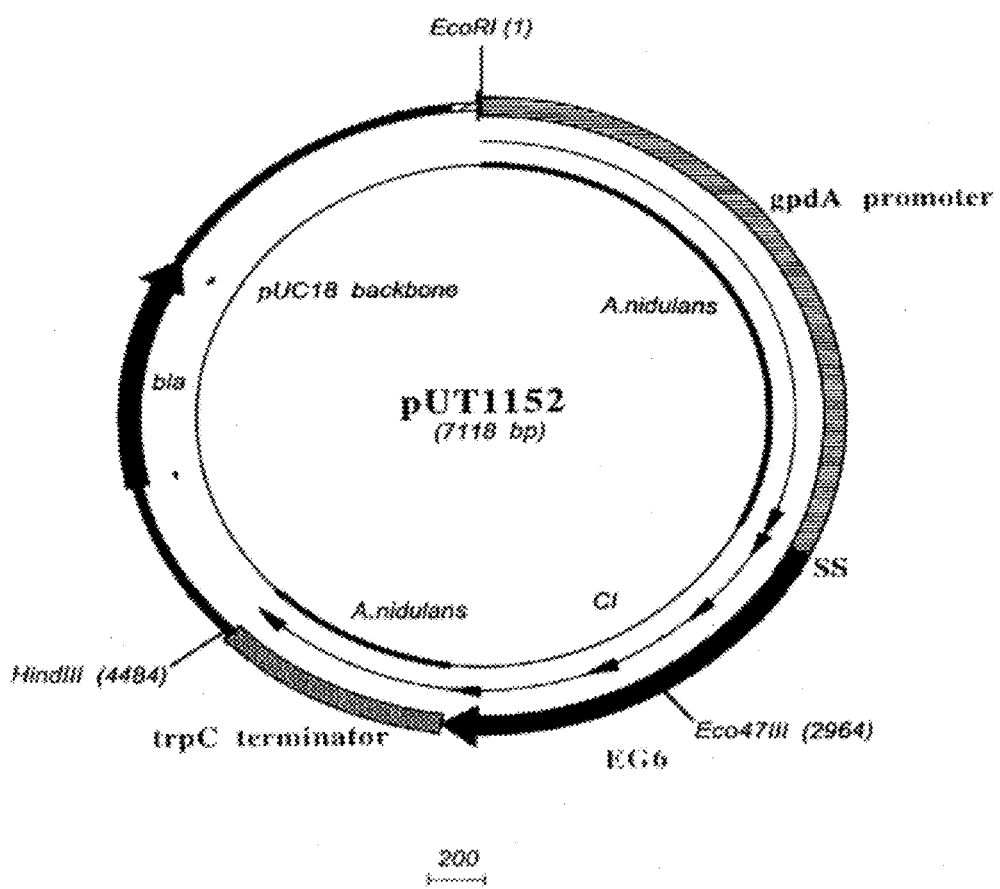
FIG. 8 is a pUT1152 map
Figure 9:
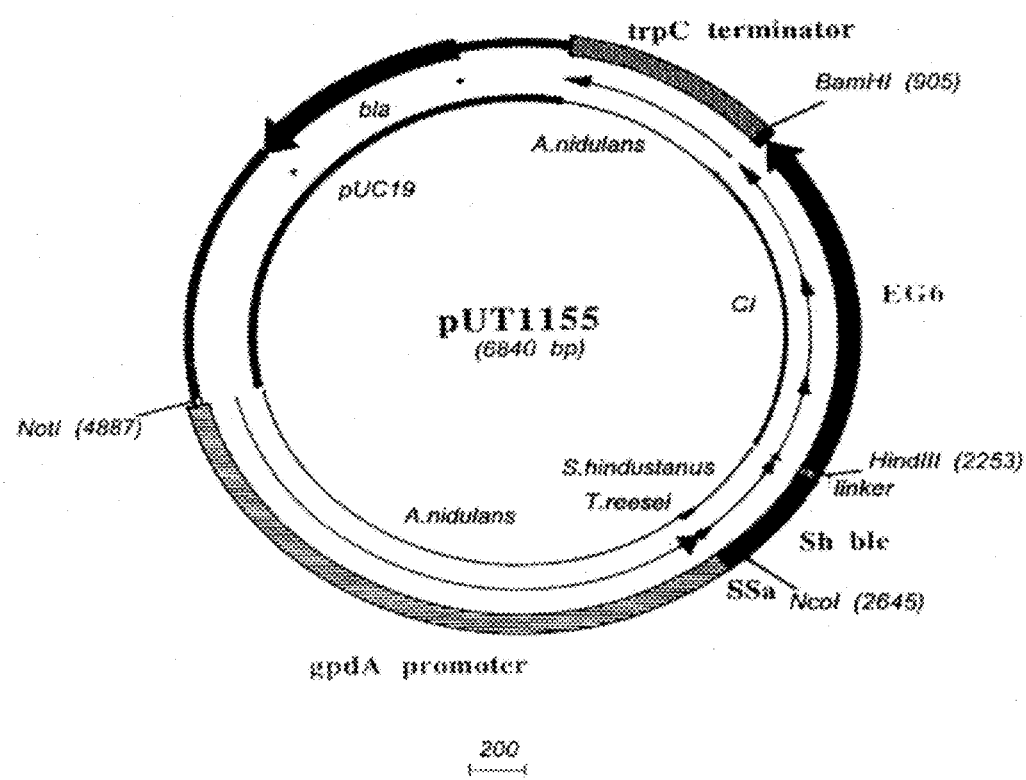
FIG. 9 is a pUT1155 map
Figure 10:
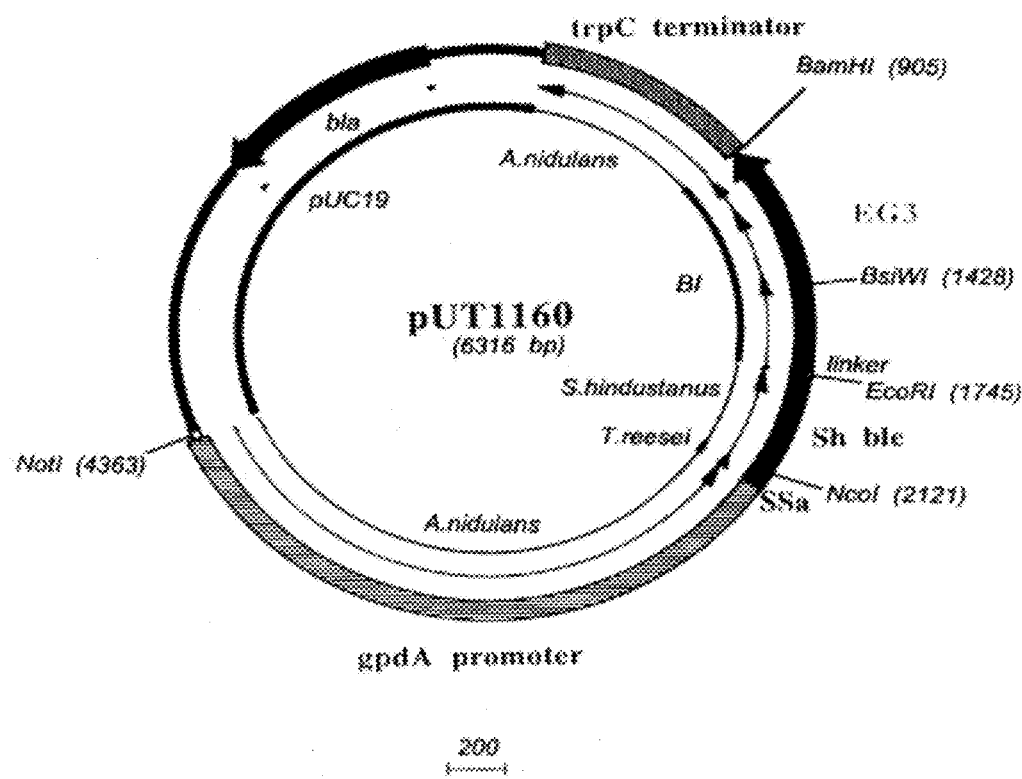
FIG. 10 is a pUT1160 map
Figure 11:
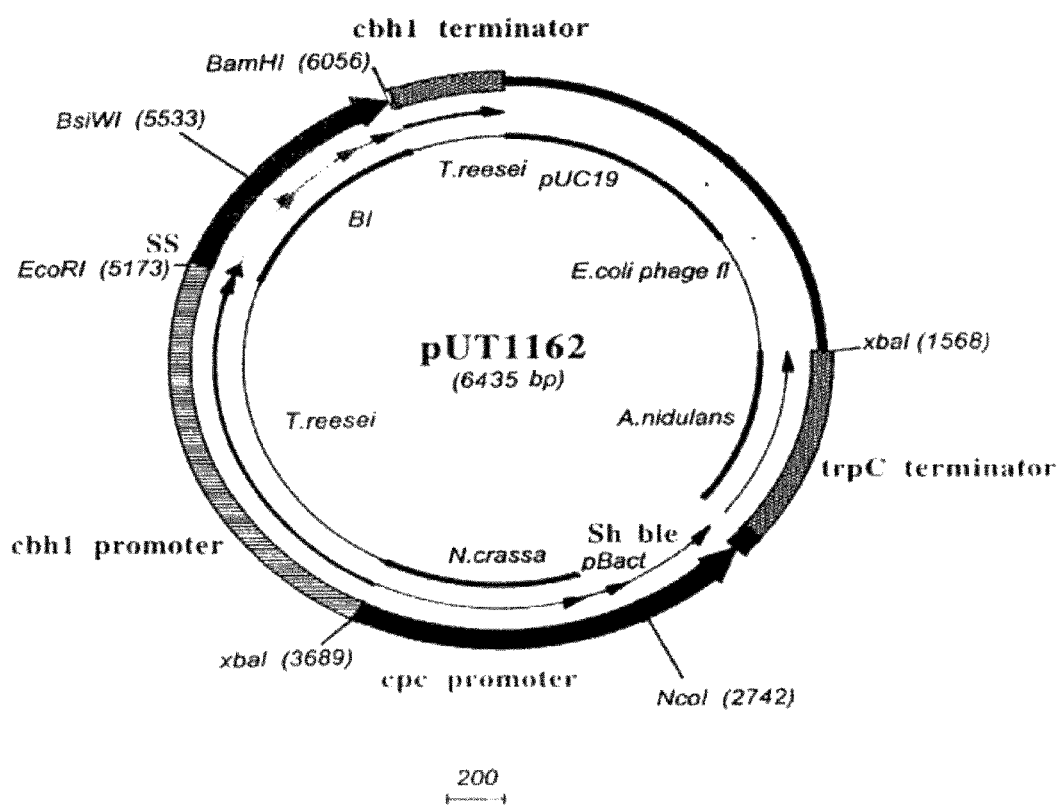
FIG. 11 is a pUT1162 map
Figure 15A:
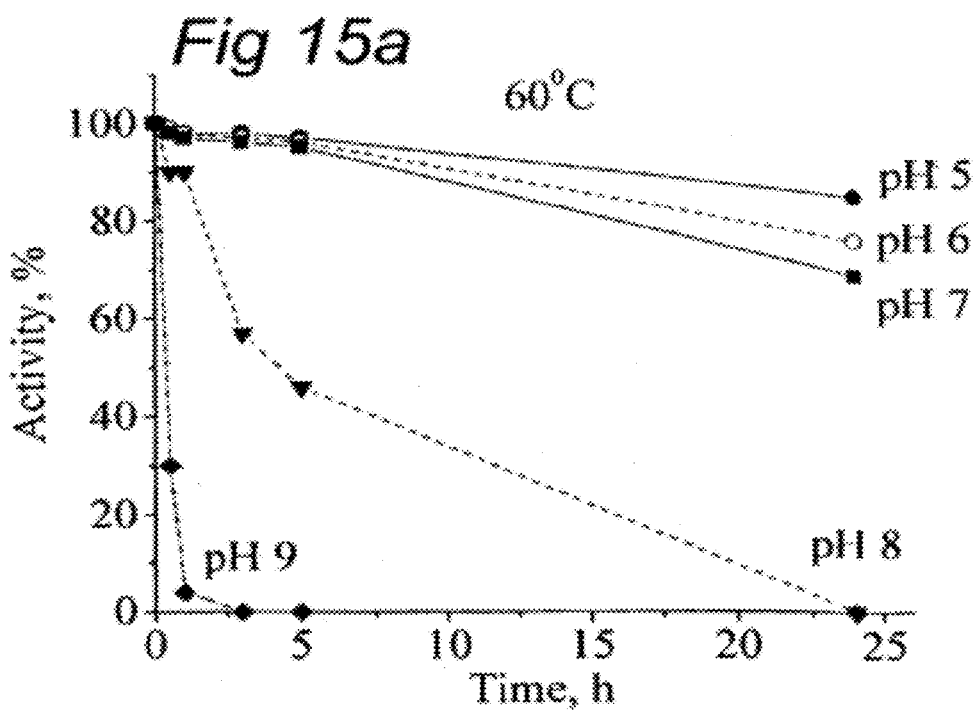
FIG. 15: pH stability at 60° C. and 50° C. of 60 kD Xyl (pI 4.7) from non-bound fraction of F-60-31 sample.
Figure 15B:
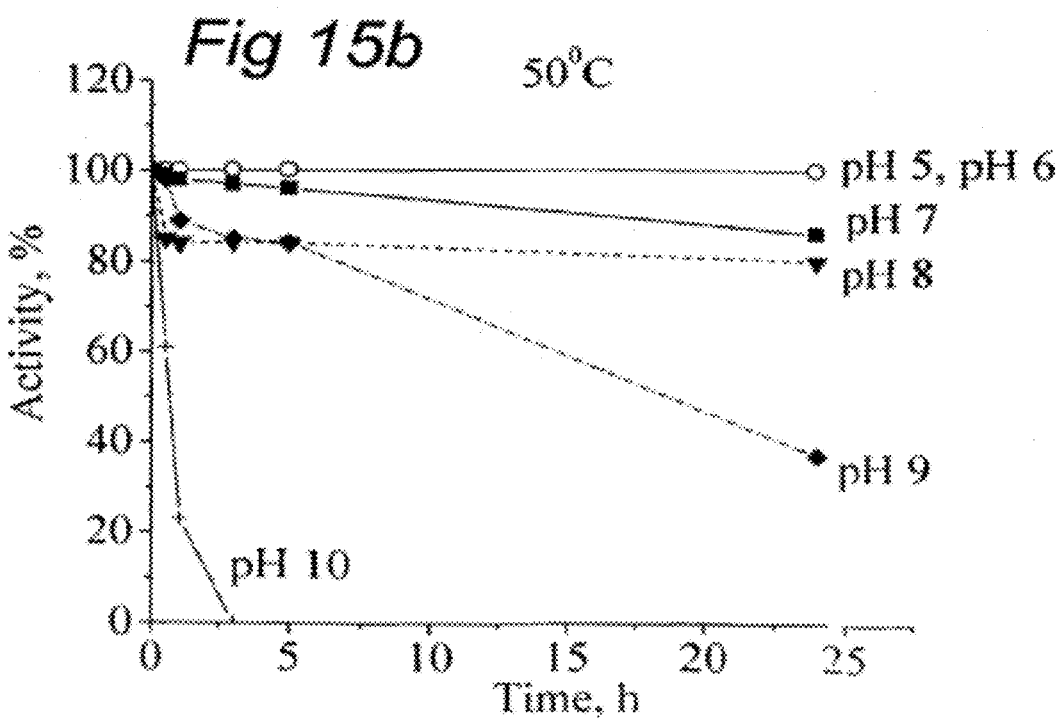
Figure 18A:
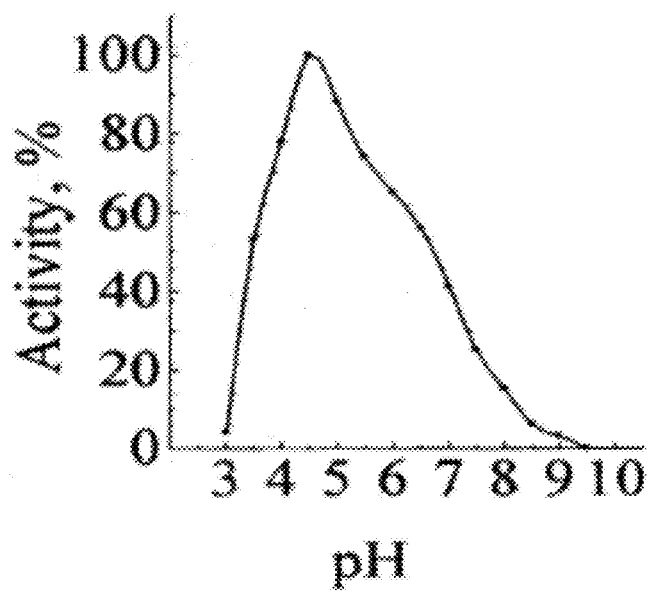
FIG. 18: pH and temperature dependencies of α-galactosidase activity of F-60-43, UF-conc.
Figure 18B:
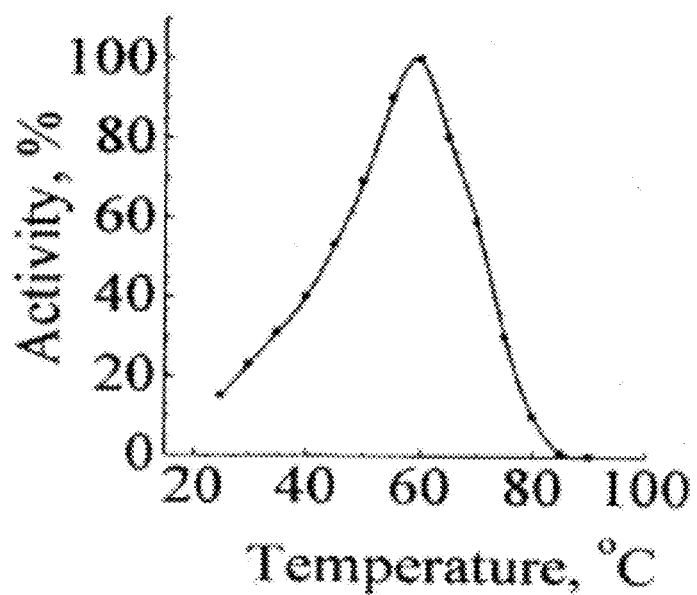
Figure 23A:
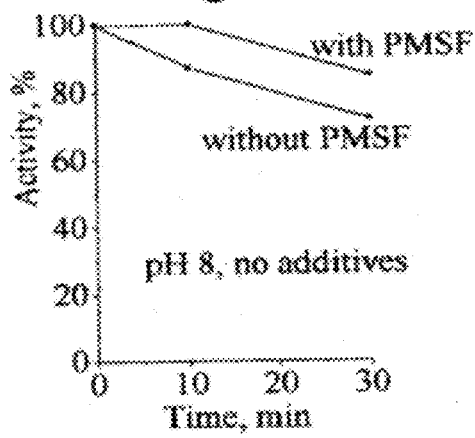
FIG. 23: Effect of 30 kD (pI 8.9) "alkaline" protease on xylanase activity of the non-bound-fraction (Macro Prep Q(™)) of F 60-31 CF at 50° C.
Figure 23B:
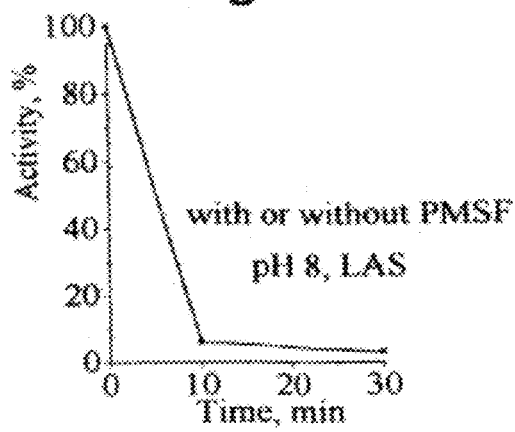
Figure 23C:
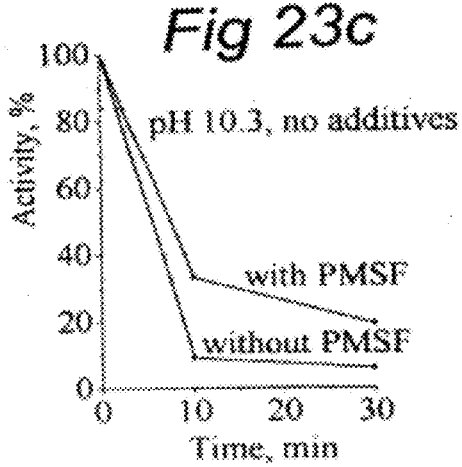
Figure 23D:
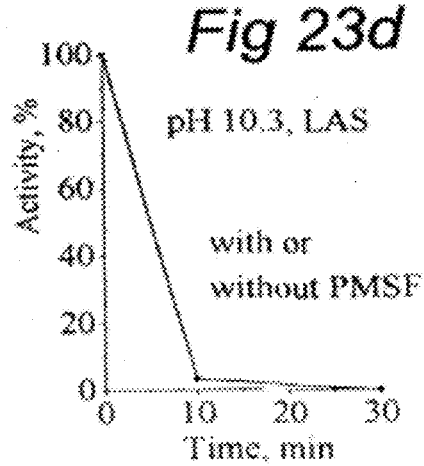
Figure 25:
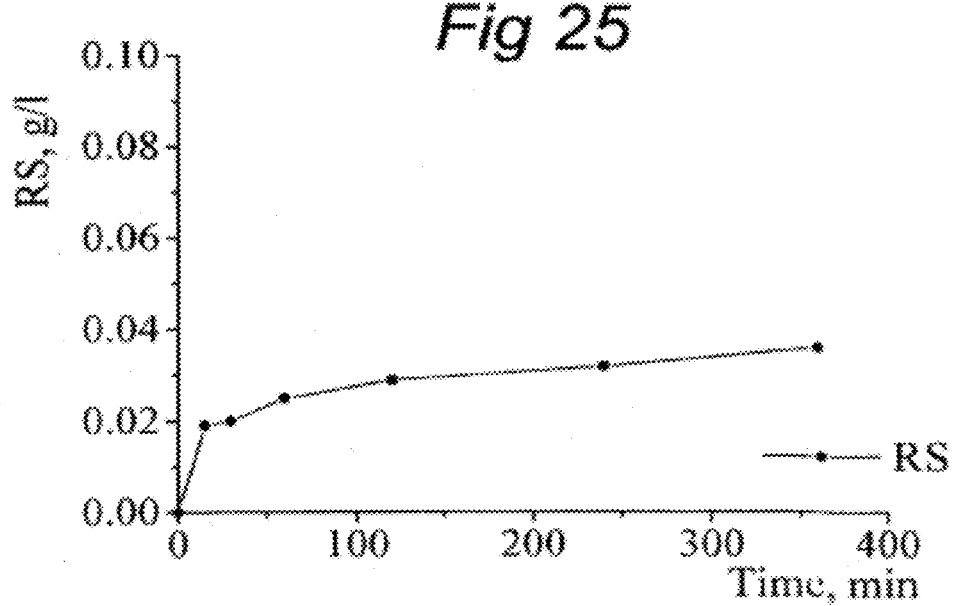
Figure 28:
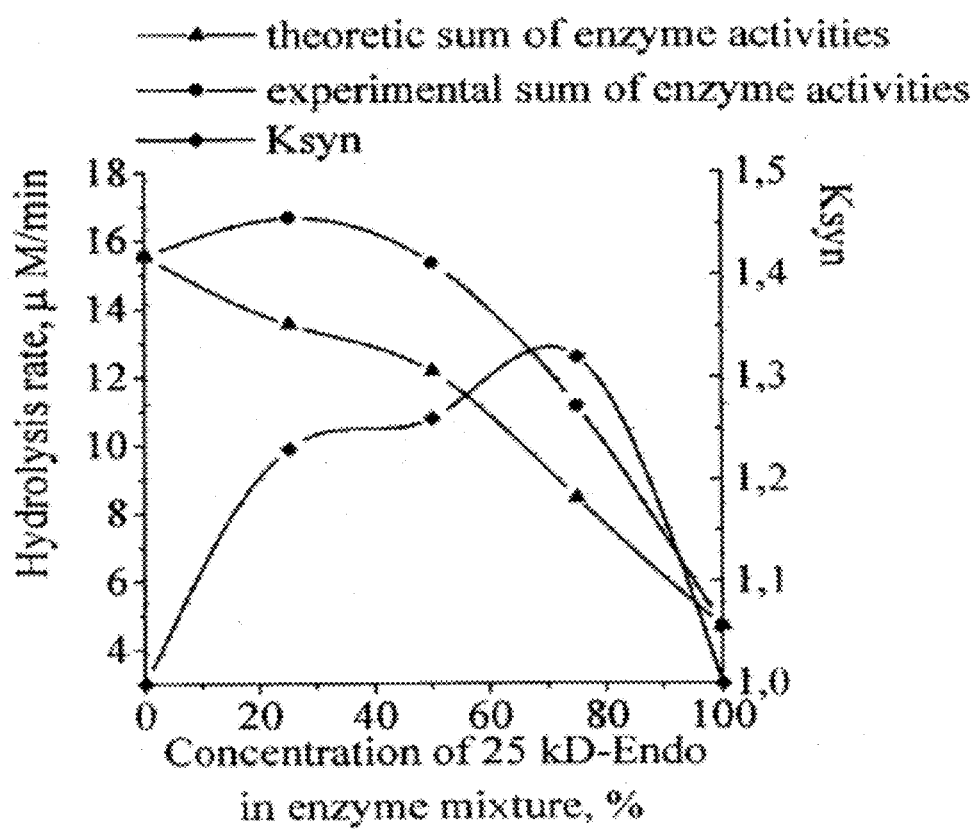
Figure 29A:
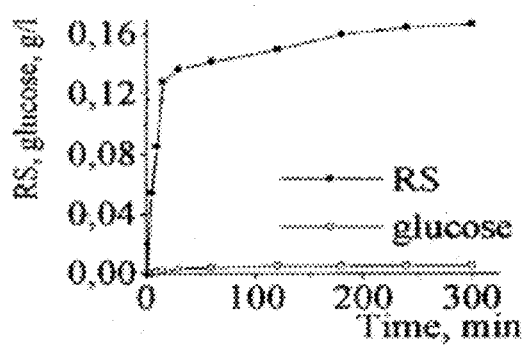
Figure 29B:
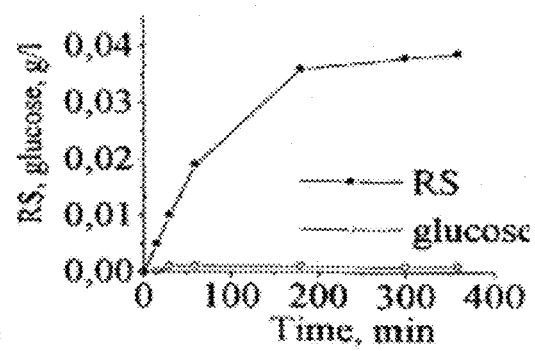
Figure 29C:
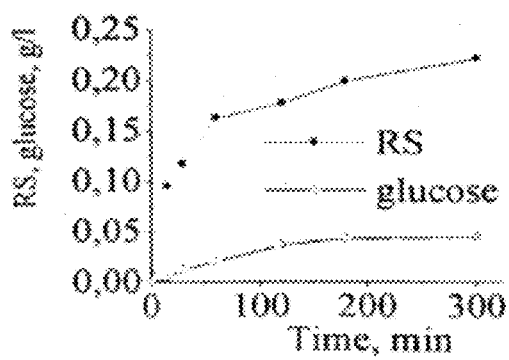
Figure 29D:
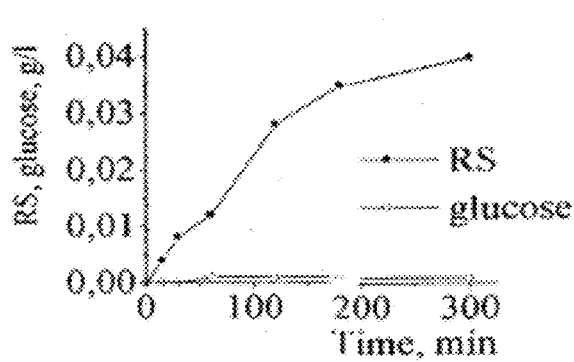
Figure 30A:
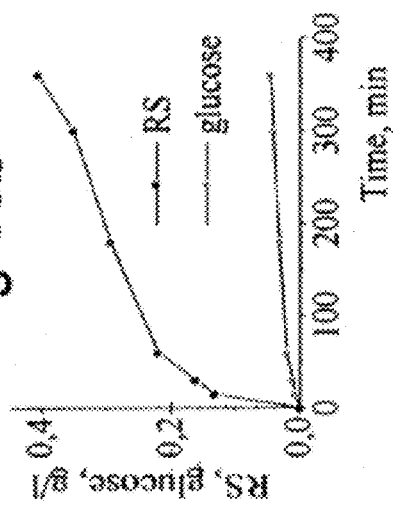
Figure 30B:
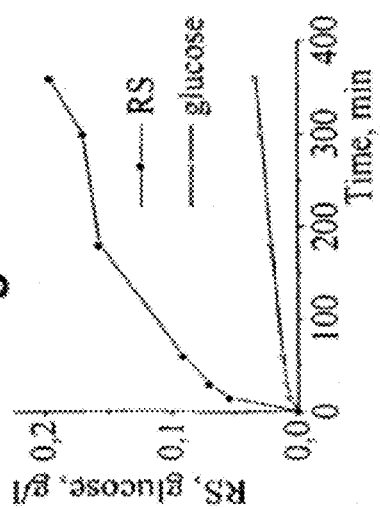
Figure 30C:
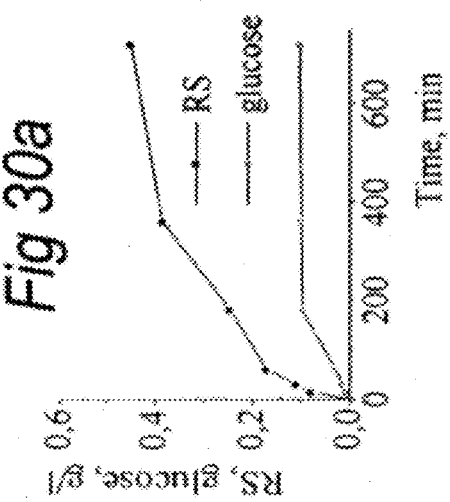
Figure 30D:
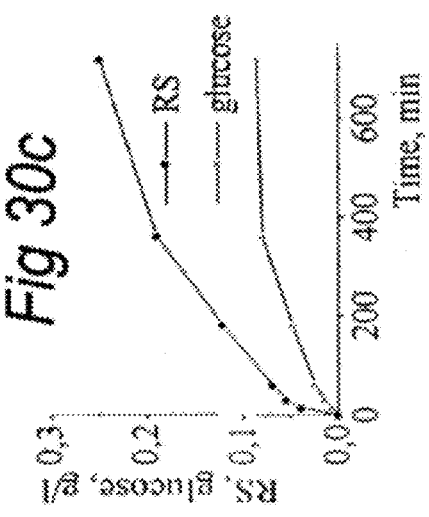
Figure 31A:
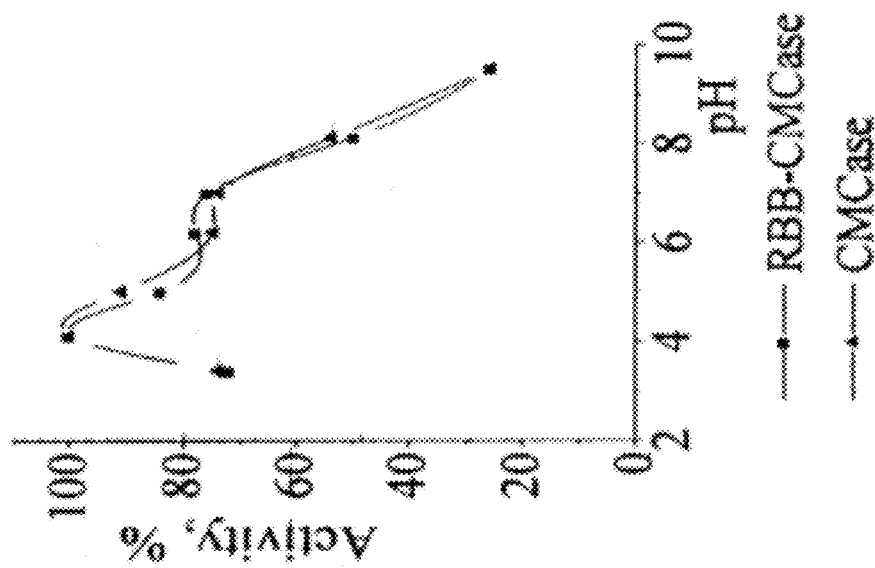
Figure 31B:
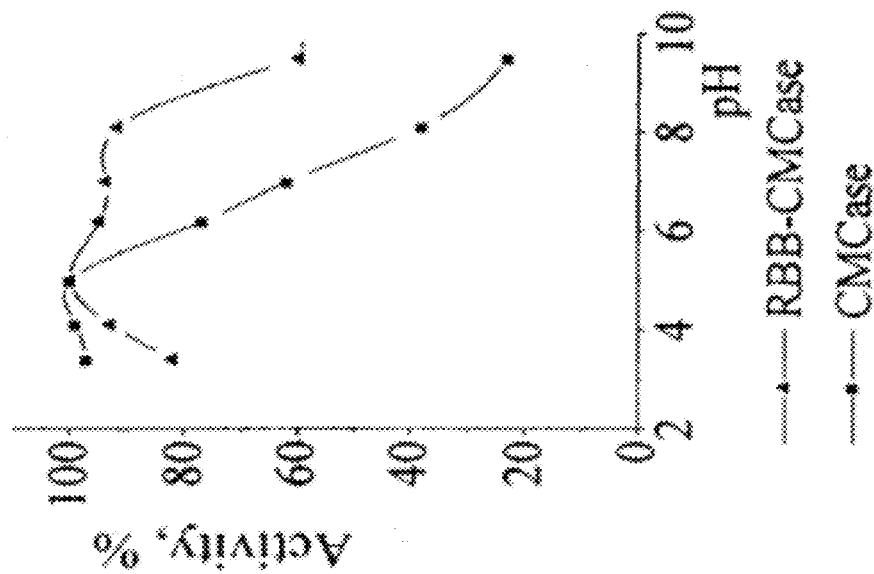
Figure 32:
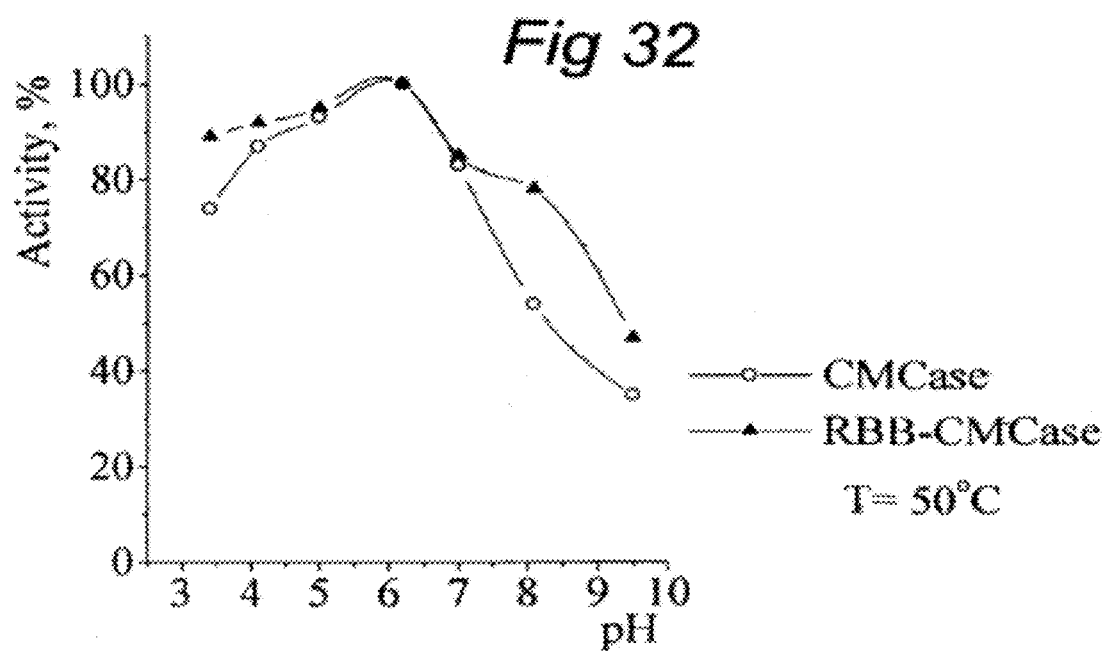
Figure 33A:
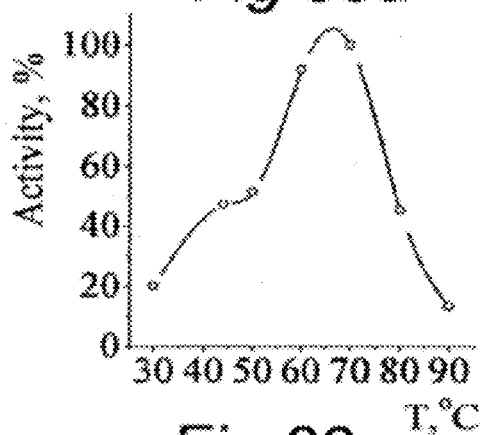
Figure 33B:
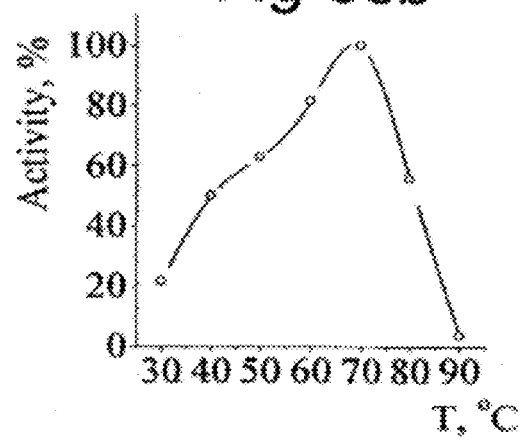
Figure 33C:
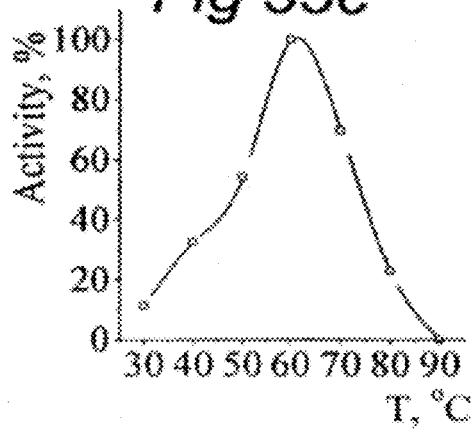
Figure 34A:
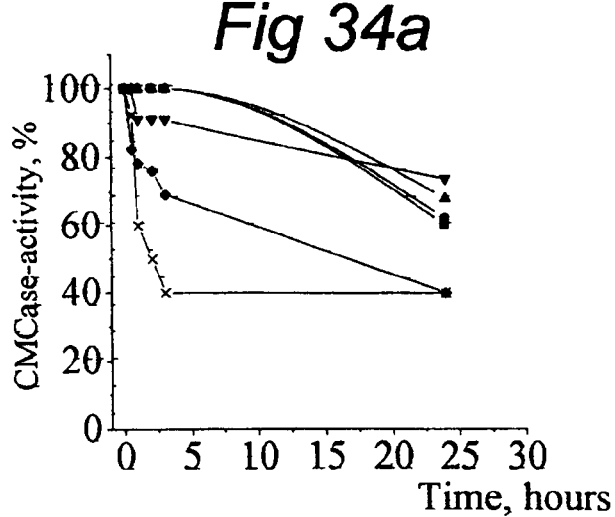
Figure 34B:
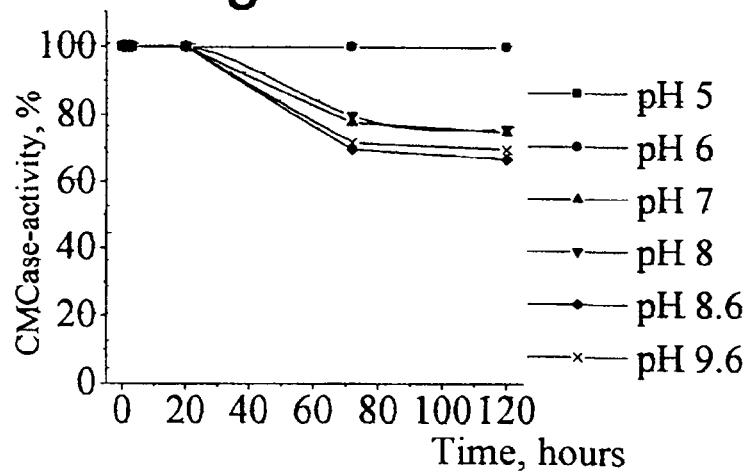
Figure 34C:
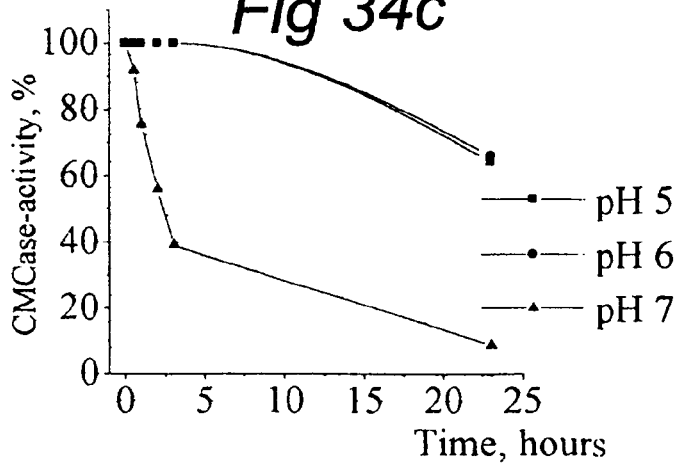
Figure 35:
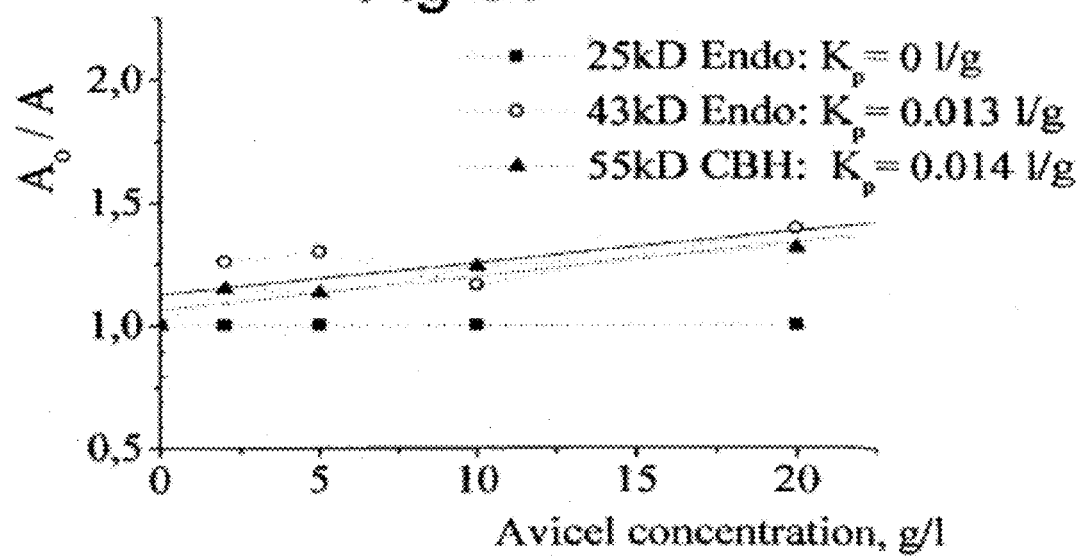

The vector also carries the beta-lactamase gene (bla) and an *E. coli* replication origin from plasmid pUC18[6]. The plasmid detailed map is provided in FIG. 5.

C1 protoplasts were transformed with plasmid pUT1064 or pUT1065 following the same procedure already described in example 1. The fusion protein in plasmid pUT1065 (Sh ble::XYN2) is functional with respect to the phleomycin-resistance thus allowing easy selection of the C1 transformants. Moreover, the level of phleomycin resistance correlates roughly with the level of xyn2 expression. In pUT1064, xyn2 was cloned with its own signal sequence.

The xylanase production of C1 transformants (phleomycin-resistant clones) was analysed by xylanase-activity assay as follow: Primary transformants were toothpicked to GS+phleomycin (5 µg/ml) plates (resistance verification) and also on XYLAN plates (xylanase activity detection by clearing zone visualisation[17]). Plates were grown for 5 days at 32° C. Each validated clone was subcloned onto XYLAN plates. Two subclones per transformant were used to inoculate PDA plates in order to get spores for liquid culture initiation. The liquid cultures in IC1+5 g/l KPhtalate were grown 5 days at 27° C. (shaking 180 rpm). Then, the cultures were centrifuged (5000 g, 10 min.). From these samples, xylanase activity was measured by DNS Technique according to Miller et al.[18]

TABLE H

Active XYN2 production levels in C1 (best producers)

|  | Active xylanase II concentration in culture media | Xylanase II specific activity in culture media |
|---|---|---|
| Untransformed UV18-25 | 3.9 U./ml | 3.8 U./mg total prot. |
| UV18-25::1064 clone 7-1 | 4.7 U./ml | 4.7 U./mg total prot. |
| UV18-25::1064 clone 7-2 | 4.4 U./ml | 4.3 U./mg total prot. |
| UV18-25::1065 clone 1-1 | 29.7 U./ml | 25.6 U./mg total prot. |
| UV18-25::1065 clone 1-2 | 30.8 U./ml | 39.4 U./mg total prot. |

These data show that:

1) Points 1 to 4 from example 2 are confirmed.

2) C1 can be used as host for the secretion of a heterologous fungal protein.

[4] We also illustrate data from expression of transformed UV18-25 wherein the table I shows the results for the plasmids with which transformation was carried out. The Table shows good expression levels for endoglucanase and cellobiohydrolase using heterologous expression regulating sequences and signal sequences but also with homologous expression regulating sequences and signal sequences. The details of the various plasmids can be derived elsewhere in the description and from the figures. The production occurs at alkaline pH at a temperature of 35° C.

TABLE I

Expression data of transformed UV18-25 strain

| Culture | Total proteins mg/ml | CMCase u/ml | CMCase u/mg | β-glucanase u/ml | β-glucanase u/mg | pH value |
|---|---|---|---|---|---|---|
| *UV 18-25 | 100% | 100% | 100% | 100% | 100% | 7.90 |
| 1150-23 | 94% | 105% | 111% | 140% | 149% | 7.90 |
| -30 | 96% | 105% | 110% | 145% | 151% | 8.10 |
| 1152-3 | 94% | 112% | 120% | 147% | 156% | 7.85 |
| -4 | 100% | 105% | 105% | 132% | 132% | 7.90 |
| 1160-2 | 69% | 81% | 118% | 90% | 131% | 7.90 |
| -4 | 73% | 72% | 98% | 83% | 114% | 8.35 |
| -1 | 92% | 95% | 103% | 120% | 130% | 8.45 |
| 1162-1 | 102% | 105% | 103% | 145% | 142% | 8.20 |
| -11 | 112% | 109% | 98% | 115% | 103% | 8.20 |
| F6g-20 | 104% | 102% | 98% | 130% | 125% | 7.90 |
| -25 | — | — | — | — | — | — |

Culture conditions (shake flask): 88 h, 35° C., 230 rpm
*all above figures are in relative % to parent UV18-25 strain Appendix to the Examples: Media
Transformation Media:

| Mandels Base: | |
|---|---|
| $KH_2PO_4$ | 2.0 g/l |
| $(NH_4)_2SO_4$ | 1.4 g/l |
| $MgSO_4 \cdot 7H_2O$ | 0.3 g/l |
| $CaCl_2$ | 0.3 g/l |
| Oligoelements | 1.0 ml/l |
| MnR | |
| MnP + sucrose | 130 g/l |
| Yeast extract | 2.5 g/l |
| Glucose | 2.5 g/l |
| Agar | 15 g/l |
| MnR Soft: | MnR with only 7.5 g/l of agar. |
| MPC: | |
| $CaCl_2$ | 50 mM PH 5.8 |
| MOPS | 10 mM |
| PEG | 40% |
| MnP Medium: | |
| Mandels Base with Peptone | 1 g/l |
| MES | 2 g/l |
| Sucrose | 100 g/l |
| Adjust pH to 5 | |
| MnP $CA^{2+}$: | |
| MnP Medium + $CaCl_2$ $2H_2O$ | 50 mM |
| Adjust pH to 6.5 | |

For Selection and Culture

| GS: | |
|---|---|
| Glucose | 10 g/l |
| Biosoyase | 5 g/l [Merieux] |
| Agar | 15 g/l pH should be 6.8 |
| PDA: | |
| Potato Dextrose Agar | 39 g/l [Difco] pH should be 5.5 |
| MPG: | |
| Mandels Base with | |
| K.Phtalate | 5 g/l |
| Glucose | 30 g/l |
| Yeast extract | 5 g/l |

The regeneration media (MnR) supplemented with 50 µg/ml phleomycin or 100-150 µg/ml hygromycin is used to select transformants. GS medium, supplemented with 5 µg/ml phleomycin is used to confirm antibiotic resistance.

PDA is a complete medium for fast growth and good sporulation. Liquid media are inoculated with ½0th of spore suspension (all spores from one 90 mm PDA plate in 5 ml 0.1% Tween). Such cultures are grown at 27° C. in shake flasks (200 rpm).

Isolation and Characterisation of C1 Proteins

Figure 36:
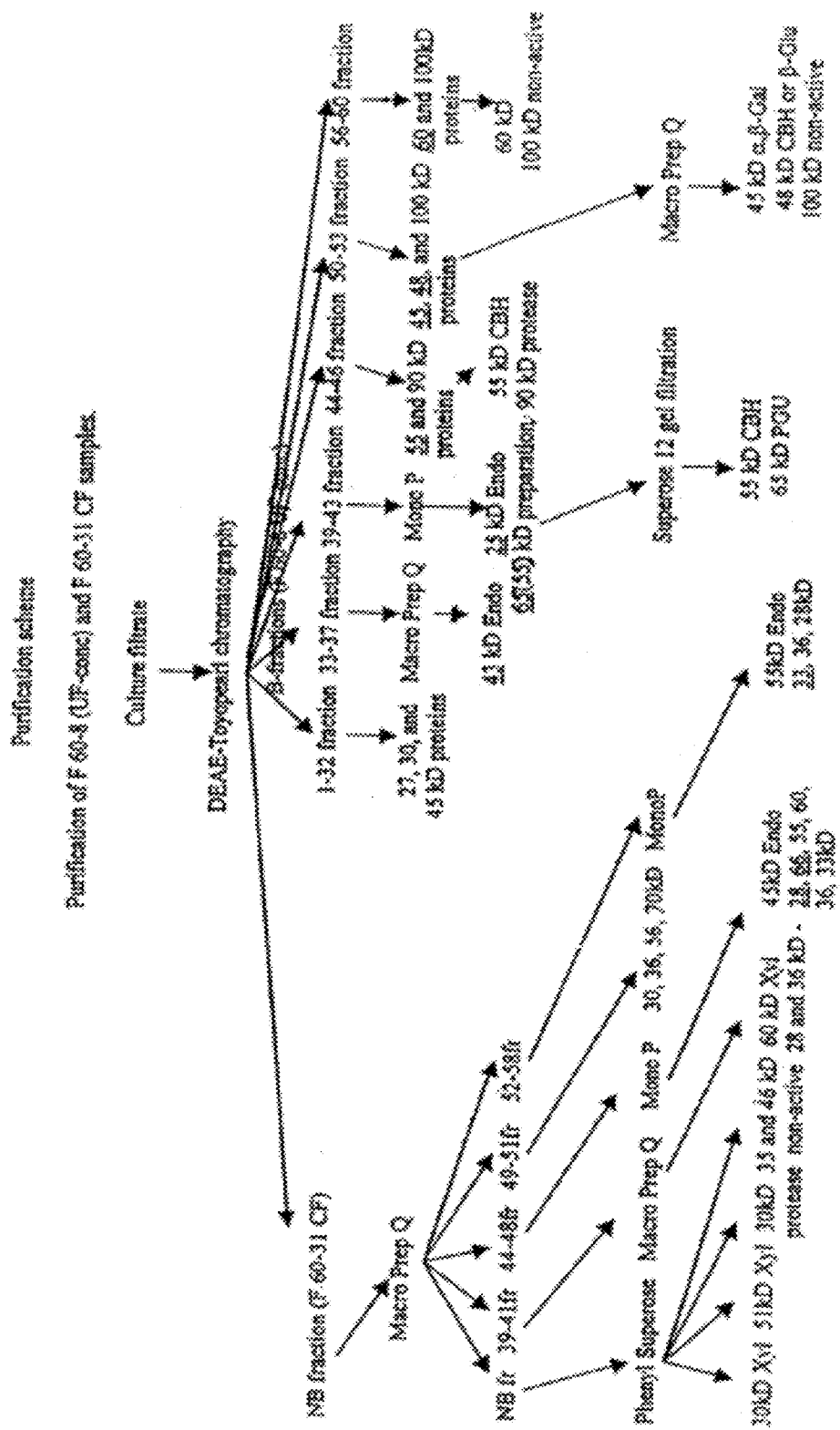

The process for obtaining various proteins is described as are a number of characteristics of the proteins. Tables A and B and FIG. 36 provide details of purification scheme and activities. Isolation occurs from the *Chrysosporium* culture filtrate using DEAE-Toyopearl ion exchange chromatography analogously to the method described in WO 98/15633, which is incorporated herein by reference. The non-bound fraction (F 60-31 CF) obtained from this chromatography was purified using Macro Prep Q™ (TM) ion exchange chromatography after equilibration to pH 7,6. The non-bound fraction (NB) was pooled and bound proteins were eluted in 0-1 M NaCl gradient. The NB fraction provided major protein bands of 19, 30, 35 and 46 kD and a minor one of 51 kD. In 0-1 M NaCl gradient protein peaks were eluted from various fractions. 39-41 included 28, 36 and 60 kD proteins, 44-48 included 28, 45 and 66 kD as major protein bands with 33, 36, 55, 60 and 67 kD proteins, the 49-51 fraction gave 30, 36, 56 and 68 kD proteins and the 52-59 fraction included major 33 and 55 kD proteins and minor 28 and 36 kD proteins. The pooled NB fraction was further purified by hydrophobic chromatography on Phenyl Superose™. The NB fraction was equilibrated with 0.03M Na-phosphate buffer pH 7.0 containing 1.2 M (NH4)2SO4 and applied to a column. Adsorbed proteins were eluted in 1.2-0.6 M (NH4)2SO4 gradient. Thus homogeneous xylanase with MW 30 and 51 kD and pI 9.1 and 8.7 respectively were obtained as was a 30 kD protease with pI 8,9.

The xylanases did not possess MUF cellobiase activity and are thus true xylanases. The alkaline 30 kD xylanase (pI 9.1) possessed high activity within a very broad pH range from 5-8 maintaining 65% of maximum activity at pH 9-10; it is a member of the xylanase F family; its partial nucleotide and amino acid sequences are depicted in SEQ ID No. 7. The partial amino acid sequence depicted corresponds to about amino acids 50-170 from the N terminus of the mature protein. Xylanases according to invention have at least 60%, preferably at least 70%, most preferably at least 80% sequence identity of the partial amino acid sequence of SEQ ID No. 7. The corresponding xylanase promoter, which is a preferred embodiment of the invention, can be identified using the partial nucleotide sequence of SEQ ID No. 7. The 51 kD xylanase (pI 8.7) possessed maximum activity at pH 6 and retained at least 70% of its activity at pH 7.5 and it retained at least 50% of its activity at pH 8.0. It was not very stable with only 15% activity at pH 5.5 and 4% at pH 7.5. The Michaelis constant toward birch xylan was 4.2 g/l for 30 kD xylanase and 3.4 g/l for 51 kD xylanase. Temperature optimum was high and equal to 70° C. for both xylanases.

The 30 kD protease activity measured towards proteins of the NB fraction appeared to be equal to $0.4 \times 10^{-3}$ units/ml at 50° C. and pH 7.90 kD. The fraction exhibited activity toward dyed casein of 0.4 arbitrary units/mg (pH 7). Addition of urea as chaotropic agent resulted in 2-3 times increase of protease activity. The effect of the protease on xylanase activity was significant. Only 30% xylanase activity remained at pH 10.3 and 50° C. after 30 minutes of incubation. At pH 8 95% of the xylanase activity remained. Linear alkylbenzene sulfonate (LAS) addition resulted in a dramatic decrease of xylanase activity at pH 8 and 10.3 with only 50% xylanase activity after 10 minutes of incubation with or without protease inhibitor PMSF. The 30 kD protease was alkaline with pH optimum at pH 10-11. The activity is inhibited by phenylmethylsulfonyl fluoride (PMSF) and not by iodoacetic acid, pepstatin A and EDTA which characterises it as a serine type protease. The protease is not active towards C1 proteins at neutral pH and 50° C. without chaotropic agents. Increase of pH and the addition of chaotropic agents such as LAS, SDS and urea significantly increase proteolysis.

The 39-41 fraction was purified by hydrophobic chromatography on phenyl superose. Fractions were equilibrated with 0.03M Na phosphate buffer pH 7.2 containing 1.5M (NH4)2SO4 and applied to a column. Adsorbed proteins were eluted in 1.5-0 M (NH4)2SO4 gradient. Thus homogenous xylanase with MW 60 kD and pI 4.7 was obtained. This xylanase possessed activities towards xylan, MUF-cellobioside, MUF-xyloside and MUF-lactoside. This xylanase probably belongs to family 10 (family F). This xylanase was stable at pH from 5 to 8 during 24 hours and retained more than 80% activity at 50° C. It retained 70% activity at pH 5-7 at 60° C. It kept 80% activity during 5 hours and 35% during 24 hours at 50° C. and pH 9. At pH 10 60% activity was retained at 50° C. and 0.5 hours of incubation. After 5 hours of incubation at pH 8 and 60° C. 45% activity was found decreasing to 0 after 24 hours. It had a pH optimum within the pH range of 6-7 and kept 70% activity at pH 9 and 50% of its activity at pH 9.5. The Michaelis constant toward birch xylan was 0.5 g/l. Temperature optimum was high and equal to 80° C.

Fraction 44-48 was then purified by chromatofocusing on Mono P. A pH gradient from 7.63-5.96 was used for the elution of the proteins. As a result 45 kD endoglucanase was isolated with a pI of 6. The 45 kD endo had maximum activity at pH 5 toward CMC and at pH 5-7 toward RBB-CMC. The 45 kD endo retained 70% of its maximal activity toward CMC at pH 6.5 and 70% of its maximal activity toward RBB-CMC was retained at pH 7.0; 50% of its maximal activity toward CMC was retained at pH 7 and 50% of its maximal activity toward RBB-CMC was retained at pH 8. The Michaelis constant toward CMC was 4.8 g/l. Temperature optimum was high and equal to 80° C. Other proteins 28, 33, 36, 55, 60 and 66 kD were eluted mixed together.

Fraction 52-58 was purified by chromatofocusing on Mono P too with a pH gradient 7.6-4.5. Individual 55 kD endoglucanase with pI 4.9 was obtained. The 55 kD endo was neutral. It has a broad pH optimum from 4.5-6 and 70% activity was retained at pH 7.0 both for CMC and RBB-CMC and 50% activity was retained at pH 8 for both CMC and RBB-CMC. The Michaelis constant toward CMC was 1 g/l. Temperature optimum was high and equal to 80° C. A number of fractions also held proteins with MW of 28, 33 and 36 kD.

45, 48 and 100 kD proteins were isolated from bound DEAE Toyopearl fraction of F 60-8 UF conc of *Chrysosporium* culture from fractions 50-53 using Macro Prep Q chromatography.

Fraction 50-53 was equilibrated with 0.03 M imidazole HCL buffer, pH 5.75 and was applied to a column and the adsorbed proteins were eluted in 0.1-0.25 M NaCl gradient for 4 h. As a result 45 kD (pI 4.2), 48 kD (pI 4.4) and 100 kD (pI 4.5) proteins were isolated in homogenous states.

The 45 kD protein is supposedly an alpha, beta-galactosidase by virtue of its activity toward p-nitrophenyl alpha-galactoside and p-nitrophenyl beta-galactoside. The pH optimum was 4.5 70% activity was maintained at pH 5.7 and 50% of its activity was retained at pH 6.8. The temperature optimum was 60° C.

The 48 kD protein was a cellobiohydrolase having high activity toward p-nitrophenyl beta-glucoside and also activities toward MUF cellobioside, MUF lactoside and p-nitrophenyl butyrate. The 48 kD protein had a pH optimum of 5 toward CMC and 5-6 toward RBB-CMC.

The 100 kD protein with pI 4.5 possessed activity only toward p-nitrophenyl butyrate. It is probably an esterase but is not a feruloyl esterase as it had no activity against the methyl ester of ferulic acid. It had neutral/alkaline pH optimum (pH 8-9) and optimal temperature of 55-60° C.

The 90 kD protease with pI 4.2 was isolated from the bound fraction and the activity measured towards proteins of the NB fraction appeared to be equal to $12 \times 10^{-3}$ units/ml at 50° C. and pH 7.90 kD. The fraction exhibited activity toward dyed casein of 0.01 arbitrary units/mg (pH 7). Addition of urea as chaotropic agent resulted in 2-3 fold increase of protease activity as did addition of LAS at both pH 7 and 9 (50° C.). The 90 kD protease was neutral with pH optimum at pH 8.

The activity is inhibited by phenylmethylsulfonyl fluoride (PMSF) and not by iodoacetic acid, pepstatin A and EDTA which characterises it as a serine type protease.

Also isolated from the bound fraction were 43 kD endoglucanase with pI 4.2 (fraction 33-37) and 25 kD endoglucanase with pI 4.1 (fraction 39-43), 55 kD cellobiohydrolase with pI 4.9 (fraction 39-43) and 65 kD polygalacturonase with pI 4.4 (fraction 39-43). The endoglucanases did not possess activity towards avicel or MUF cellobioside and possessed high activity toward MC, RBB-CMC, CMC41, beta-glucan and endoglucanase. The 25 kD endo did not produce glucose from CMC and the 43 kD endo did. No glucose was formed from avicel. The pH optimum for the 43 kD protein was 4.5 with 70% maximum activity maintained at pH 7.2 and 50% at pH 8. The 43 kD endo kept 70% activity at pH 5 and 6 during 25 hours of incubation. It kept only 10% at pH 7 during this incubation period. The 25 kD endo had pH optimum of activity at pH 5 toward CMC and broad pH optimum of activity toward RBB-CMC with 70% of the maximum activity being kept at pH 9 and with 50% of the maximum activity being at pH 10. It kept 100% activity at pH 5 and 6 and 80% at pH 7, 8, 8.6 and 9.6 during 120 hours of incubation. The 25 kD endo had a temperature optimum of activity at 70° C. The 43 kD endo had a temperature optimum of activity at 60° C. The Michaelis constants towards CMC were 62 and 12.7 g/l for 25 and 43 kD endo respectively. The polygalacturonase is a pectinase. The Michaelis constant toward PGA was 3.8 g/l. The pH optimum of PGU activity is within pH range 5-7 and T optimum within 50-65° C.

Genes encoding *C. lucknowense* proteins were obtained using PCR and characterised by sequence analysis. The corresponding full genes were obtained by screening (partial) gene libraries using the isolated PCR fragments. The full gene of the 43 kD endoglucanase (EG6, Family 6) of the C1 strain has been cloned, sequenced and analysed (including 2.5 kb promoter region and 0.5 kb terminator region). Its nucleotide and amino acid sequences are depicted in SEQ ID No. 6. Predicted molecular weight of the mature protein is 39,427 Da and predicted pI is 4.53, which values correspond well with the measured values. Protein alignment analysis with other glycosyl hydrolases of the family 6.2 shows that C1-EG6 does not include a cellulose-binding domain (CBD) Homology analysis using SwissProt SAMBA software (Smith & Waterman algorithm, Gap penalty 12/2, alignment 10, Blosum62 matrix) shows that $C_1$-EG6 has 51.6% identity with *Fusarium oxysporum* EG-B (over 376 amino acids), 51.0% identity with *Agaricus bisporis* CBH3 (over 353 amino acids), and 50.7% identity with *Trichoderma reesei* CBH2 (over 367 amino acids). The putative signal sequence runs Met 1 to Arg 28. The promoter contains several potential CreA binding sites, so it is very likely that this promoter would be subject to glucose repression in a fungal strain with working CreA regulation.

Similarly, the full gene of the 25 kD endoglucanase (EG5, Family 45) of the C1 strain has been cloned, sequenced and analysed (including 3.3 kb promoter region and 0.7 kb terminator region). The nucleotide and amino acid sequences are depicted in SEQ ID No. 5. Predicted molecular weight of the mature protein is 21,858 Da and predicted pI is 4.66, which values correspond well with the measured values. This is the smallest fungal endoglucanase known to date. Protein alignment analysis with other glycosyl hydrolases of the family 45 shows that C1-EG5 does not include a cellulose-binding domain (CBD), nor a cohesin/dockerin domain. Homology analysis using NCBI-BLASTP2 software (Gap penalty 11/1, alignment 10, Blosum62 matrix) shows that the closest homologous protein to C1-EG5 is *Fusarium oxysporum* EG-K with 63% identity. The putative signal sequence runs Met 1 to Ala 18. The promoter contains many potential CreA binding sites, so it is very likely that this promoter would be subject to glucose repression in a fungal strain with working CreA regulation.

Furthermore, an additional endoglucanase was found by PCR based on family 12 cellulases homology analysis. The partial nucleotide and amino acid sequence of this additional endoglucanase (EG3, Family 12) is given in SEQ ID No. 8.

The 55 kD protein was a cellobiohydrolase (referred to herein as CBH1) with activity against MUF-cellobioside, MUF lactoside, filter paper and avicel, also against p-nitrophenyl β-glucoside, cellobiose and p-nitrophenyl lactoside. Its activity toward MUF cellobioside is inhibited by cellobiose. The inhibition constant 0.4 mM was determined. The Michaelis constant toward MUF cellobioside was 0.14 mM, toward MUF lactoside was 4 mM and toward CMC was 3.6 g/l. The pH optimum is rather broad from 4.5 to 7.50% of maximum activity toward CMC and 80% activity toward RBB-CMC is kept at pH 8. 70-80% activity within pH 5-8 is kept during 25 hours of incubation. The temperature optimum is 60-70° C. CBH1 is probably a member of the cellobiohydrolase family 7; its partial nucleotide and amino acid sequences are depicted in SEQ ID No. 9. The partial amino acid sequence depicted corresponds to about amino acids 300-450 from the N terminus of the mature protein. A cellobiohydrolase according to the invention has at least 60%, preferably at least 70%, most preferably at least 80% sequence identity of the partial amino acid sequence of SEQ ID No. 9. The corresponding CBH promoter, which is a preferred embodiment of the invention, can be identified using the partial nucleotide sequence of SEQ ID No. 9. A synergistic effect was observed between 25 kD endo and 55 kD CBH during avicel hydrolysis. Synergism coefficient was maximal at the ratio of 25 kD endo to 55 kD CBH 80:20. The $K_{syn}$ was 1.3 at its maximum.

The expression level of five main *Chrysosporium* genes was studied by Northern analysis. Various strains of *C. lucknowense* were grown in rich medium containing Pharmamedia with cellulose and lactose (medium 1) or rich medium containing Pharmamedia and glucose (medium 2) at 33° C. After 48 h, mycelium was harvested and RNA was isolated. The RNA was hybridised with 5 different probes: EG5, EG6, EG3, XylF and CBH. After exposure, the Northern blots were stripped and hybridised again with a probe for ribosomal L3 as a control for the amount of mRNA on the blot. Most strains showed very high response for CBH and high response for XylF in medium 1; in medium 2, half of the strain showed high response for all genes, and the other half showed low response. The order of expression strength was deduced from these data as CBH>XylF>EG5>EG3>EG6.

Tables A and B and FIG. 36 illustrate the details of the above.

Advanced Isolation and Characterisation of C1 Genes and Gene Expression Sequences of cbh1, xyl1, eg3 and gpd
Construction of a BlueSTAR gene library of UV18-25

Chromosomal DNA of UV18-25 was partially digested with Sau3A, fragments of 12-15 kb were isolated and ligated in a BamHI site of cloning vector BlueSTAR. Packaging of 20% of the ligation mixture resulted in a gene library of $4.6 \times 10^4$ independent clones. This library was multiplied and stored at 4° C. and −80° C. The rest of the ligation mixture was also stored at 4° C.
Screening the Gene Library of UV18-25 for Isolation of the Genes for cbh1, eg3, xyl1 and gpd1

For the isolation of the different genes, in total $\pm 7.5 \times 10^4$ individual BlueSTAR phages per probe were hybridized in duplicate. Hybridisation was carried out with the PCR fragments of cbh1, eg3 and xyl1 (as described in PCT/NL99/00618) at homologous conditions (65° C.; 0.2×SSC) and with the gpd1 gene of *A. niger* at heterologous conditions (53° C.; 0.5×SSC). The number of positive signals is given in Table K. The positive clones were rescreened and for each clone two individual phages were used for further experiments. DNA of the different clones was analysed by restriction analysis to determine the number of different clones isolated from each gene (results are given in Table K).

As for each of the 4 genes, 4-6 different clones were isolated, we conclude that the primary gene library (±4-5×10$^4$ clones) represents about 5× genome of UV18-25. From this result we conclude that the complete genome of UV18-25 is represented in 9×10$^3$ clones. Based on an average genomic insert of 13 kb, this would indicate a genome size of ±120 Mb, which is 3 times the size of the *Aspergillus* genome.

PCR reactions with specific primers for the gene present on the plasmid (based on previous sequence determination from the isolated PCR fragments) and the T7 and T3 primer present in the polylinker of pBlueSTAR we were able to determine the location of the genes in a number of clones. From each gene a plasmid was used for sequence determination of the gene.

Sequence Analysis of the Cloned Genes

For the cbh1, xyl1, eg3 and the gpd1 gene, the results of the sequence determination are represented in SEQ ID No's 1, 2, 3 and 4 respectively. Also the deduced amino acid sequences of the proteins are represented in these SEQ ID No's 1-4. Some properties of the proteins are given in Table L. It should be mentioned that the position of the start of the translation and the introns is based on homology with genes from the same family (i.e. paper genetics).

CBH1

From the amino acid sequences of CBH1, we concluded that the protein is about 63 kD in size and that a cellulose binding domain (CBD) is present at the C-terminal part of the protein. Interestingly, no evidence was found for the presence of a CBD in the isolated 55 kD major protein. However, the presence of the isolated peptides from this 55 kD major protein in the encoded CBH1 protein (SEQ ID No. 1), confirms that the 55 kD protein is encoded by the cloned gene. A possible explanation of these results is that the 55 kD protein is a truncated version of the CBH1 protein lacking the CBD.

Xyl1

From the amino acid sequences of xyl1 we conclude that also here a CBD is present, in this protein at the N-terminal side. In the literature only two more xylanases with a CBD are known (*Fusarium oxysporum* and *Neocallimastix patriciarum*). The estimated size of the Xyl1 protein is 43 kD and several peptides isolated from a 30 kD xylanase originate from this protein (SEQ ID No. 2). It should be noted that a considerable number of the isolated peptides could not be found in the encoded sequence. This could indicate that alternative xylanase proteins are present in UV18-25. In previous analysis, no evidence was found for the presence of CBD in this 30 kD protein. Also from these results we hypothesized that the CBD of the protein is cleaved of by proteolysis. This hypothesis will be analysed further (by determination of activities, N-terminal sequences and sizes of the different proteins in the different C1 strains: C1 wild type, NG7C, UV13-6, UV18-25 and protease⁻ mutants of UV18-25) Also the effect of the presence or absence of the CBD on enzymatic activities has to be analysed in detail further. Overexpression of the full length genes in various C1 hosts may be considered. The presence of a cellulose binding domain (CBD) is a particular feature of this enzyme; the only other known family 10 glycolytic enzyme (xylanase) having a CBD is the *Fusarium oxysporum* XylF. The invention thus pertains to fungal xylanases having a CBD other than the *Fusarium oxysporum* xylanase.

EG3

From the amino acid sequence of EG3 it could be concluded that EG3 is a family 12 protein. The gene encodes a preproprotein with a dibasic (K-R) propeptide processing site. The C1EG3 protein is 62% similar and 54% identical to the B1 EG3 protein. One putative glycosylation site is present at the C-terminal part of the protein (SEQ ID No. 3).

Gpd1

The DNA sequence of the C-terminal part of the gpd1 gene is not determined, since we are primarily interested in the promoter sequences of this gene (SEQ ID No. 4).

The proteins XYL1 and EG3 of *C. lucknowense* are 54-70% identical to their closest homologue in the Genbank DATABASE (Table L). Notable is the strong homology of the CBH1 and the EG5 proteins to their related *Humicola grisea* proteins (74-82% identical). Interestingly the closest related proteins to the EG6 protein are only 46-48% identical.

Also notable is that in most cases the closest homologues originate from *Fusarium, Humicola* or other Pyrenomycetous fungi (Table L), whereas *Chrysosporium* belongs to the Plectomycetous fungi according to the NCBI taxonomy database (Table L).

TABLE K

Screening of 7.5 × 10$^4$ phages of the gene library of UV18-25 with PCR fragments of UV18-25 for the cbhl gene, the eg3 gene and the xyll gene (homologous conditions) and with the gpdA gene of *A. niger* (heterologous conditions). DNA isolation and restriction analysis was used to determine the number of different clones.

| Gene | Positive in first screening | positive in rescreening | different clones | clone used for sequencing |
|---|---|---|---|---|
| cbh1 | 8 | 7 | 4 | pCBH7 |
| eg3 | 6 | 6 | 4 | pEG3-3 |
| xyl1 | 9 | 6 | 5 | pXyl5 |
| gpd1 | 12 | 12 | 6 | pGPD4 |

TABLE L

| | glycosidase family | isolated from C1 | number of amino acids | introns | remarks | related sequences (% identity/% homology) |
|---|---|---|---|---|---|---|
| CBH1 | 7 | 70 kD<br>55 kD | 526<br>(63 kD) | 1 | CBD | *Humicola grisea* (74/82)<br>(CBH1: P15828)<br>*Fusarium oxysporum* (58/68)<br>(CBH: P46238)<br>*Neurospora crassa* (60/69)<br>(CBH1: P38676) |

TABLE L-continued

| glycosidase family | isolated from C1 | number of amino acids | introns | remarks | related sequences (% identity/% homology) |
|---|---|---|---|---|---|
| XYL1 | 10 | 30 kD | 333 (43 kD) | 3 | CBD | Fusarium oxysporum (67/72) (XylF: P46239) Penicillium simplissicum (63/72) (XylF: P56588) Aspergillus aculeatus (61/70) (XylF: O59859) |
| EG3 | 12 | — | 247 (30 kD + glycos) | 2 | prepro peptide | Aspergillus aculeatus (60/71) (F1-CMCase: P22669) Hypocrea jecorina (56/73) (EG: BAA20140) Aspergillus kawachii (54/69) (CMCase: Q12679) |
| EG6 | 6(2) | 43 kD | 395 | 2 | no CBD | Fusarium oxysporum (48/59) (EGLB: P46236) Acremonium cellulolyticus (48/58) (CBHII: BAA74458) Agaricus bisporus (46/59) (CBH3: P49075) |
| EG5 | 45 | 25 kD | 225 | 3 | no CBD | Humicola grisea (82/91) (EG: BAA74957) Fusarium oxysporum (63/78) (EGL-K: P45699) Humicola grisea (62/78) (EG: BAA74956) |
| GPD1 | — | — | Incomplete | 2 + ? | — | Podospora anserina (85/89) (GPD: P32637) Neurospora crassa 80/86 (GPD: U67457) Cryphonectria parasitica 80/85 (GPD: P19089) | xxx

REFERENCES

The Contents Hereof are Incorporated

1. Calmels T. P., Martin F., Durand H., and Tiraby G. (1991) *Proteolytic events in the processing of secreted proteins in fungi.* J Biotechnol 17(1): p. 51-66.
2. Punt P. J., Dingemanse M. A., Jacobs-Meijsing B. J., Pouwels P. H., and van den Hondel C. A. (1988) *Isolation and characterization of the glyceraldehyde-3-phosphate dehydrogenase gene of Aspergillus nidulans.* Gene 69(1): p. 49-57.
3. Shoemaker S., Schweickart V., Ladner M., Gelfand D., Kwok S., Myambo K., and Innis M. (1983) *Molecular cloning of exo-cellobiohydrolase I derived from Trichoderma reesei strain L27.* Bio/Technology October: 691-696.
4. Drocourt D., Calmels T., Reynes J. P., Baron M., and Tiraby G. (1990) *Cassettes of the Streptoalloteichus hindustanus ble gene for transformation of lower and higher eukaryotes to phleomycin resistance.* Nucleic Acids Res 18(13): p. 4009.
5. Mullaney E. J., Hamer J. E., Roberti K. A., Yelton M. M., and Timberlake W. E. (1985) *Primary structure of the trpC gene from Aspergillus nidulans.* Mol Gen Genet. 199(1): p. 37-45.
6. Yanisch-Perron C., Vieira J., and Messing J. (1987) *Improved M13 phage cloning vectors and host strains: nucleotide sequences of the M13mp18 and pUC19 vectors.* Gene 33:103-119.
7. Durand H., Baron M., Calmels T., and Tiraby G. (1988) *Classical and molecular genetics applied to Trichoderma reesei for the selection of improved cellulolytic industrial strains*, in *Biochemistry and genetics of cellulose degradation*, J. P. Aubert, Editor. Academic Press. p. 135-151.
8. Lowry O. H., Rosebrough N. J., Farr A. L., and Randall R. J. (1951) *Protein measurements with the folin phenol reagent.* J. Biol. Chem. ?: 193-265.
9. Parriche M., Bousson J. C., Baron M., and Tiraby G. *Development of heterologous protein secretion systems in filamentous fungi.* in 3rd European Conference on Fungal Genetics. 1996. Münster, Germany.
10. Baron M., Tiraby G., Calmels T., Parriche M., and Durand H. (1992) *Efficient secretion of human lysozyme fused to the Sh ble phleomycin resistance protein by the fungus Tolypocladium geodes.* J Biotechnol 24(3): p. 253-266.
11. Jeenes D. J., Marczinke B., MacKenzie D. A., and Archer D. B. (1993) *A truncated glucoamylase gene fusion for heterologous protein secretion from Aspergillus niger.* FEMS Microbiol. Lett. 107(2-3): p. 267-271.
12. Stone P. J., Makoff A. J., Parish J. H., and Radford A. (1993) *Cloning and sequence-analysis of the glucoamylase gene of neurospora-crassa.* Current Genetics 24(3): p. 205-211.
13. Mörsky P. (1983) *Turbidimetric determination of lysozyme with Micrococcus lysodeikticus cells: Reexamination of reaction conditions.* Analytical Biochem. 128: 77-85.
14. Paluh J. L., Orbach M. J., Legerton T. L., and Yanofsky C. (1988) *The cross-pathway control gene of Neurospora crassa, cpc-1, encodes a protein similar to GCN4 of yeast and the DNA-binding domain of the oncogene v-jun-encoded protein.* Proc Natl Acad Sci USA 85(11): p. 3728-32.
15. Nakari T., Onnela M. L., Ilmen M., Nevalainen K., and Penttilä M. (1994) *Fungal promoters active in the presence of glucose*, Patent #WO 94/04673, Alko.
16. Torronen A., Mach R. L., Messner R., Gonzalez R., Kalkkinen N., Harkki A., and Kubicek C. P. (1992) *The two major xylanases from Trichoderma reesei: characterization of both enzymes and genes.* Biotechnology (N Y) 10(11): p. 1461-5.

17. Farkas V. (1985) *Novel media for detection of microbial producers of cellulase and xylanase.* FEMS Microbiol. Letters 28:137-140.
18. Miller G. L. (1959) *Use of dinitrosalicylic acid reagent for determination of reducing sugar.* Anal. Chem. 31:426-428.
19. Punt P. J., Mattern I. E., van den Hondel C. A. M. J. J. (1988) *A vector for Aspergillus transformation conferring phleomycin resistance.* Fungal Genetics Newsletter 35, 25-30.

```
SEQ ID No. 1:
DNA sequence and amino acid of complete Chrysosporium CBH1 gene
including promoter and terminator sequences. Promoter, terminator
and intron sequences are given in small case. The putative signal
peptide is shown in italic letters and the cellulose binding
domain (CBD) is shown in bold underlined letters.
aaggtatccgatttggggaacgtcgatgaaagtattgcaaaagtgacgagagttgcgcaa      60 ctaactcgctgccgaagaagctgcggaagaaagagaacaccgaaagtggaataacgttac    120 ggatgtcctgacctcaaagttgaaaccagcccttcctgctctatttgggaaagcggcttg    180 cccttgaatgcgctgcactgtggcacgactaccagtgatcgggaggagcaaactaccctg    240 gtccgttccttggtggggcggcactagggcccaacttagggtgatcggaggtcgatgccgc    300 ggtcctcgttggtctgggctcttctcatttcccggtttgcaccccccgttgcacctgctg    360 atcgcccgccaacgccgatgaggttgcgcccagaccgacaatcaccgcggctgcattccc    420 aagtatattgaagatggcaccaggtacccggttttgcgtcccagtcgtttggtgccaaat    480 ttgggagttttgagcctcaagatctggggaaatcgacctcaacttccatacaagttaaa    540 gtcgcacacacggcgagttccacgaagagacacattttttctgaaggcctctctcccg     600 cacatcagaaaccaccaaataccaagactgcagaagccggggtaagtgggccaccgggac    660 tacactaaaatgcggggagaagcgagatccgttgcgaagggaagggatggggtgtgctgc    720 ggctttctccgctctcgtgcgccttttgcttgaatctagtgtacaccagggtaggctccg    780 aaggagtatctacggcagcgctgttcgtgctgcgttgagagtcagggcggagacgagcag    840 gcgacaggagcctcgcaccggcacttcggatcgcatttgcgcggagcgtcaaatacgctc    900 ttctgcggtcatcagagagcatcgtgaaccaaggttcttccgcagggcggcctgggcttc    960 gcagagtcgcactcggcggacgccttccgtgtcacccctgataacctggctgccgcgccc   1020 agactcctccaatgaggtgtgtggttgccctcgccgacccttcagcaaccttaatcgctt   1080 ccatcgcacggctccacgtcctcgaacgatgccctcagtccgtgcccggccgtggcaacc   1140 ataacgtgacatcgccgcccagcctactagccgctatcgaccggttaggcttgtcaccgc   1200 agcgcccattctccatcgggcctctactctgatccacctcacccaccgcaagcactagcg   1260 agcctcaccagagtgcaagcgacacgacccgcttggcccttcgtccttgactatctccca   1320 gacctcttgccatcttgccgacgccgccccttttttttctcctcccctgccggcaggt    1380 cggtggcccagtcccgagatggcattgctccgttgtccatgacgacccatcattcgatg    1440 gctgactggcacactcgtcttgtttgagcatcgacggcccgcggcccgtctcccacggta   1500 cggaacctcgttgtacagtacctctcgtaatgatacccaacaccggggccgagcgctggg   1560 agggcggcgttcccgagaagccgggaaggcggctggccggctgacctttgtgacttggcg   1620 atggatgcggccatggagaatgtccgtccgaagcgacgcgacaattagcctggctaccat   1680 cgatataaattgggtgattcccagctcttgatgggcgtgtcttctgcctggcagccctcg   1740 tcttcagatcaagcaactgtgtgctgatcctcttccgccATGTACGCCAAGTTCGCGACC   1800
                                        M  Y  A  K  F  A  T CTCGCCGCCCTTGTGGCTGGCGCCGCTGCTCAGAACGCCTGCACTCTGACCGCTGAGAAC   1860
 L  A  A  L  V  A  G  A  A  A  Q  N  A  C  T  L  T  A  E  N CACCCCTCGCTGACGTGGTCCAAGTGCACGTCTGGCGGCAGCTGCACCAGCGTCCAGGGT   1920
 H  P  S  L  T  W  S  K  C  T  S  G  G  S  C  T  S  V  Q  G
```

```
TCCATCACCATCGACGCCAACTGGCGGTGGACTCACCGGACCGATAGCGCCACCAACTGC  1980
 S  I  T  I  D  A  N  W  R  W  T  H  R  T  D  S  A  T  N  C

TACGAGGGCAACAAGTGGGATACTTCGTACTGCAGCGATGGTCCTTCTTGCGCCTCCAAG  2040
 Y  E  G  N  K  W  D  T  S  Y  C  S  D  G  P  S  C  A  S  K

TGCTGCATCGACGGCGCTGACTACTCGAGCACCTATGGCATCACCACGAGCGGTAACTCC  2100
 C  C  I  D  G  A  D  Y  S  S  T  Y  G  I  T  T  S  G  N  S

CTGAACCTCAAGTTCGTCACCAAGGGCCAGTACTCGACCAACATCGGCTCGCGTACCTAC  2160
 L  N  L  K  F  V  T  K  G  Q  Y  S  T  N  I  G  S  R  T  Y

CTGATGGAGAGCGACACCAAGTACCAGAgtaagttcctctcgcacccggccgccgggaga  2220
 L  M  E  S  D  T  K  Y  Q  M tgatggcgcccagcccgctgacgcgaatgacacaGTGTTCCAGCTCCTCGGCAACGAGTT  2280
                                    F  Q  L  L  G  N  E  F CACCTTCGATGTCGACGTCTCCAACCTCGGCTGCGGCCTCAATGGCGCCCTCTACTTCGT  2340
 T  F  D  V  D  V  S  N  L  G  C  G  L  N  G  A  L  Y  F  V GTCCATGGATGCCGATGGTGGCATGTCCAAGTACTCGGGCAACAAGGCAGGTGCCAAGTA  2400
 S  M  D  A  D  G  G  M  S  K  Y  S  G  N  K  A  G  A  K  Y CGGTACCGGCTACTGTGATTCTCAGTGCCCCGCGACCTCAAGTTCATCAACGGCGAGGC  2460
 G  T  G  Y  C  D  S  Q  C  P  R  D  L  K  F  I  N  G  E  A CAACGTAGAGAACTGGCAGAGCTCGACCAACGATGCCAACGCCGGCACGGGCAAGTACGG  2520
 N  V  E  N  W  Q  S  S  T  N  D  A  N  A  G  T  G  K  Y  G CAGCTGCTGCTCCGAGATGGACGTCTGGGAGGCCAACAACATGGCCGCCGCCTTCACTCC  2580
 S  C  C  S  E  M  D  V  W  E  A  N  N  M  A  A  A  F  T  P CCACCCTTGCACCGTGATCGGCCAGTCGCGCTGCGAGGGCGACTCGTGCGGCGGTACCTA  2640
 H  P  C  T  V  I  G  Q  S  R  C  E  G  D  S  C  G  G  T  Y CAGCACCGACCGCTATGCCGGCATCTGCGACCCCGACGGATGCGACTTCAACTCGTACCG  2700
 S  T  D  R  Y  A  G  I  C  D  P  D  G  C  D  F  N  S  Y  R CCAGGGCAACAAGACCTTCTACGGCAAGGGCATGACGGTCGACACGACCAAGAAGATCAC  2760
 Q  G  N  K  T  F  Y  G  K  G  M  T  V  D  T  T  K  K  I  T GGTCGTCACCCAGTTCCTCAAGAACTCGGCCGGCGAGCTCTCCGAGATCAAGCGGTTCTA  2820
 V  V  T  Q  F  L  K  N  S  A  G  E  L  S  E  I  K  R  F  Y CGTCCAGAACGGCAAGGTCATCCCCAACTCCGAGTCCACCATCCCGGGCGTCGAGGGCAA  2880
 V  Q  N  G  K  V  I  P  N  S  E  S  T  I  P  G  V  E  G  N CTCCATCACCCAGGACTGGTGCGACCGCCAGAAGGCCGCCTTCGGCGACGTGACCGACTT  2940
 S  I  T  Q  D  W  C  D  R  Q  K  A  A  F  G  D  V  T  D  ?

NCAGGACAAGGGCGGCATGGTCCAGATGGGCAAGGCCCTCGCGGGGCCCATGGTCCTCGT  3000
 Q  D  K  G  G  M  V  Q  M  G  K  A  L  A  G  P  M  V  L  V

CATGTCCATCTGGGACGACCACGCCGTCAACATGCTCTGGCTCGACTCCACCTGGCCCAT  3060
 M  S  I  W  D  D  H  A  V  N  M  L  W  L  D  S  T  W  P  I

CGACGGCGCCGGCAAGCCGGGCGCCGAGCGCGGTGCCTGCCCCACCACCTCGGGCGTCCC  3120
 D  G  A  G  K  P  G  A  E  R  G  A  C  P  T  T  S  G  V  P

CGCTGAGGTCGAGGCCGAGGCCCCCAACTCCAACGTCATCTTCTCCAACATCCGCTTCGG  3180
 A  E  V  E  A  E  A  P  N  S  N  V  I  F  S  N  I  R  F  G

CCCCATCGGCTCCACCGTCTCCGGCCTGCCCGACGGCGGCAGCGGCAACCCCAACCCGCC  3240
 P  I  G  S  T  V  S  G  L  P  D  G  G  S  G  N  P  N  P  P

CGTCAGCTCGTCCACCCCGGTCCCCTCCTCGTCCACCACATCCTCCGGTTCCTCCGGCCC  3300
 V  S  S  S  T  P  V  P  S  S  S  T  T  S  S  G  S  S  G  P

GACTGGCGGCACGGGTGTCGCTAAGCACTATGAGCAATGCGGAGGAATCGGGTTCACTGG  3360
 T  G  G  T  G  V  A  K  H  Y  E  Q  C  G  G  I  G  F  T  G

CCCTACCCAGTGCGAGAGCCCCTACACTTGCACCAAGCTGAATGACTGGTACTCGCAGTG  3420
 P  T  Q  C  E  S  P  Y  T  C  T  K  L  N  D  W  Y  S  Q  C

CCTGTAAacgaacctctctgaaggaggttctgagacacgcgcgattcttctgtatatagt  3480
 L  * tttattttcactctggagtgcttcgctccaccagtacataaaccttttttttcacgtaa   3540 caaaatggcttctttttcagaccatgtgaaccatcttgatgccttgacctcttcagttctc 3600
```

```
actttaacgtagttcgcgttagtctgtatgtcccagttgcatgtagttgagataaatacc    3660 cctggaagtgggtctgggcctttgtgggacggagccctctttctgtggtctggagagccc    3720 gctctctaccgcctaccttcttaccacagtacactactcacacattgctgaactgaccca    3780 tcataccgtactttatcctgttaattcgtggtgctgtcgactattctatttgctcaaatg    3840 gagagcacattcatcggcgcagggatacacggtttatggaccccaagagtgtaaggacta    3900 ttattagtaatattatgcctctaggcgccttaacttcaacaggcgagcactactaatc     3960 aactttggtagacccaattacaaacgaccatacgtgccggaaattttgggattccgtcc    4020 gctctccccaaccaagctagaagaggcaacgaacagccaatcccggtgctaattaaatta    4080 tatggttcattttttttaaaaaaattttttcttcccattttcctctcgcttttcttttc    4140 gcatcgtagttgatcaaagtccaagtcaagcgagctatttgtgctatagctcggtggcta    4200 taatcagtacagcttagagaggctgtaaaggtatgataccacagcagtattcgcgctata    4260 agcggcactcctagactaattgttacggtctacagaagtaggtaataaaagcgttaattg    4320 ttctaaatactagaggcacttagagaagctatctaaatatatattgaccctagcttatta    4380 tccctattagtaagttagttagctctaacctatagatagccaaatgctataataggtacc    4440 agggttcaaaa                                                    4451
```

SEQ ID No. 10
CBH1 protein sequence. Signal sequence is given in italic, the
CBD underlined in bold.

```
MYAKFATLAA LVAGAAAQNA CTLTAENHPS LTWSKCTSGG SCTSVQGSIT        50

IDANWRWTHR TDSATNCYEG NKWDTSYCSD GPSCASKCCI DGADYSSTYG       100

ITTSGNSLNL KFVTKGQYST NIGSRTYLME SDTKYQMFQL LGNEFTFDVD       150

VSNLGCGLNG ALYFVSMDAD GGMSKYSGNK AGAKYGTGYC DSQCPRDLKF       200

INGEANVENW QSSTNDANAG TGKYGSCCSE MDVWEANNMA AAFTPHPC?V       250

IGQSRCEGDS CGGTYSTDRY AGICDPDGCD FNSYRQGNKT FYGKGMTVDT       300

TKKITVVTQF LKNSAGELSE IKRFYVQNGK VIPNSESTIP GVEGNSITQD       350

WCDRQKAAFG DVTD?QDKGG MVQMGKALAG PMVLVMSIWD DHAVNMLWLD       400

STWPIDGAGK PGAERGACPT TSGVPAEVEA EAPNSNVIFS NIRFGPIGST       450

VSGLPDGGSG NPNPPVSSST PVPSSSTTSS GSSGPTGGTG VAKHYEQCGG       500

IGFTGPTQCE SPYTCTKLND WYSQCL   *                             526
```

SEQ ID No. 2
DNA sequence and amino acid sequence of complete *Chrysosporium*
XylF (Xyl1) gene including promoter and terminator sequences.
Position of the protein encoding part of the gene is indicated in
bold with amino acid translation below the sequence. Promoter,
terminator and intron sequences are given in small case. The
signal peptide is shown in italic letters and the cellulose
binding domain (CBD) is shown in bold underlined letters.

```
tcatcaacttggcgtttggatgtactaatattacacgtcgtttgcnnagcggagtctgtg    60 tcatctccgtggggtcgggtgctccagacgacgcttcgggccgatcctgaattcgggaag   120 gaaacggttcggctaatcaggtcctctaaaatataacgaagcactacagagggagttcct   180 cagaggacatcgtatcaaccgaagaacgaagcgccgaaaggactgatcaaaacaggagta   240 ggtagggatgtgtgagtacctaaactttccatacctgacataaaatcatcatggtgcttc   300 agacctgtttgatgaggcgagggcggaggccgcattgtattttcgttccttccttctttt   360 tgttagtatatctnagggttccatcgtaaaatggaatcttccagctctactagtaattag   420 aacaatagttctgatgtcgtgcgccaagcttttcagatgactgccaaaaacccatcatg    480 ggtatggacaaaagcagtaatcggagtcacaacgccgcattttccttcatgatttccgtc   540
```

```
aaccggagaggtcggaggaggactccggccacatgtgatgcgaagaagtacatggcgcca    600 tggttctaacctcttatagtctgaaaatgcgcggaggccagcgaagccaagcccgggaac    660 cgttcttgtcatggtttcagtattgtttcgctaaacattctatccgattcgcgataggtg    720 cggctgccaccgaaggttgtatccttaaagctttggtaagtacggagtacggaaatggaa    780 acgcgccgcagtcctggttccatcggtatcctccgcatgctccgccaaaaaagaaaacc     840 cgggtatgtttacaaaggatataagagacaagatgcaccacccgccccttcccatctgc     900 cggttgcccacgtcgccgtcgactgcttgtccgcttcctacctgcagcctctttcagaga    960 ccatcaaacATGCGTACTCTTACGTTCGTGCTGGCAGCCGCCCCGGTGGCTGTGCTTGCC    1020
          M  R  T  L  T  F  V  L  A  A  A  P  V  A  V  L  A CAATCTCCTCTGTGGGGCCAGTgtatgtaattgccttactcggaaaatagtcaccactag    1080
 Q  S  P  L  W  G  Q  C agggacttaagctcactacttcctgtttcacaatagGCGGCGGTCAAGGCTGGACAGGTC    1140
                                      G  G  Q  G  W  T  G CCACGACCTGCGTTTCtGGCGCAGTATGCCAATTCGTCAAgtcagtaactgcttttatt    1200
 P  T  T  C  V  S  G  A  V  C  Q  F  V  N tcttttctctctgggattacgatttcgttttgcacttagcttggttctgcatttcattgt    1260 tgtattgttctcttttgtgtgtgagaggttttattaccacctaaaggccatttgctaac    1320 aaatctccccagTGACTGGTACTCCCAATGCGTGCCCGGATCGAGCAACCCTCCTACGGG    1380
             D  W  Y  S  Q  C  V  P  G  S  S  N  P  P  T  G CACCACCAGCAGCACCACTGGAAGCACCCCGGCTCCTACTGGCGGCGGCGGCAGCGGAAC    1440
 T  T  S  S  T  T  G  S  T  P  A  P  T  G  G  G  S  G  T CGGCCTCCACGACAAATTCAAGGCCAAGGGCAAGCTCTACTTCGGAACCGAGATCGATCA    1500
 G  L  H  D  K  F  K  A  K  G  K  L  Y  F  G  T  E  I  D  H CTACCATCTCAACAACAATGCCTTGACCAACATTGTCAAGAAAGACTTTGGTCAAGTCAC    1560
 Y  H  L  N  N  N  A  L  T  N  I  V  K  K  D  F  G  Q  V  T TCACGAGAACAGCTTGAAGTGGGATGCTACTGAGCgtgagtgacctctcctccttctccc    1620
 H  E  N  S  L  K  W  D  A  T  E  P gacaataatagataattacgagccggttcgaggctgacattgcgcgattctagCGAGCC     1680
                                                       S  R GCAATCAATTCAACTTTGCCAACGCCGACGCGGTTGTCAACTTTGCCCAGGCCAACGGCA    1740
 N  Q  F  N  F  A  N  A  D  A  V  V  N  F  A  Q  A  N  G  K AGCTCATCCGCGGCCACACCCTCCTCTGGCACTCTCAGCTGCCGCAGTGGGTGCAGAACA    1800
 L  I  R  G  H  T  L  L  W  H  S  Q  L  P  Q  W  V  Q  N  I TCAACGACCGCAACACCTTGACCCAGGTCATCGAGAACCACGTCACCACCCTTGTCACTC    1860
 N  D  R  N  T  L  T  Q  V  I  E  N  H  V  T  T  L  V  T  R GCTACAAGGGCAAGATCCTCCACTGGGACGTCGTTAACGAGATCTTTGCCGAGGACGGCT    1920
 Y  K  G  K  I  L  H  W  D  V  V  N  E  I  F  A  E  D  G  S CGCTCCGCGACAGCGTCTTCAGCCGCGTCCTCGGCGAGGACTTTGTCGGCATCGCCTTCC    1980
 L  R  D  S  V  F  S  R  V  L  G  E  D  F  V  G  I  A  F  R GCGCCGCCCGCGCCGCCGATCCCAACGCCAAGCTCTACATCAACGACTACAACCTCGACA    2040
 A  A  R  A  A  D  P  N  A  K  L  Y  I  N  D  Y  N  L  D  I TTGCCAACTACGCCAAGGTGACCCGGGGCATGGTCGAGAAGGTCAACAAGTGGATCGCCC    2100
 A  N  Y  A  K  V  T  R  G  M  V  E  K  V  N  K  W  I  A  Q AGGGCATCCCGATCGACGGCATCGGCACCCAGTGCCACCTGGCCGGGCCCGGCGGGTGGA    2160
 G  I  P  I  D  G  I  G  T  Q  C  H  L  A  G  P  G  G  W  N ACACGGCCGCCGGCGTCCCCGACGCCCTCAAGGCCCTCGCCGCGGCCAACGTCAAGGAGA    2220
 T  A  A  G  V  P  D  A  L  K  A  L  A  A  A  N  V  K  E  I TCGCCATCACCGAGCTCGACATCGCCGGCGCCTCCGCCAACGACTACCTCACCGTCATGA    2280
 A  I  T  E  L  D  I  A  G  A  S  A  N  D  Y  L  T  V  M  N ACGCCTGCCTCCAGGTCTCCAAGTGCGTCGGCATCACCGTCTGGGGCGTCTCTGACAAGG    2340
 A  C  L  Q  V  S  K  C  V  G  I  T  V  W  G  V  S  D  K  D
```

```
ACAGCTGGAGGTCGAGCAGCAACCCGCTCCTCTTCGACAGCAACTACCAGCCAAAGGCGG   2400
 S   W   R   S   S   S   N   P   L   L   F   D   S   N   Y   Q   P   K   A   A

CATACAATGCTCTGATTAATGCCTTGTAAgaggaggtatattattttagaggcaatgaa   2460
 Y   N   A   L   I   N   A   L   * gctaggaggaaagaggggaagtgaggtaattagctaggacaggcaaatctagcagcaatt   2520 ataagtcaacactatataaaatattcctataatggcttgtgcttcggtgtgcaaaaaaaa   2580 aaaaaaaaaaaaaaaaaaaaaaaaaaaaaactcaaaaacaaaaatgatccaacatgatt   2640 cgaaatggcgaccttgcaaatgcacacctcagataataccactatacaatacaccttaaa   2700 tggcacctaaatccatttgtctgcggtcatagacggggcttaagaagcctgggatgcagg   2760 tgtcgatgcaagggttacgtcagtgtatgatatgagtatgaaccatgctgtctgggtaat   2820 tctccactttccctcccttacgactcttcgggtgtgcctctctagaaagtcgactcctg   2880 gcgcctcagatcgcctttggctctgttcggtacaatgacgtccgctggtttcttccaaa   2940 gaccaggtatttctcccgtggcaacaaagaataccaaatacctatatcgaaccgtagtct   3000 tctgataattagatgtctctcaaggcgcgg                                 3030
```

SEQ ID No. 11
XylF protein sequence. Signal sequence is given in italic, the
CBD is underlined in bold.

```
  1 MRTLTFVLAA APVAVLAQSP LWGQCGGQGW TGPTTCVSGA VCQFVNDWYS

51 QCVPGSSNPP TGTTSSTTGS TPAPTGGGGS GTGLHDKFKA KGKLYFGTEI

101 DHYHLNNNAL TNIVKKDFGQ VTENSLKWDA TEPSRNQFNF ANADAVVNFA

151 QANGKLIRGH TLLWHSQLPQ WVQNINDRNT LTQVIENHVT TLVTRYKGKI

201 LHWDVVNEIF AEDGSLRDSV FSRVLGEDFV GIAFRAARAA DPNAKLYIND

251 YNLDIANYAK VTRGMVEKVN KWIAQGIPID GIGTQCHLAG PGGWNTAAGV

301 PDALKALAAA NVKEIAITEL DIAGASANDY LTVMNACLQV SKCVGITVWG

351 VSDKDSWRSS SNPLLFDSNY QPKAAYNALI NAL*
```

SEQ ID No. 3
DNA sequence and amino acid sequence of complete *Chrysosporium*
EG3 gene including promoter and terminator sequences. Promoter,
terminator and intron sequences are given in small case. Putative
glycosylation site is given with an asterisk (*). The signal
peptide is shown in italic letters and the propeptide is shown in
underlined letters.

```
ccgccctggagcgtggaccgtggggacaggcggcaaatgagaccctattggggcgcatcg    60 acggtgcagaaccgaggttccgggaccttggcagagcggcccagggaccccgccatccag   120 ctatgcgcctccacagaagccgaccgatgctcgggttgcatcccgagatcgtcggtatta   180 aggagaggggagaagaagaagggggggggggggggggaatgagacaacaacactcaggcg   240 cgccaattagaacttcaacgagcctccttcctgcatccagacaagaccgaggtcgagccg   300 ggtactatgcaagcgtcccgtgccgcgtgatgtcgctcgtaggtgttgacaggttctcag   360 ctgtttcttgaatcccggaggtggactaaaggggcaagagaccatggtaagctccgtc    420 gccagccctcccgttgcggagcggaagccgaggaccgaccttcttctggagaacccgggc   480 tgcccgggcggaggcgggttccgccttttttttaaccagtccgagttgttgtcgcgaact   540 gcgctcggttgcaacgtcagtgtccaatcggcaggcgtatcgcgacccggtaagggggtt   600 acggcatgtgttctcggcttccgcacatcaaaacttactcgtattcgtcctgaccttggt   660 aattaattatgtcgcaagacaaggagttgtttgagacgactccggcgcgcataattacac   720 agtggtgcagtattatatatctttctcccgtagggacgacgacaaagacccgtcagtgat   780 taataataattagtagcagtttctttctttcaagactcaagaatactcctttccgccatc   840
```

-continued

```
gtggcagcgtttagattcatcATGCAGCCGTTTCTGCTCTTGTTCCTCTCGTCGGTCACG    900
                     M  Q  P  F  L  L  L  F  L  S  S  V  T GCGGCGAGCCCCCTGACGGCGCTCGACAAGCGGCAGCAGGCGACGTTGTGCGAGCAGTAC    960
 A  A  S  P  L  T  A  L  D  K  R  Q  Q  A  T  L  C  E  Q  Y GGCTACTGGTCGGGCAACGGTTACGAGGTCAACAACAACAACTGGGGCAAGGATTCGGCC   1020
 G  Y  W  S  G  N  G  Y  E  V  N  N  N  N  W  G  K  D  S  A TCGGGCGGCCATCAGTGCACCTACGTCGACAGCAGCAGCTCCAGCGGCGTCGCCTGGCAC   1080
 S  G  G  H  Q  C  T  Y  V  D  S  S  S  S  S  G  V  A  W  H ACGACCTGGCAGTGGGAAGGAGGCCAGAACCAGGTCAAGAGCTTCGCCAACTGCGGCCTG   1140
 T  T  W  Q  W  E  G  G  Q  N  Q  V  K  S  F  A  N  C  G  L CAGGTGCCCAAGGGCAGGACCATCTCGTCCATCAGCAACCTGCAGACCTCCATCTCGTGG   1200
 Q  V  P  K  G  R  T  I  S  S  I  S  N  L  Q  T  S  I  S  W TCCTACAGCAACACCAACATCCGCGCCAACGTGGCCTACGACCTCTTCACCGCGGCAGAC   1260
 S  Y  S  N  T  N  I  R  A  N  V  A  Y  D  L  F  T  A  A  D CCGAACCACGCGACCAGCAGCGGCGACTACGAGCTCATGATCTGgtcagttttttttttc   1320
 P  N  H  A  T  S  S  G  D  Y  E  L  M  I  W tttttcttttcttctcttttcttttcttttcctttctcctgttttattttcttatccat   1380 tgcttcgccctctttccttaaccctgctgactctctcttcttgtcaatgatactgtaata   1440 gGCTGGCGAGATTCGGCGACGTCTACCCCATCGGCTCGTCCCAGGGCCACGTCAACGTGG   1500
  L  A  R  F  G  D  V  Y  P  I  G  S  S  Q  G  H  V  N  V

CCGGCCAGGACTGGGAGCTGTGGACGGGCTTCAACGGCAACATGCGGGTCTACAGCTTCG   1560
 A  G  Q  D  W  E  L  W  T  G  F  N  G  N  M  R  V  Y  S  F

TAGCGCCCAGCCCCCGCAACAGCTTCAGCGCCAACGTCAAGGACTTCTTCAACTATCTCC   1620
 V  A  P  S  P  R  N  S  F  S  A  N  V  K  D  F  F  N  Y  L

AGTCCAACCAGGGCTTCCCGGCCAGCAGCCAATACCTTCTCAgtaaggagacgagatctc   1680
 Q  S  N  Q  G  F  P  A  S  S  Q  Y  L  L  I gaacagcataccatatatgcgtgcggtacaagtgcactaaccccctttttttttcccgttc   1740 gcagTCTTCCAGGCGGGCACCGAGCCCTTCACCGGCGGCGAGACCACCCTTACCGTCAAC   1800
    F  Q  A  G  T  E  P  F  T  G  G  E  T  T  L  T  V  N AACTACTCTGCAAGGGTTGCTTAAacaggaaggccgaggatggccccaaggccgttgcg   1860
 N  Y  S  A  R  V  A  * ggttcacgagctctcttcttttcaagtgctgtacatacataattagcgtaccaagtcata   1920 gctgtttgtcagcttcaaactaagtgctcgcccacaaaagagggggagggaaaataac    1980 aaattgccgaacgcagtgataagcttctgggagcgttgaaagcagtctacagtaggtggc   2040 tgyacgaaggaaaagagtgccttattaaagctatctacaaaggagacaaaacgactgata   2100 tttatggacaaagggactggccaatgcgttaaacagcctcatacagctgtagcatatata   2160 tggctaatacgtttggaagctctatagcttccgacacacccctagttaaacgtagtagt   2220 cgtttaactacgctttgyggtgatactgttcttggtattatatccttttgtcgctcttacc   2280 tcgatagctccttcagggggcctgccttctgtattcggaagtctaaaagagtcgagtata   2340 gtagagcgattcctttaaagctatagatcaaatatggccattataactatagtagtaata   2400 gtattactagttttaatcataatagtaataataggatgacgcctcttatgcttgaatcaa   2460 tagatgactcgttaggtctacctattacaaacactataactgctagtaggtcgactcctg   2520 ctcctataacacctcgtaagtataagtatactaaagcttctataccgtaagtgttcctat   2580 tgtccctatttgattaactttattactagttttgtagttttcttagtagttctagcgatt   2640 taagcgagtttacgtggttcggcttcttctggttaatttgatagcgactctatcacagtt   2700 tctagcgctttactagtcacgtctagatcgttttaagctgactaaatatagcaacatcgaa   2760 gctagcgagctttgtaaggtacccctatagaatatatatacgtcggctctagtaggacgt    2820 tcttttagcaaatgtcacgatcattccggcgttagctcctactattactattataccctat   2880
```

```
agttcctataagtgtagggagatatacgttaatcgcctatacgtctaatagctcttataa    2940 tacttatactaactataatggtagtcttgcttcttatattaggtcggctaaggacttaac    3000 gaaggctctaatggatagagctaaggcttctataag                            3036
```

SEQ ID No. 12
EG3 protein sequence. Signal (prepro) sequence is given in
italic, the putative pro sequence underlined italic

```
  1 MQPFLLLFLS SVTAASPLTA LDKRQQATLC EQYGYWSGNG YEVNNNNWGK

51 DSASGGHQCT YVDSSSSSGV AWHTTWQWEG GQNQVKSFAN CGLQVPKGRT

101 ISSISNLQTS ISWSYSNTNI RANVAYDLFT AADPNHATSS GDYELMIWLA

151 RFGDVYPIGS SQGHVNVAGQ DWELWTGFNG NMRVYSFVAP SPRNSFSANV
                                                         *

201 KDFFNYLQSN QGFPASSQYL LIFQAGTEPF TGGETTLTVN NYSARVA*
```

SEQ ID No. 4
DNA sequence and amino acid of partial *Chrysosporium* GPD gene
including promoter sequences. Promoter and intron sequences are
given in small case. The 3' end of the gene is lacking.

```
tgagcagcaatgagcagcaatgagcattcctgggccaccgagtctgagtgccagtacgga     60 gtatcgtacttcgtaccggggtttgatttggtgacggtgcttttcacctctcgatgcccg    120 aaatcgggtctaagctgagtttgatcaaatatgtgactccaacatcgccccttcggcaa    180 accccgtcgacacgtgtgtcatccttccattgcaagcgatcactcgcagggcgtgacgat    240 gaacgagattttgcccggaccgattcgcggatatagcggcagccgaccagccctaccac    300 actgatggccgtgtcactagtgtatgctcccagaaccgcaagcatacactgggcaatgct    360 tggtatgcagttgaggcagctttatgtttccataccttccacttcggctcggggactcg    420 gcggggtcgcggaagtttgacggcagccgtcgggccttaggccgagattaccgtggttgt    480 ggcccagttttagccgttcccgtccgtttcctaccggaccatgattttcgtgaaccattg    540 caatcccgaagcgcatttccgacgttaaggagttacctccgctgcccagaattcatgatc    600 gtggccggctcaaggcagcgtggcggggcatccgtgtcaagctcccaggaggaggtgcgc    660 gatttcaaatccgggccaaaacaggccaagactggctggccaaaaaaaggagcgtagacg    720 gcccgggacatcggacgtcagctcgcagccacccaaaaccggtccgatctactcgcttac    780 tgtggtagttcaggtacttttgagtagtaaaaacgctacggcagggccggggggttcccc    840 ggtgacggaggtgcctctgcggtggcgaacatcccacgcactctcgagctacggtgacac    900 ctcgtgtcctgttggtcttgcaatgctgggcggcaggaaatgcgtcgcgctcctcccgg    960 ccaagacctaaaacagacagcgccgcaaagtcgctcactagcaccgcgaaacgaagatgc   1020 cccacctcaacgcaatctgtgatgcaagcaattgggaaggctcaccccacctcagcgagg   1080 ggctcaaccattttattatcagctcatgccaccacaacatgactgttttctttccttgc   1140 tcatcccacatttgacaaaaatcgtcgattaatctctttccatacaggccgtccgcgctc   1200 tgataaccacataaaagtctcttcagtcaacagctcaaagctccctcatccctccaggta   1260 agcagccaaagagctcccccacggaccccgcactgcctcatcccgcctgtatcggacctg   1320 cgcgacccagcagagaatcccaaacctttgctgcttgctgcccggttccggactgagctg   1380 caacccaagcctttaaaaagcttttcccttctcccacggtgtcaactctgtcctatccct   1440 ccgacatccgttgagctcaacaactccccgaaccttttaccccgcgccgagctaccccctc   1500 catcaaaccaccctgacagctcgctcactcacctccccacatcacagaaatcaaaATGAC   1560
                                                          M  T TATCAAGGTCGGCATCAACGGTTTCGGCCGTATCGGCCGTATCGTCTTCCGCAACTCCAT   1620
 I  K  V  G  I  N  G  F  G  R  I  G  R  I  V  F  R  N  S  I
```

```
CGAGCACTCGGATGTCGAGATCGTTGCCGTCAACGACCCCTTCATTGAGCCCAAGTACGC 1680
 E  H  S  D  V  E  I  V  A  V  N  D  P  F  I  E  P  K  Y  A   -

Tgtaagtagttttttttttccttcctcgcgttctttcctgttccatcgacagtacgagat 1740

GatcttgcaggcggatcggagctaaccgcgattgtcgtacagGAGTACATGCTCAAGTAT 1800
                                            E  Y  M  L  K  Y   -

GACTCGACCCACGGTATCTTCAACGGCACCATCGCCGTCGAGGGCAACGACCTCATTGTC 1860
 D  S  T  H  G  I  F  N  G  T  I  A  V  E  G  N  D  L  I  V   -

AACGGCAAGAGGGTCAAGTTCTACACTGAGCGGGMCCCCGCCAACATTCCCTGGARGGAA 1920
 N  G  K  R  V  K  F  Y  T  E  R  ?  P  A  N  I  P  W  ?  E   -

ACTGGTGCCGAGTACATMRTCGAGTCGACCGGTGTGTTCACCAMCACCSAGAAGGCTAGC 1980
 T  G  A  E  Y  I? E  S  T  G  V  F  T? T? K  A  S             -

GCCCACCTCAAGGGCGGCGCCAAGCGCGTCATCATCTCTGCTCCCTCGGCCGATGCCCCC 2040
 A  H  L  K  G  G  A  K  R  V  I  I  S  A  P  S  A  D  A  P   -

ATGTACGTCATGGGCGTCAACGAGAAGACCTACGACGGCAAGGCCCAGGTCATCTCTAAC 2100
 M  Y  V  M  G  V  N  E  K  T  Y  D  G  K  A  Q  V  I  S  N   -

GCCTCGTGCACCACCAACTGCCTGGCTCCCCTCGCCAAGGTCATCCACGACAAGTTCGGC 2160
 A  S  C  T  T  N  C  L  A  P  L  A  K  V  I  H  D  K  F  G   -

CTCGTTGAGGGTCTCATGACCACCGTCCACTCCTACACTGCCACCCAGAAGACCGTCGAT 2220
 L  V  E  G  L  M  T  T  V  H  S  Y  T  A  T  Q  K  T  V  D   -

GGTCCCTCTGCCAAGGACTGGCGTGGTGGCCGTGGTGCTGCTCAGAACATCATCCCCAGC 2280
 G  P  S  A  K  D  W  R  G  G  R  G  A  A  Q  N  I  I  P  S   -

AGCACTGGCGCCGCCAAGGCCGTCGGCAAGGTCATCCCTGAGCTCAACGGCAAGCTCACC 2340
 S  T  G  A  A  K  A  V  G  K  V  I  P  E  L  N  G  K  L  T   -

GGCATGTCCCTCCGTGTCCCCACCCCCAACGTTTCCGTTGTCGACCTCACCTGCCGCCTC 2400
 G  M  S  L  R  V  P  T  P  N  V  S  V  V  D  L  T  C  R  L   -

GAGAAGGAGGCTACCTACGACGACATCAAGGCCGCCATCAAGGAGGCCGCCGCCGGCCCC 2460
 E  K  E  A  T  Y  D  D  I  K  A  A  I  K  E  A  A  A  G  P   -

CTCAAGGgtgagttatctggttccttttttttttttggagaacgacacatgctgataaa  2520
 L  K  G acccagGCATCCTCGACTACACTGAGG                                   2547
       I  L  D  Y  T  E SEQ ID No. 13
GPD protein sequence (the C-terminus is lacking in the sequence
available).
MTIKVGINGF GRIGRIVFRN SIEHSDVEIV AVNDPFIEPK YAEYMLKYDS

THGIFNGTIA VEGNDLIVNG KRVKFYTER? PANIPW?ETG AEYI?ESTGV

FT?T?KASAH LKGGAKRVII SAPSADAPMY VMGVNEKTYD GKAQVISNAS

CTTNCLAPLA KVIHDKFGLV EGLMTTVHSY TATQKTVDGP SAKDWRGGRG

AAQNIIPSST GAAKAVGKVI PELNGKLTGM SLRVPTPNVS VVDLTCRLEK

EATYDDIKAA IKEAAAGPLK GILDYTE

SEQ ID No. 5:
C1-EG5 "25 kD" (Family 45) gene obtained by PCR based on
"25kD Endo" protein sequencing and family 45 homology analysis.
-3309                                              GCTTAGGAG  -3301

AATCACGAGAAGCTAATTGGGCTCTATAGTATCCGACAAGATGACCCAGAGCGAGATTGA -3241

GGATCTCGAGGGAACCCTGAAGCAGAGCAGCAACAACGACACCAGCCTCCTCCGCGACCT -3181

GCTCGACAAGATTCCCGATGGCCTCCTCGGCGGCAACAACAAATCCAAGCTGGACGATAT -3121

CCAGAGCAACGCGCAGGCCGCGCAGATGGAGAACCTGAGCGTCTCGCCGCGGGAACCCGA -3061

GGAGCTGACCAGATACGTCCAGGAAGTGTTCCGTCAGATCATGCCCGCCATCAAGTTCCA -3001

TGACCAGCTTCTCCAGGACATCTCGGAGGCCATCGACAAGATCCCGGTGCTGCCCAAGAT -2941

TGTGGAGCAGCTGGAGGAGCAGATGTCCATCTTTGTATTCCAGATCATGGCCCCGTTCGT -2881
creA
```

```
GGTTCCGCTTATCGAGCAGATCAAGAACGAGCTCGCGACTGGCTCCAGCGAGATCATCCA   -2821

GAGCAGCAGGGCTGAGCAGCACAACGTCTTTGAGGACGACAACGCCACCGACCCGACTCA   -2761

CTCGATGTTGGCCAAGGACCACTTTAGTAACGTAAAGCCGACCCTAATCAGAAGCTCGCA   -2701

TGTAGAATTGAGTTAGACTGACGCGACTTGTTTCCCGTCTCTGTAGATCCTCAACGAGAT   -2641

CGGCGGTCGCGCCGCCTCCAAGGTCGTCTCCTGGGTCGTCCCGCAGCTCATGGAGGCCTG   -2581

GGACGATGACAGCGTCGACGTGGACCGCCTGCTTGACAAGATCATTTACGGAGTGTTCCA   -2521

CCATCCCGCGCAGCGCACCATGGGCCCTGAGGGGCGTCCGAGGGCCGGGAGCTCATCTT   -2461

CAACATGGTGCGCGAGTGGTGGGAGGACATGAGCGACGGGCAGCGCGACGAGTACCGGGG   -2401
creA

CAAGCTGAGCCGCGAGGGAGTCGAGAGAGGCGACAACCACCGCGAGGGCCAGCACGACTG   -2341

CGGCCACGGCTGCGGGGGCAAGCTCAAGATGCACAAGAACTTCCGGAACGAGGCGCCCCA   -2281
creA

GACGGTAGAGGACCAGATCGCGGGCGCCGCCGCGGAGGCCATCATGGGAGGCGTCAAGCA   -2221
creA

GGGCCTGTCGCAGGCCGTGCAGAACGCCGCCGGCCGCCAGGAGTCGTCGGAGAGCAGCGG   -2161

CCTGGGTGGGTTCATCAGCAGCGTCGCGGGCGGCCTCCTGGGCGGCGCCCTCAAGAGGGA   -2101

CGAGACAGAGTCGTACCAGGCCGGCGGCCGCACCGAGGACGGCGGGTACACGCAGACCAC   -2041

GACCGAGTACGGCTACTCCGGAGGCCGCTACGGCCAGGCCCAGTACACGGAGACGCAGTA   -1981

CGGCGGCGGCGGCGGCCGCAGCGAGTACCGCCGCTACGAGCAGCGCGAGGATGATGA     -1921

CGGCCGGGTCCAGAGCTACGGATACACGGAACAGCGCACCGAGACGCGCTACGACAGCTA   -1861

CTCGGGTGGCTATGGCGGCCGCGAGGAGACCAGCAGCTATGGCGGCGGCGGCAGCGCGAG   -1801

CGAATACATTCGTAGCTCCCAGCAGAGTAGCTACGGTGGCAGCGGCTATGGCAGTGGGTA   -1741

CGGTCGTCGTGATGAAGAAGAGAGCAGCGGCTATGGAAGTGGTTACGGTCGTCGTGATGA   -1681

AGAGGAGAGTGGTGGTTATGGTGGCGGCTATGGCCGCCGTCAGGAAGAAGAGAGTAGCAG   -1621

CTATGGAAGCGGTTATGGTCGTCGTCGTGATGAAGAAGAGAGCGGCGGTTATGGTGGTGG   -1561

CTACGGCCGCCGTCAGGAAGAAGAGAGTAGCGGCTATGGAAGTGGTTACGGTCGTCGTGA   -1501

TGAAGAAGGGAGCGGCGGTTATGGTGGTGGCTACGGCCGCCGTCATGAGGAAGAGAGCAG   -1441

TGGTTACGGCAGCGGCTATGGTCGTCGCCATGAAGAGGAGGGCGGTGGCTACGGCAGTGG   -1381

TTACGGCCGCCGGCGCAACGACGAGGAGGAAGAGGAGGATGGCGGACGCCGGAGGTGGGG   -1321
creA

TTACTAGGGTGAACTCTTCCGGCCGGTCTCTTGTTGTGAACCTTGCTGTTGCATGGGCAG   -1261

GACCGGTGCATCATGAACAGGACGGTGCGCTGTGTTTTTTTTTCTCGGGGTCTTGATTG   -1201

TTTGTTGAATCTCCCTTTTCGAGGATACGAGCTCTCTCGGGGACGAATAGATGAAGGCAA   -1141

TCTGACAGATTTGCTCTCAAAAAAGACTGATATCTCTTCCACCATGCACTGTATGTACA   -1081
nit2

TTACATACATTATCCCCCTCCACTGGATTCGCACAACGGAAAGCAATGGCGCGCTGATTC   -1021

AAGAACCATCAGGGCTGTCATTGGCTTGTTTTGTGCCGTGGCCGCGGTGACGCCCACTAT   -961

GACTCTCTGGGCAGGCGGCAACTGGGTGCCAGATATATTAATCCGGGGCATAGCGCATAT   -901
creA

CTTCCTTGATTTGTAGAGTACTAGTACACTAACCCCCTTCTCCACATGGGGCCACTGTTC   -841
nit2

GGTAGATCTGCCCGAAGTGCAAGTGCGGGGGGGCCAAACTAGGTAATATCCTCCCGCTC   -781
creA

TCCCGAGTGCGCGGACTAACCGTCATTGCTCCCAGAGGCTTGCACTCTATCGCAGGCCTT   -721
nit2
```

-continued

```
TTCCAATAAGGATGGGGCGTTCGGCGGTGATGATGCCGGTCGTGCGGGGCATACGGGGAG    -661
creA

GGTAGATAGAAAATAACGACGCTGGTGTTTTGGAGAGGGGAGGGGGACTATTAGGGGAGG    -601
creA   nit2

GAAATACAGGGGCAGGGGGTGAGACGGGTGACGTTCCGGCGGAACCTCGCGCTTGTCAAA    -541

CAAGCAGCCCTGTTAGGTTGCTCTAGACTAGTGTACATACATACATATGTACATACTGTA    -481

TGTACTGCACATACTTTAACTTGGTGCTTCCCTGTGAGCCGCCAGGAACATCACAACTGC    -421

AAGCGGAAAAGGCCCCATATACGGGGCGGCTTGTCGGGATGGCTCCCCCCTTCGGAACGG    -361

GTCTGACTTCCGAGGATTTTACCTGCTTCATTTGGGTATTCTGCGATGGCCTGTTCAACC    -301

CTTCCCCTGGCCGAACCGTTTCTTGGCTCGATCCTAGTGTACACTACACTACTCGTAGAC    -241

TGCCTGCCCGACGATCCGCGGGAACGGGCCAGGAGTGTGGAGTGGAGACGGGCGGCGGTG    -181
creA

ATGTCGTGTAATTAAATATATAAGTGAGAGTGTTTTTTGACTGCCCCGGGTTCTGGTAGT    -121
TATA box

TGAAGGGAAGTTCGATGCTCTCTGCTGTCGTCGCTCTCGTCGCTCTCGTCGGCATCCTCC     -61

ATCCGTCCGCCTTTGATAACCCGCTCCCCGACTCAGTCAAGACGACGCATACTTGGCACC      -1

ATGCATCTCTCCGCCACCACCGGGTTCCTCGCCCTCCCGGCCCTGGCCCTGGCCCAGCTC    +60
Put.SS
 M  H  L  S  A  T  T  G  F  L  A  L  P  A  L  A  L  A  Q  L      20

TCGGGCAGCGGCCAGACGACCCGGTACTGGGACTGCTGCAAGCCGAGCTGCGCCTGGCCC   +120
 S  G  S  G  Q  T  T  R  Y  W  D  C  C  K  P  S  C  A  W  P      40

GGCAAGGGCCCCTCGTCTCCGGTGCAGGCCTGCGACAAGAACGACAACCCGCTCAACGAC   +180
 G  K  G  P  S  S  P  V  Q  A  C  D  K  N  D  N  P  L  N  D      60

GGCGGCTCCACCCGGTCCGGCTGCGACGCGGGCGGCAGCGCCTACATGTGCTCCTCCCAG   +240
 G  G  S  T  R  S  G  C  D  A  G  G  S  A  Y  M  C  S  S  Q      80

AGCCCCTGGGCCGTCAGCGACGAGCTGTCGTACGGCTGGGCGGCCGTCAAGCTCGCCGGC   +300
 S  P  W  A  V  S  D  E  L  S  Y  G  W  A  A  V  K  L  A  G     100

AGCTCCGAGTCGCAGTGGTGCTGCGCCTGCTACGAGCTGACCTTCACCAGCGGGCCGGTC   +360
 S  S  E  S  Q  W  C  C  A  C  Y  E  L  T  F  T  S  G  P  V     120

GCGGGCAAGAAGATGATTGTGCAGGCGACCAACACCGGTGGCGACCTGGGCGACAACCAC   +420
 A  G  K  K  M  I  V  Q  A  T  N  G  G  D  L  G  D  N  H        140

TTTGACCTGGCCgtgagttgcctcccttctccccggaccgctcagattagatgagatta   +480
         Intron 1
 F  D  L  A                                                      144 gactttgctcgtaaatcggtccaagattcccttgactgaccaacaaacatcatacgggca   +540 gATCCCCGGTGGCGGTGTCGGTATTTTCAACGgtaagctggtgccccggaccccctccc   +600
                             Intron 2
 I  P  G  G  V  G  I  F  N                                      154 ggaccccctcccccttttcctccagcgagccgagttgggatcgccgagatcgagaactcac   +660 acaacttctctctcgacagCCTGCACCGACCAGTACGGCGCTCCCCCGAACGGCTGGGGC   +720
                    A  C  T  D  Q  Y  G  A  P  P  N  G  W  G    168

GACCGCTACGGCGGCATCCATTCCAAGGAAGAGTGCGAATCCTTCCCGGAGGCCCTCAAG   +780
 D  R  Y  G  G  I  H  S  K  E  E  C  E  S  F  P  E  A  L  K     188

CCCGGCTGCAACTGGCGCTTCGACTGgtacgttgctttgacataccggaacccaattcct   +840
                         Intron 3
 P  G  C  N  W  R  F  D  W                                      197 ccaaccccccccttttctcccccaactccgggggtagtcggaatgtcgcgactgaccct   +900 atttcagGTTCCAAACGCCGACAACCCGTCGGTCACCTTCCAGGAGGTGGCCTGCCCGGT   +960
        F  Q  N  A  D  N  P  S  V  T  F  Q  E  V  A  C  P       214

CGGAGCTCACGTCCAAGAGCGGCTGCTCCCGTTAAGAGGGAAGAGAGGGGGCTGGAAGGA  +1020  t25
 S  E  L  T  S  K  S  G  C  S  R  *                              225
```

-continued

```
CCGAAAGATTCAACCTCTGCTCCTGCTGGGGAAGCTCGGGCGCGAGTGTGAAACTGGTGT  +1080  t85

AAATATTGTGGCACACACAAGCTACTACAGTCCGTCTCGCCGTCCGGCTAACTAGCCTTG  +1140  t145

CTGCGGATCTGTCCATCTTCGGTCCGAACTGTCCGTTGCTGTTTTGGCTCGGTGCCTCAT  +1200  t205

CTTCTCCCAACCTAGTCAAGAATGAATCGTGAGAGAGGCTGAGAGAGATAAGATCGACTT  +1260  t265

CAGAAATCCAGGGTTGAAAGCAATAAAAAAATTCCTGTGGGATGAATATCTCGTGATGC   +1320
polyA site

AACGACCCTCCTAGGAACCTTGACGAAATTTGCTGACGGCAAATTCTTCAAAGACTCGT  +1380  t385

TAACCGGTCGCCCGTAGTGGTCCTGTTGCCCCAATCCGTTTGTGTTGAAATGACATTGCG  +1440  t445

CGTAACGCCGGACTCATATCAACTGCGTACCGAAAGCCAATCCCTCCCCAAACACGCCCT  +1500  t505

CTCTAATAAGCTCTCCCAAACAAGACCTCTTGAGACAGAAAATACGCCCAGATGCTGAGG  +1560  t565

ACTTGACAAGCCGGGGGGGGGGGGGCTTGTCAAGTGCAAAACTTGCCCATTTCATGC    +1620  t625

TGGTATCAAAAACAAAAAAAAAAAAAAACATTTCAAGTCGCGGATGCCCCATTTACAT   +1680  t685

TGCTTGCGTGCGCCAATAGAAACTTGCAACACGTCAGTGTCATCTTGCACGCCTTGG    +1737  t742
```

SEQ ID No. 14
C1-EG5 "25 kD" Protein sequence
MHLSATTGFL ALPALALAQL SGSGQTTRYW DCCKPSCAWP GKGPSSPVQA CDKNDNPLND

GGSTRSGCDA GGSAYMCSSQ SPWAVSDELS YGWAAVKLAG SSESQWCCAC YELTFTSGPV

AGKKMIVQAT NTGGDLGDNH FDLAIPGGGV GIFNACTDQY GAPPNGWGDR YGGIHSKEEC

ESFPEALKPG CNWRFDWFQN ADNPSVTFQE VACPSELTSK SGCSR

SEQ ID No. 6:
C1-EG6 "43 kD" (Family 6) was obtained by PCR based on "43 kD Endo" protein
sequencing and family 6 cellulases homology analysis.

```
-2508      GGATCCACACCTACCATACCGGATAGTATGCTACCCAAGTGACATAGG  -2461

GTTGGTAAAGTAATACGAGAACTCAGAGAGCACTGCCCATATGGCTCGCCAATGACCTCA  -2401

AGTGCCAGGTCAGCTTTGCGAGACAGACCTGAGCGCGTCGGATGTGTGACATGGAACGCG  -2341

CCGGATCGCCTTGTTGATTAATTATAGGGAAGTAGCGAGGAAGGTTTCAGCAATTGACGT  -2281

GAGCGTACATTAAAAGCTGTATGATTTCAGGAAGACGAGCCATGGACCAGGTTTCAAGGC  -2221

TGAATGGCTTGACGACTTAAGCACCGAACGAGGAATGAAAGAATGAAAAGTGGGGGATCA  -2161
creA

TTCTGGCCCCTCCTCGTATGTCGAGTGTTAAAGAAGGCGGTTCTACGGAGGACCTAAAGA  -2101

GCTCCAATTTGCTCTGTTGAGCTTAAGCCACATATCTCAAGATGAATACATGTCAGGCAT  -2041

AGTCACCCTGATCTTGTTCATCAGTCCACACACTTTTCAGTTCAGCATGTTGATTCCTCA  -1981

TCCATATCACTTTCCATTACTATCTCTTTATGTCCTTGGTCAAGACTCCAAGGAACCGAT  -1921

AGGTGAGCATCGGTGAGGCTCCCTCAAGGTACCAAAGTAGCCATCATCACCGAGGTCTGG  -1861

GAATGGCGCCGTGCCCGATCTGAGTCCTCCAACTCCACGGTACGACGACAGCACGTCACA  -1801

TTGACGCACCACGGTTGAACAAGCAGAGAGGGACACGTCTTGCTACGCGAATCCTGGCAC  -1741

TGGATGGAGACGCGTGTGAGCAGGTTTCCGGAACCATGACGGCCTGGTCCGGCTTCTCGA  -1681

ACAAAGAAGTGGAACACAAAAAGAACCGAAACGGAAACGCAGGCACGGCATCGACGACCG  -1621

GATTGTCCCACGGGGACCTCGGCCAGTCAAGCGTTGCCCTGGCCGTCAGCTCCCTGGCGA  -1561

CGGGGATTCAGCACATCTCACGTTATAGGCGACCTCATCCCCCTTCCGTCTTGTGCGGTC  -1501

GTTGCTCCGTGCCGAGTACCCAGGCGTGCCGGGGCCTTTAGCCGGGGCGGAATCAGAGTC  -1441
creA

AAGATGCGGCCGAATTGGACGGCAGACGAAGTTTCGTAGAGGGTCATGATCGGCACTGAC  -1381

GACACCCACCCCTGCGTGATCCCGTGGCCCTGGGCTGGGAATTGCCGGCTAATAATCTAC  -1321
```

```
GGCTTAATAGATATGCACTTTGCACGCGGTGCAGATAAATAAGCTGTGGTTTCAAACACT      -1261

GGCCTCCGTACTTTACCCACCAACTGCCGCTTAGCGCCGGGACCTGAGTCTTGGGAGTGC      -1201

GCGGAGCGGCAGCCACCTCGGGTTAGCGTACACACGACGGCTGCATGCGGGGATGCCGCG      -1141
creA

TGCATGGCTTCATAGTGTACGACAGACCGTCAAGTCCAAATCTGGGTGATGCTTGATGAG      -1081
creA

ATGACAGCGAGCCCCGTCGGCGGCACCCCGGCTATGCATCGCGAATTGACAACACTCTCA      -1021

GCTCTATTGCGACCCATCGGATAAAAGAAGAAGAAAAAAATGGACCTTGAGTACGGGCGT       -961

CAGAAACCAAAAAAAAACTCCGGAACCAAATATGTCGGGCATGGCCGGGGTGAACGACCG       -901

CTACTCCCCGTTCCCTTCTTCGCAAACAGAACGCTACAGAGGGTTTTCTGGTTTGTCAAA       -841

GAGTTCGGAGGTCCTCTGCTCCGCGAATGCGTGGTGAACCCACCAGCAGCCATTGTTCTT       -781

GCATGCGTGGCGGACCGTTAGCCGCTGATCGACATGGCGAGCTTCCCACCTCAGACCTGG       -721
creA

AGCAGACGGTTGCGAGGAGCAAGGGGCTGCCCTCCCCCTGACGGTCGGACCCCAATGACT       -661

TCCCCAAACGGGGACATCGAGGGTCGTGCATGATGGTGGAAAGTAGTTGCAGTATGGGAA       -601

GTACCCCGGGTTGCCAGGAACCGTTGTTCGGCCCCCCACATTTTCTCTCTGCCATGTCAA       -541

CTGTGTGTCGTTCGAGAGTTCCTGGCTCCGGCCCCCCGTCCAATTCCCTAACGGGACCGC       -481
creA

GGGGCATCGCCTGTAACTAACTTCCAAATGAAGCCGGATATGAGGGAGGGAGATTGGATC       -421

TGGCAAGCCAGCCATTCGCTGCGATCGGCACTCGTCCGTCAGCCCCGCAGTCCATATCCC       -361
areA

CAAAGGCAACTGCTCGGCGCGGCTCAAGTCTTCTTCGGAACGTCCAGCCCGAAGGCGCGC       -301

GCCAGCACCGGCCCTATGTTCCTGATTGCGATCCTCGATCTCCAGAGACGGGTCACCTCG       -241

CCTCGAGGACGGTGCAGGGGCATCGGCTTCGCTTCCTAGAGCTCCGGGCTGTGTGTGGTC       -181

AAGGGGAGAAGGCGGCGGCGCCAAGGTGCGTCTCGGCGCACTCACCCATCGCCTTTACCC       -121

CCCTCCCCCCCAGTATATAAAGATGGCCATCGTCTCCTCGTCTGCTTGGGAAGAAAGGA        -61

TCTCTCGACCATGCACCACAGCCTAGCTCTAACCCAGCTTGTCGTGTGTTGTTGCCCAGC        -1
transc.ini.
ATGAAGTTCGTGCAGTCCGCCACCCTGGCGTTCGCCGCCACGGCCCTCGCTGCGCCCTCG       +60
Putative Signal Seq
 M   K   F   V   Q   S   A   T   L   A   F   A   A   T   A   L   A   A   P   S      20

CGCACGACTCCCCAGAAGCCCCGCCAGGCCTCGGCGGGCTGCGCGTCGGCCGTGACGCTC      +120
 R   T   T   P   Q   K   P   R   Q   A   S   A   G   C   A   S   A   V   T   L      40

GATGCCAGCACCAACGTGTTCCAGCAGTACACGCTGCACCCCAACAACTTCTACCGTGCC      +180
 D   A   S   T   N   V   F   Q   Q   Y   T   L   H   P   N   N   F   Y   R   A      60

GAGGTCGAGGCTGCCGCCGAGGCCATCTCCGACTCGGCGCTGGCCGAGAAGGCCCGCAAG      +240
 E   V   E   A   A   A   E   A   I   S   D   S   A   L   A   E   K   A   R   K      80

GTCGCCGACGTCGGTACCTTCCTGTGGCTCGACACCATCGAGAACATTGGCCGGCTGGAG      +300
 V   A   D   V   G   T   F   L   W   L   D   T   I   E   N   I   G   R   L   E     100

CCCGCGCTCGAGGACGTGCCCTGCGAGAACATCGTGGGTCTCGTCATCTACGACCTCCCG      +360
 P   A   L   E   D   V   P   C   E   N   I   V   G   L   V   I   Y   D   L   P     120

GGCCGTGACTGCGCGGCCAAGGCCTCCAACGGCGAGCTCAAGGTCGGCGAGCTCGACAGG      +420
 G   R   D   C   A   A   K   A   S   N   G   E   L   K   V   G   E   L   D   R     140

TACAAGACCGAGTACATCGACAgtgagttaaccctttgtggcccctccttttcccccgag      +480
               Intron 1
 Y   K   T   E   Y   I   D                                                        147 agagcgtctggttgagtggggttgtgagagagaaaatggggcgagcttaaagactgacgt      +540 gttggctcgcagAGATCGCCGAGATCCTCAAGGCCCACTCCAACACGGCCTTCGCCCTCG      +600
             K   I   A   E   I   L   K   A   H   S   N   T   A   F   A   L     163
```

-continued

```
TCATCGAGCCCGACTCGCTCCCCAACCTGGTCACCAATAGCGACCTGCAGACGTGCCAGC  +660
 V   I   E   P   D   S   L   P   N   L   V   T   N   S   D   L   Q   T   C   Q         183

AGAGCGCTTCCGGCTACCGCGAGGGTGTCGCCTATGCCCTCAAGCAGCTCAACCTCCCCA  +720
 Q   S   A   S   G   Y   R   E   G   V   A   Y   A   L   K   Q   L   N   L   P         203

ACGTGGTCATGTACATCGATGCCGGCCACGGTGGCTGGCTCGGCTGGGACGCCAACCTCA  +780
 N   V   V   M   Y   I   D   A   G   H   G   G   W   L   G   W   D   A   N   L         223

AGCCCGGCGCCCAGGAGCTCGCCAGCGTCTACAAGTCTGCTGGTTCGCCCTCGCAAGTCC  +840
 K   P   G   A   Q   E   L   A   S   V   Y   K   S   A   G   S   P   S   Q   V         243

GCGGTATCTCCACCAACGTGGCTGGTTGGAACGCCTGgtaagacactctatgtccccctc  +900
 R   G   I   S   T   N   V   A   G   W   N   A   W                                     256
                                          Intron 2 gtcggtcaatggcgagcggaatggcgtgaaatgcatggtgctgacctttgatctttcccc  +960 cctcctatagGGACCAGGAGCCCGGTGAGTTCTCGGACGCCTCGGATGCCCAGTACAACA  +1020
           D   Q   E   P   G   E   F   S   D   A   S   D   A   Q   Y   N           272

AGTGCCAGAACGAGAAGATCTACATCAACACCTTTGGCGCTGAGCTCAAAGTCTGCCGGCA +1080
 K   C   Q   N   E   K   I   Y   I   N   T   F   G   A   E   L   K   S   A   G        292

TGCCCAACCACGCCATCATCGACACTGGCCGCAACGGTGTCACCGGTCTCCGCGACGAGT  +1140
 M   P   N   H   A   I   I   D   T   G   R   N   G   V   T   G   L   R   D   E        312

GGGGTGACTGGTGCAACGTCAACGGCGCCGGCTTCGGTGTGCGCCCCGACTGCCAACACTG  +1200
 W   G   D   W   C   N   V   N   G   A   G   F   G   V   R   P   T   A   N   T        332

GCGACGAGCTCGCCGACGCCTTCGTGTGGGTCAAGCCCGGTGGCGAGTCCGACGGCACCA  +1260
 G   D   E   L   A   D   A   F   V   W   V   K   P   G   G   E   S   D   G   T        352

GCGACTCGTCGGCGGCGCGCTACGACAGCTTCTGCGGCAAGCCCGACGCCTTCAAGCCCA  +1320
 S   D   S   S   A   A   R   Y   D   S   F   C   G   K   P   D   A   F   K   P        372

GCCCCGAGGCCGGTACCTGGAACCAGGCCTACTTCGAGATGCTCCTCAAGAACGCCAACC  +1380
 S   P   E   A   G   T   W   N   Q   A   Y   F   E   M   L   L   K   N   A   N        392

CGTCCTTCTAAGCTCCTCGACGGCTTCTTGCTGTCAGTCGCTCTGACGGTGGTGTGCTGG  +1440  t49
 P   S   F   *

TGGTGCCCCTGCTCCTGCTGCTGCTCCGCGGGGAGGGGAGGCAACGAAAATGAAGTC     +1500  t109

CTGCTTCAAAACAAAACAGAAACAAGCGAGGCGCGGTGCAATGGTCGTGCGTTCGTCTTT  +1560  t169

TTTCATGTTCCCTTCTAGTGTAGTAGTTTGATAGTCGTACATAAGGGGTTTCAGAACCGT  +1620  t229

CTCTCTGTCTCGGTCTTTTTGCGAGTTGTTGCGACTCGTGATTATGGCCTTTGTTGCTCG  +1680  t289

TTGCGGCAGAGTAGAACCACAGCGTGTTGGGGTAGCAGCTTGCTCCGTAGGACGTAGGGA  +1740  t349

AACAACCTGAGACTCTGGAATTGCAGTCAGCCTGCGTCGCCCCTCTAGGAAACGAAGGGG  +1800  t409

AGAACCAGTAGTGGCTGCAGCTTACAAACGCGAGCATGGTGAACATCTCCGAGAAAGGG   +1860  t469

AGGGATCC                                                      +1868  t477
  BamHI
```

SEQ ID No. 15
C1-EG6 "43 kD" Protein sequence
MKFVQSATLA FAATALAAPS RTTPQKPRQA SAGCASAVTL DASTNVFQQY TLHPNNFYRA

EVEAAAEAIS DSALAEKARK VADVGTFLWL DTIENIGRLE PALEDVPCEN IVGLVIYDLP

GRDCAAKAGN GELKVGELDR YKTEYIDKIA EILKAHSNTA FALVIEPDSL PNLVTNGDLQ

TCQQSAGGYR EGVAYALKQL NLPNVVMYID AGHGGWLGWD ANLKPGAQEL ASVYKSAGSP

SQVRGISTNV AGWNAWDQEP GEFSDASDAQ YNKCQNEKIY INTFGAELKS AGMPNHAIID

TGRNGVTGLR DEWGDWCNVN GAGFGVRPTA NTGDELADAF VWVKPGGESD GTSDSSAARY

DSFCGKPDAF KPSPEAGTWN QAYFEMLLKN ANPSF

SEQ ID No. 7 (DNA) and SEQ ID No. 16 (protein):
Chrysosporium xylanase F (partial)
```
TGACCTTCTCCTCCTTCTCCCGAACAATAATAGATAATTACGAGCCGGTTCGAGGCTGAC    1

ATTGCGCGATTCTAGCGAGCCGCAATCAATTCAACTTTGCCAACGCCGACGCGGTTGTC    61
                S   R   N   Q   F   N   F   A   N   A   D   A   V   V
```

```
AACTTTGCCCAGGCCAACGGCAAGCTCATCCGCGGCCACACCCTCCTCTGGCACTCTCAG  120
 N   F   A   Q   A   N   G   K   L   I   R   G   H   T   L   L   W   H   S   Q

CTGCCGCAGTGGGTGCAGAACATCAACGACCGCAACACCTTGACCCAGGTCATCGAGAAC  180
 L   P   Q   W   V   Q   N   I   N   D   R   N   T   L   T   Q   V   I   E   N

CACGTCACCACCCTTGTCACTCGCTACAAGGGCAAGATCCTCCACTGGGACGTCGTTAAC  240
 H   V   T   T   L   V   T   R   Y   K   G   K   I   L   H   W   D   V   V   N

GAGATCTTTGCCGAGGACGGCTCGCTCCGCGACAGCGTCTTCAGCCGCGTCCTCGGCGAG  300
 E   I   F   A   E   D   G   S   L   R   D   S   V   F   S   R   V   L   G   E

GACTTTGTCGGCATCGCCTTCCGCGCCGCCCGCGCCGCCGATCCCAACGCCAAGCTCTAC  360
 D   F   V   G   I   A   F   R   A   A   R   A   A   D   P   N   A   K   L   Y

ATCAACGACTACAGGTCGACA                                         420
 I   N   D   Y   R   S   T                                    -

SEQ ID No. 8 (DNA) and SEQ ID Nos. 17-18 (protein):
C1-EG3 (Family 12) gene fragment obtained by PCR based on family 12
cellulases homology analysis.
GAATTCGGGGATTACGAGCTAATGATCTGgtcagttttttttttcttttt
         g   d   y   e   l   m   i   w tcttttcttcncttttcttttcttttcctttctcctgttttattttctta           100 tccattgcttcgccctctttccttaaccctgctgactctctcttcttgtc aatgatactgtaatagGCTGGCGAGATTCGGCGACGTCTACCCCATCGGC           200
                 L   A   R   F   G   D   V   Y   P   I   G TCGTCCCAGGGCCACGTCAACGTGGCCGGCCAGGACTGGGAGCTGTGGAC
 S   S   Q   G   H   V   N   V   A   G   Q   D   W   E   L   W   T GGGCTTCAANGGNAACATGCGGGTCTACAGCTTCGTAGCGCCCANCCCC            299
  G   F   X   G   N   M   R   V   Y   S   F   V   A   P   X   P CGCAACAGNTTCAGCGCCAACGTCAAGGACTTCTTCAACTATCTCCAGTC
  r   n   x   f   s   a   n   v   k   d   f   f   n   y   l   q   s CAACCAGGGCTTCCCGGCCAGCAGCCAATACCTTCTCAAgtaaggagacga          400
  n   q   g   f   p   a   s   s   q   y   l   l   n?

gatctcgaacagcataccatatatgcgtgcggtacaagtgcactaaccccc ttttttttcccgttcgcagtCTTCCAGTTCGGCACTG                        487

SEQ ID No. 9 (DNA) and SEQ ID No. 19 (protein):
Chrysosporium cellobiohydrolase CPH1
    TTTNGGGCGCCGTCTTACTCCTACCTTGCACCGTGATCGGCCAGTCGCGCTGCGAGGGCG
  1    ?  G  A  V  L  L  L  P  C  T  V  I  G  Q  S  R  C  E  G ACTCGTGCGGCGGTACCTACAGCACCGACCGCTATGCCGGCATCTGCGACCCCGACGGAT
 61 D  S  C  G  G  T  Y  S  T  D  R  Y  A  G  I  C  D  P  D  G GCGACTTCAACTCGTACCGCCAGGGCAACAAGACCTTCTACGGCAAGGGCATGACGGTCG
121 C  D  F  N  S  Y  R  Q  G  N  K  T  F  Y  G  K  G  M  T  V ACACGACCAAGAAGATCACGGTCGTCACCCAGTTCCTCAAGAACTCGGCCGGCGAGCTCT
181 D  T  T  K  K  I  T  V  V  T  Q  F  L  K  N  S  A  G  E  L CCGAGATCAAGCGGTTCTACGTCCAGAACGGCAAGGTCATCCCCAACTCCGAGTCCACCA
241 S  E  I  K  R  F  Y  V  Q  N  G  K  V  I  P  N  S  E  S  T TCCCGGGCGTCGAGGGCAACTCCATCACCCAGGACTGGTGCGACCGCCAGAAGGCCGCCT
301 I  P  G  V  E  G  N  S  I  T  Q  D  W  C  D  R  Q  K  A  A TCGGCGACGTGACCGACTTCCAGGACAAGGGCGGCATGGTCCAGATGGGCAAGGCCCTCG
361 F  G  D  V  T  D  F  Q  D  K  G  G  M  V  Q  M  G  K  A  L CGGGGCCCATGGTCCTCGTCATGTCCATATGGGACGACCACGCCAGTNAACA
421 A  G  P  M  V  L  V  M  S  I  W  D  D  H  A  S  ?
```

We claim:

1. A mutant *Chrysosporium* strain comprising a nucleic acid sequence encoding a polypeptide of interest, said nucleic acid sequence being operably linked to a promoter sequence and optionally a secretion signal sequence, said mutant strain expressing said polypeptide of interest at a higher level than the corresponding non-mutant strain under the same conditions, said mutant derived from *Chrysosporium lucknowense* strain C1 (VKM F-3500 D).

2. A mutant *Chrysosporium* strain according to claim 1, said mutant being obtained by recombinant methods comprising stable introduction of at least one heterologous nucleic acid sequence selected from heterologous polypeptide-encoding nucleic acid sequences, heterologous signal sequences and heterologous promoter sequences.

3. A mutant *Chrysosporium* strain according to claim 2, wherein said polypeptide of interest is a heterologous polypeptide of plant, animal, algal, bacterial, archaebacterial or fungal origin.

4. A mutant *Chrysosporium* strain according to claim 1, wherein said polypeptide of interest is a homologous polypeptide which is expressed at a higher level than in the corresponding non-mutant strain under the same conditions.

5. A mutant *Chrysosporium* strain according to claim 1, wherein said polypeptide of interest is selected from carbohydrate-degrading enzymes, proteases, lipases, esterases, other hydrolases, oxidoreductases and transferases.

6. A mutant *Chrysosporium* strain according to claim 1, wherein said polypeptide of interest is selected from fungal enzymes allowing production or over production of primary metabolites, including organic acids, and secondary metabolites, including antibiotics.

7. A mutant *Chrysosporium* strain according to claim 1, wherein said polypeptide of interest is inactivated at a pH below 6.

8. A mutant *Chrysosporium* strain according to claim 1, wherein said polypeptide of interest exhibits optimal activity and/or stability at a pH above 6, and/or has more than 70% of its activity and/or stability at a pH above 6.

9. A mutant *Chrysosporium* strain according to claim 1, comprising a heterologous signal sequence.

10. A mutant *Chrysosporium* strain according to claim 1, wherein said secretion signal is a fungal signal sequence.

11. A mutant *Chrysosporium* strain according to claim 10, wherein the fungal signal sequence is a signal sequence of a cellulase, β-galactosidase, xylanase, pectinase, esterase, protease, amylase, polygalacturonase or hydrophobin.

12. A mutant *Chrysosporium* strain according to claim 1, further comprising a selectable marker.

13. A mutant *Chrysosporium* strain according to claim 12, wherein the selectable marker confers resistance to a drug or relieves a nutritional defect.

14. A mutant *Chrysosporium* strain according to claim 1, comprising a heterologous promoter.

15. A mutant *Chrysosporium* strain according to claim 1, comprising a fungal promoter.

16. A mutant *Chrysosporium* strain according to claim 15, wherein the promoter is an inducible promoter.

17. A mutant *Chrysosporium* strain according to claim 15, wherein the promoter is a high expression promoter.

18. A mutant *Chrysosporium* strain according to claim 1, said mutant being obtained by mutagenesis steps, the steps including at least one step chosen from the group consisting of UV irradiation and chemical mutagenesis.

19. A mutant *Chrysosporium* strain according to claim 18, wherein the mutagenesis steps comprise a first UV irradiation step, a N-methyl-N'-nitro-Nnitrosoguanidine treatment step, and a second UV irradiation step.

20. A mutant *Chrysosporium* strain according to claim 1, wherein, when a *Trichoderma reesei* strain and said *Chrysosporium* strain are cultured under equivalent optimal conditions until the *Trichoderma* culture attains a viscosity of 200-600 cP, said *Chrysosporium* strain exhibits a biomass of less than half that of the *Trichoderma*.

21. A mutant *Chrysosporium* strain according to claim 1, said strain producing at least the amount of cellulase in moles per liter as produced by any of the *Chrysosporium lucknowense* strains C1 (VKM F-3500 D), UV13-6 (VKM F-\3632 D), NG7C-19 (VKM F-3633 D), and UV18-25 (VKM F-3631 D).

22. A mutant *Chrysosporium* strain according to claim 1, said strain producing less protease activity than produced by the parent *Chrysosporium* strain from which it was derived.

23. A mutant *Chrysosporium* strain according to claim 22, wherein the strain produces less than half the amount of protease produced by the parent strain.

24. A mutant *Chrysosporium* strain derived from *Chrysosporium lucknowense* strain C1 (VKM F-3500 D), wherein said mutant strain expresses a polypeptide of interest at a higher level than the corresponding non-mutant strain under the same conditions.

25. A mutant *Chrysosporium* strain wherein said mutant is or is derived from a *Chrysosporium lucknowense* mutant strain selected from the group consisting of UV 13-6 (VKM F-3632 D), NG7C-19 (VKM F-3633 D), and UV18-25 (VKM F-3631 D).

26. The mutant *Chrysosporium* strain of claim 25 wherein said mutant strain expresses a polypeptide of interest at a higher level than the corresponding original non-mutant strain under the same conditions.

27. A mutant *Chrysosporium* strain according to claim 24 or 25 wherein, when a *Trichoderma reesei* strain and said *Chrysosporium* strain are cultured under equivalent optimal conditions until the *Trichoderma* culture attains a viscosity of 200-600 cP, said *Chrysosporium* strain exhibits a biomass of less than half that of the *Trichoderma.*

28. A mutant *Chrysosporium* strain according to claim 24 or 25, said strain producing at least the amount of cellulase in moles per liter as produced by any of the *Chrysosporium lucknowense* strains C1 (VKM F-3500 D), UV13-6 (VKM F-3632 D), NG7C-19 (VKM F-3633 D), and UV18-25 (VKM F-3631 D).

29. A mutant *Chrysosporium* strain according to claim 24 or 25, said strain producing less protease than produced by the parent *Chrysosporium* strain from which it was derived.

30. A mutant *Chrysosporium* strain according to claim 29, wherein the strain produces less than half the amount of protease produced by the parent strain.

31. A mutant *Chrysosporium* strain according to claim 25, comprising a nucleic acid sequence encoding a polypeptide of interest, said nucleic acid sequence being operably linked to a promoter sequence and optionally a secretion signal sequence, said mutant strain expressing said polypeptide of interest at a higher level than the corresponding non-mutant strain under the same conditions.

32. A mutant *Chrysosporium* strain according to claim 31, said mutant being obtained by recombinant methods comprising introduction of at least one heterologous nucleic acid sequence selected from heterologous polypeptide encoding nucleic acid sequences, heterologous signal sequences and heterologous promoter sequences.

33. A mutant *Chrysosporium* strain according to claim 32, wherein said polypeptide of interest is a heterologous polypeptide of plant, animal, algal, bacterial, archaebacterial or fungal origin.

34. A mutant *Chrysosporium* strain according to claim 31, wherein said polypeptide of interest is a homologous polypeptide which is expressed at a higher level than in the corresponding non-mutant strain under the same conditions.

35. A mutant *Chrysosporium* strain according to claim 31, comprising a heterologous signal sequence.

36. A mutant *Chrysosporium* strain according to claim 31, wherein said secretion signal is a fungal signal sequence.

37. A mutant *Chrysosporium* strain according to claim 31, comprising a fungal promoter.

38. A mutant *Chrysosporium* strain according to claim 37, wherein the promoter is an inducible promoter.

39. A mutant *Chrysosporium* strain according to claim 37, wherein the promoter is a high expression promoter.

40. A mutant *Chrysosporium* strain according to claim 31, wherein the promoter is cbh 1.

41. A mutant *Chrysosporium* strain according to claim 31, said strain producing at least the amount of cellulase in moles per liter as produced by any of the *Chrysosporium lucknowense* strains C1 (VKM F-3500 D), UV13.6 (VKM F-3632 D), NG7C-19 (VKM F-3633 D), and UV18-25 (VKM F-3631 D).

42. A mutant *Chrysosporium* strain according to claim 31, said strain producing less protease activity than produced by the parent *Chrysosporium* strain from which it was derived.

43. A mutant *Chrysosporium* strain according to claim 42, wherein the strain produces less than half the amount of protease produced by the parent strain.

44. A mutant *Chrysosporium* strain according to claim 24 or 25, wherein said mutant strain has narrower mycelia than the corresponding non-mutant strain or exhibits mycelial fragmentation.

45. A mutant *Chrysosporium* strain according to claim 24 or 25 wherein said mutant strain has a disrupted endogenous gene.

46. A mutant *Chrysosporium* strain according to claim 45, wherein said mutant strain has a disrupted protease gene and exhibits reduced protease activity or an absence of protease activity.

47. A mutant *Chrysosporium* strain according to claim 45, wherein said mutant strain has a disrupted cellulase gene and does not produce a cellulase.

48. A mutant *Chrysosporium* strain according to claim 32, wherein said polypeptide of interest is a heterologous polypeptide of human origin.

49. A mutant *Chrysosporium* strain according to claim 48, wherein said polypeptide of interest is biologically active.

50. A mutant *Chrysosporium* strain according to claim 48, wherein said polypeptide, or a modified or mutated form of said polypeptide, is used for pharmaceutical purposes.

51. A method of producing a polypeptide of interest, comprising culturing a strain according to claim 1 under conditions permitting expression of the polypeptide of interest, and recovering the subsequently produced polypeptide of interest.

52. The method of claim 51, wherein the conditions further permit secretion of the polypeptide of interest.

53. A method of producing a polypeptide of interest, comprising culturing a strain according to claim 24 under conditions permitting expression of the polypeptide of interest, and recovering the subsequently produced polypeptide of interest.

54. The method of claim 53, wherein the conditions further permit secretion of the polypeptide of interest.

55. A method of producing a polypeptide of interest, comprising culturing a strain according to claim 25 under conditions permitting expression of the polypeptide of interest, and recovering the subsequently produced polypeptide of interest.

56. The method of claim 25, wherein the conditions further permit secretion of the polypeptide of interest.

57. The method according to anyone of claims 51-56, wherein the polypeptide is expressed as a precursor protein, further comprising the step of cleavage of the precursor into the polypeptide or precursor of interest.

58. The method according to claim 57, wherein the cleavage step is cleavage with an enzyme selected from the group consisting of Kex-2 like proteases, basic amino acid paired proteases, or Kex-2.

59. The method according to anyone of claims 51, 53, and 55, wherein the cultivation occurs at a pH ranging from about 4 to about 10 and/or at a temperature between about 25° C. and about 43° C.

60. A method of culturing the mutant *Chrysosporium* strain of anyone of claims 1, 24, and 26 under conditions permitting expression of a polypeptide of interest.

61. The method of claim 60, wherein said strain produces neutral or alkaline cellulases.

62. A mutant *Chrysosporium* strain according to claim 14, wherein the promoter is selected from the group consisting of cbh1, xyl1, eg3, eg5, eg6, chitinase, and gpd1.

63. A mutant *Chrysosporium* strain according to claim 14, wherein the promoter is cbh1.

64. A mutant *Chrysosporium* strain according to claim 31, wherein the promoter is selected from the group consisting of cbh1, xyl1, eg3, eg5, eg6, chitinase, and gpd1.

* * * * *

SEQUENCE LISTING

<160> NUMBER OF SEQ ID NOS: 19

<210> SEQ ID NO 1
<211> LENGTH: 4451
<212> TYPE: DNA
<213> ORGANISM: Chrysosporium lucknowense
<220> FEATURE:
<221> NAME/KEY: modified_base
<222> LOCATION: (2941)
<223> OTHER INFORMATION: a, t, c, g, other or unknown

<400> SEQUENCE: 1

```
aaggtatccg atttggggaa cgtcgatgaa agtattgcaa aagtgacgag agttgcgcaa       60
ctaactcgct gccgaagaag ctgcggaaga aagagaacac cgaaagtgga ataacgttac      120
ggatgtcctg acctcaaagt tgaaaccagc ccttcctgct ctatttggga aagcggcttg      180
cccttgaatg cgctgcactg tggcacgact accagtgatc gggaggagca aactaccctg      240
gtccgttcct tggtggggcg gcactaggcc caacttaggg tgatcggagg tcgatgccgc      300
ggtcctcgtt ggtctgggct cttctcattt cccggtttgc accccccgtt gcacctgctg      360
atcgcccgcc aacgccgatg aggttgcgcc cagaccgaca atcaccgcgg ctgcattccc      420
aagtatattg aagatggcac caggtacccg gttttgcgtc ccagtcgttt ggtgccaaat      480
ttgggagttt ttgagcctca agatctgggg aaatcgacct caacttccat acaagttaaa      540
gtcgcacaca cggcgagttc cacgaagaga cacattttttt tctgaaggcc tctctccccg      600
cacatcagaa accaccaaat accaagactg cagaagccgg ggtaagtggg ccaccgggac      660
tacactaaaa tgcggggaga agcgagatcc gttgcgaagg gaagggatgg ggtgtgctgc      720
ggctttctcc gctctcgtgc gccttttgct tgaatctagt gtacaccagg gtaggctccg      780
aaggagtatc tacggcagcg ctgttcgtgc tgcgttgaga gtcagggcgg agacgagcag      840
gcgacaggag cctcgcaccg gcacttcgga tcgcatttgc gcggagcgtc aaatacgctc      900
ttctgcggtc atcagagagc atcgtgaacc aaggttcttc cgcagggcgg cctgggcttc      960
gcagagtcgc actcggcgga cgccttccgt gtcaccccct gataacctgg ctgccgcgccc     1020
agactcctcc aatgaggtgt gtggttgccc tcgccgaccc ttcagcaacc ttaatcgctt     1080
ccatcgcacg gctccacgtc ctcgaacgat gccctcagtc cgtgcccggc cgtggcaacc     1140
ataacgtgac atcgccgccc agcctactag ccgctatcga ccggttaggc ttgtcaccgc     1200
agcgcccatt ctccatcggg cctctactct gatccacctc acccaccgca agcactagcg     1260
agcctcacca gagtgcaagc gacacgaccc gcttggccct tcgtccttga ctatctccca     1320
gacctcttgc catcttgccg acgccgcccc ctttttttttc tcctcccccct gccggcaggt     1380
cggtggcccc agtcccgaga tggcattgct ccgttgtcca tgacgaccca tcattcgatg     1440
gctgactggc acactcgtct tgtttgagca tcgacggccc gcggcccgtc tcccacggta     1500
cggaacctcg ttgtacagta cctctcgtaa tgatacccaa caccggggcc gagcgctggg     1560
agggcggcgt tcccgagaag ccgggaaggc ggctggccgg ctgacctttg tgacttggcg     1620
atggatgcgg ccatggagaa tgtccgtccg aagcgacgcg acaattagcc tggctaccat     1680
cgatataaat tgggtgattc ccagctcttg atgggcgtgt cttctgcctg gcagccctcg     1740
tcttcagatc aagcaactgt gtgctgatcc tcttccgcca tgtacgccaa gttcgcgacc     1800
ctcgccgccc ttgtgctgg cgccgctgct cagaacgcct gcactctgac cgctgagaac     1860
caccccctcgc tgacgtggtc caagtgcacg tctggcggca gctgcaccag cgtccagggt     1920
```

```
tccatcacca tcgacgccaa ctggcggtgg actcaccgga ccgatagcgc caccaactgc    1980
tacgagggca acaagtggga tacttcgtac tgcagcgatg gtccttcttg cgcctccaag    2040
tgctgcatcg acggcgctga ctactcgagc acctatggca tcaccacgag cggtaactcc    2100
ctgaacctca agttcgtcac caagggccag tactcgacca acatcggctc gcgtacctac    2160
ctgatggaga gcgacaccaa gtaccagagt aagttcctct cgcacccggc cgccgggaga    2220
tgatggcgcc cagcccgctg acgcgaatga cacagtgttc cagctcctcg gcaacgagtt    2280
caccttcgat gtcgacgtct ccaacctcgg ctgcggcctc aatggcgccc tctacttcgt    2340
gtccatggat gccgatggtg gcatgtccaa gtactcgggc aacaaggcag gtgccaagta    2400
cggtaccggc tactgtgatt ctcagtgccc ccgcgacctc aagttcatca acggcgaggc    2460
caacgtagag aactggcaga gctcgaccaa cgatgccaac gccggcacgg gcaagtacgg    2520
cagctgctgc tccgagatgg acgtctggga ggccaacaac atggccgccg ccttcactcc    2580
ccacccttgc accgtgatcg gccagtgcgc ctgcgagggc gactcgtgcg gcggtaccta    2640
cagcaccgac cgctatgccg gcatctgcga ccccgacgga tgcgacttca actcgtaccg    2700
ccagggcaac aagaccttct acggcaaggg catgacggtc gacacgacca agaagatcac    2760
ggtcgtcacc cagttcctca agaactcggc cggcgagctc tccgagatca gcggttcta    2820 cgtccagaac ggcaaggtca tccccaactc cgagtccacc atcccgggcg tcagggcaa    2880 ctccatcacc caggactggt gcgaccgcca gaaggccgcc ttcggcgacg tgaccgactt    2940
ncaggacaag ggcggcatgg tccagatggg caaggccctc gcggggccca tggtcctcgt    3000
catgtccatc tgggacgacc acgccgtcaa catgctctgg ctcgactcca cctggcccat    3060
cgacggcgcc ggcaagccgg gcgccgagcg cggtgcctgc cccaccacct cgggcgtccc    3120
cgctgaggtc gaggccgagg cccccaactc caacgtcatc ttctccaaca tccgcttcgg    3180
ccccatcggc tccaccgtct ccggcctgcc cgacggcggc agcggcaacc ccaacccgcc    3240
cgtcagctcg tccaccccgg tcccctcctc gtccaccaca tcctccggtt cctccggccc    3300
gactggcggc acgggtgtcg ctaagcacta tgagcaatgc ggaggaatcg ggttcactgg    3360
ccctacccag tgcgagagcc cctacacttg caccaagctg aatgactggt actcgcagtg    3420
cctgtaaacg aacctctctg aaggaggttc tgagacacgc gcgattcttc tgtatatagt    3480 tttattttc actctggagt gcttcgctcc accagtacat aaacctttt tttcacgtaa    3540 caaaatggct tcttttcaga ccatgtgaac catcttgatg ccttgacctc ttcagttctc    3600
actttaacgt agttcgcgtt agtctgtatg tcccagttgc atgtagttga ataaatacc    3660 cctggaagtg ggtctgggcc tttgtgggac ggagccctct ttctgtggtc tggagagccc    3720
gctctctacc gcctaccttc ttaccacagt acactactca cacattgctg aactgaccca    3780
tcataccgta ctttatcctg ttaattcgtg gtgctgtcga ctattctatt tgctcaaatg    3840
gagagcacat tcatcggcgc agggatacac ggtttatgga ccccaagagt gtaaggacta    3900
ttattagtaa tattatatgc ctctaggcgc cttaacttca acaggcgagc actactaatc    3960
aacttttggt agacccaatt acaaacgacc atacgtgccg gaaattttgg gattccgtcc    4020
gctctcccca accaagctag aagaggcaac gaacagccaa tcccggtgct aattaaatta    4080
tatggttcat ttttttaaa aaatttttt cttcccattt tcctctcgct tttcttttc    4140 gcatcgtagt tgatcaaagt ccaagtcaag cgagctattt gtgctatagc tcggtggcta    4200
taatcagtac agcttagaga ggctgtaaag gtatgatacc acagcagtat tcgcgctata    4260
agcggcactc ctagactaat tgttacggtc tacagaagta ggtaataaaa gcgttaattg    4320
```

```
ttctaaatac tagaggcact tagagaagct atctaaatat atattgaccc tagcttatta   4380
tccctattag taagttagtt agctctaacc tatagatagc caaatgctat aataggtacc   4440
agggttcaaa a                                                        4451

<210> SEQ ID NO 2
<211> LENGTH: 3028
<212> TYPE: DNA
<213> ORGANISM: Chrysosporium lucknowense
<220> FEATURE:
<221> NAME/KEY: modified_base
<222> LOCATION: (46)..(47)
<223> OTHER INFORMATION: a, t, c, g, other or unknown
<220> FEATURE:
<221> NAME/KEY: modified_base
<222> LOCATION: (374)
<223> OTHER INFORMATION: a, t, c, g, other or unknown

<400> SEQUENCE: 2
tcatcaactt ggcgtttgga tgtactaata ttacacgtcg tttgcnnagc ggagtctgtg     60
tcatctccgt ggggtcgggt gctccagacg acgcttcggg ccgatcctga attcgggaag    120
gaaacggttc ggctaatcag gtcctctaaa atataacgaa gcactacaga gggagttcct    180
cagaggacat cgtatcaacc gaagaacgaa gcgccgaaag gactgatcaa aacaggagta    240
ggtagggatg tgtgagtacc taaactttcc atacctgaca taaaatcatc atggtgcttc    300
agacctgttt gatgaggcga gggcggaggc cgcattgtat tttcgttcct tccttctttt    360
tgttagtata tctnagggtt ccatcgtaaa atggaatctt ccagctctac tagtaattag    420
aacaatagtt ctgatgtcgt gcgccaagct tttcagatg actgccaaaa acccatcatg     480
ggtatggaca aaagcagtaa tcggagtcac aacgccgcat ttccttcat gatttccgtc     540 aaccggagag gtcggaggag gactccggcc acatgtgatg cgaagaagta catggcgcca    600
tggttctaac ctcttatagt ctgaaaatgc gcggaggcca gcgaagccaa gcccgggaac    660
cgttcttgtc atggtttcag tattgtttcg ctaaacattc tatccgattc gcgataggtg    720
cggctgccac cgaaggttgt atccttaaag ctttggtaag tacggagtac ggaaatggaa    780
acgcgccgca gtcctggttc catcggtatc ctccgcatgc tccgccaaaa aaagaaaacc    840
cgggtatgtt tacaaaggat ataagagaca agatgcacca cccgcccccct tcccatctgc   900 cggttgccca cgtcgccgtc gactgcttgt ccgcttccta cctgcagcct ctttcagaga    960
ccatcaaaca tgcgtactct tacgttcgtg ctggcagccg ccccggtggc tgtgcttgcc   1020
caatctcctc tgtggggcca gtgtatgtaa ttgccttact cggaaaatag tcaccactag   1080
agggacttaa gctcactact tcctgtttca caataggcgg cggtcaaggc tggacaggtc   1140
ccacgacctg cgtttctggc gcagtatgcc aattcgtcaa gtcagtaact gcttttattt   1200
cttttctctc tgggattacg atttcgtttt gcacttagct tggttctgca tttcattgtt   1260
gtattgttct ctttttgtgt gtgagaggtt ttattaccac ctaaaggcca tttgctaaca   1320
aatctcccca gtgactggta ctcccaatgc gtgcccggat cgagcaaccc tcctacgggc   1380
accaccagca gcaccactgg aagcaccccg gctcctactg gcggcggcgg cagcggaacc   1440
ggcctccacg acaaattcaa ggccaagggc aagctctact tcggaaccga gatcgatcac   1500
taccatctca acaacaatgc cttgaccaac attgtcaaga aagactttgg tcaagtcact   1560
cacgagaaca gcttgaagtg ggatgctact gagcgtgagt gacctctcct ccttctcccg   1620
acaataatag ataattacga gccggttcga ggctgacatt gcgcgattct agcgagccgc   1680
aatcaattca actttgccaa cgccgacgcg gttgtcaact ttgcccaggc caacggcaag   1740
```

```
ctcatccgcg gccacaccct cctctggcac tctcagctgc cgcagtgggt gcagaacatc   1800
aacgaccgca acaccttgac ccaggtcatc gagaaccacg tcaccaccct tgtcactcgc   1860
tacaagggca agatcctcca ctgggacgtc gttaacgaga tctttgccga ggacggctcg   1920
ctccgcgaca gcgtcttcag ccgcgtcctc ggcgaggact ttgtcggcat cgccttccgc   1980
gccgcccgcg ccgccgatcc caacgccaag ctctacatca acgactacaa cctcgacatt   2040
gccaactacg ccaaggtgac ccggggcatg gtcgagaagg tcaacaagtg gatcgcccag   2100
ggcatcccga tcgacggcat cggcacccag tgccacctgg ccgggcccgg cgggtggaac   2160
acggccgccg cgtccccga cgccctcaag gccctcgccg cggccaacgt caaggagatc   2220
gccatcaccg agctcgacat cgccggcgcc tccgccaacg actacctcac cgtcatgaac   2280
gcctgcctcc aggtctccaa gtgcgtcggc atcaccgtct ggggcgtctc tgacaaggac   2340
agctggaggt cgagcagcaa cccgctcctc ttcgacagca actaccagcc aaaggcggca   2400
tacaatgctc tgattaatgc cttgtaagag gaggtatatt attttagag gcaatgaagc   2460 taggaggaaa gaggggaagt gaggtaatta gctaggacag gcaaatctag cagcaattat   2520
aagtcaacac tatataaaat attcctataa tggcttgtgc ttcggtgtgc aaaaaaaaaa   2580 aaaaaaaaa aaaaaaaaaa aaaaaaaac tcaaaacaa aaatgatcca acatgattcg   2640
aaatggcgac cttgcaaatg cacacctcag ataataccac tatacaatac accttaaatg   2700
gcacctaaat ccatttgtct gcggtcatag acggggctta agaagcctgg gatgcaggtg   2760
tcgatgcaag ggttacgtca gtgtatgata tgagtatgaa ccatgctgtc tgggtaattc   2820
tccactttcc ctccccttac gactcttcgg gtgtgcctct ctagaaagtc gactcctggc   2880
gcctcagatc gccctttggc tctgttcggt acaatgacgt ccgctggttt cttccaaaga   2940
ccaggtattt ctcccgtggc aacaaagaat accaaatacc tatatcgaac cgtagtcttc   3000
tgataattag atgtctctca aggcgcgg                                    3028

<210> SEQ ID NO 3
<211> LENGTH: 3036
<212> TYPE: DNA
<213> ORGANISM: Chrysosporium lucknowense

<400> SEQUENCE: 3
ccgccctgga gcgtggaccg tggggacagg cggcaaatga gaccctattg gggcgcatcg     60
acggtgcaga accgaggttc cgggaccttg gcagagcggc ccagggaccc cgccatccag    120
ctatgcgcct ccacagaagc cgaccgatgc tcgggttgca tcccgagatc gtcggtatta    180
aggagagggg agaagaagaa gggggggggg gggggggaat gagacaacaa cactcaggcg    240
cgccaattag aacttcaacg agcctccttc ctgcatccag acaagaccga ggtcgagccg    300
ggtactatgc aagcgtcccg tgccgcgtga tgtcgctcgt aggtgttgac aggttctcag    360
ctgtttcttg aatccccggg aggtggacta aaggggcaag agaccatggt aagctccgtc    420
gccagccctc ccgttgcgga gcggaagccg aggaccgacc ttcttctgga gaacccgggc    480 tgccccgggcg gaggcgggtt ccgccttttt tttaaccagt ccgagttgtt gtcgcgaact    540
gcgctcggtt gcaacgtcag tgtccaatcg gcaggcgtat cgcgacccgg taagggggtt    600
acggcatgtg ttctcggctt ccgcacatca aaacttactc gtattcgtcc tgaccttggt    660
aattaattat gtcgcaagac aaggagttgt ttgagacgac tccggcgcgc ataattacac    720
agtggtgcag tattatatat cttctctccg tagggacgac gacaaagacc cgtcagtgat    780
taataataat tagtagcagt ttcttcttt caagactcaa gaatactcct ttccgccatc      840
```

```
gtggcagcgt ttagattcat catgcagccg tttctgctct tgttcctctc gtcggtcacg    900
gcggcgagcc ccctgacggc gctcgacaag cggcagcagg cgacgttgtg cgagcagtac    960
ggctactggt cgggcaacgg ttacgaggtc aacaacaaca actggggcaa ggattcggcc   1020
tcgggcggcc atcagtgcac ctacgtcgac agcagcagct ccagcggcgt cgcctggcac   1080
acgacctggc agtgggaagg aggccagaac caggtcaaga gcttcgccaa ctgcggcctg   1140
caggtgccca agggcaggac catctcgtcc atcagcaacc tgcagacctc catctcgtgg   1200
tcctacagca acaccaacat ccgcgccaac gtggcctacg acctcttcac cgcggcagac   1260
ccgaaccacg cgaccagcag cggcgactac gagctcatga tctggtcagt tttttttttc   1320
tttttctttt tcttctcttt tcttttcttt tcctttctcc tgttttattt tcttatccat   1380
tgcttcgccc tctttcctta accctgctga ctctctcttc ttgtcaatga tactgtaata   1440
ggctggcgag attcggcgac gtctaccccca tcggctcgtc ccagggccac gtcaacgtgg   1500
ccggccagga ctgggagctg tggacgggct caacggcaa catgcgggtc tacagcttcg   1560
tagcgcccag cccccgcaac agcttcagcg ccaacgtcaa ggacttcttc aactatctcc   1620
agtccaacca gggcttcccg gccagcagcc aatacctttct cagtaaggag acgagatctc   1680
gaacagcata ccatatatgc gtgcggtaca agtgcactaa ccccctttttt tttcccgttc   1740
gcagtcttcc aggcgggcac cgagcccttc accggcggcg agaccaccct taccgtcaac   1800
aactactctg caagggttgc ttaaacagga aggccgagga tggcccccaa ggccgttgcg   1860
ggttcacgag ctctcttctt ttcaagtgct gtacatacat aattagcgta ccaagtcata   1920
gctgtttgtc agcttcaaac taagtgctcg cccacaaaag agggggagg ggaaaataac   1980
aaattgccga acgcagtgat aagcttctgg gagcgttgaa agcagtctac agtaggtggc   2040
tgyacgaagg aaaagagtgc cttattaaag ctatctacaa aggagacaaa acgactgata   2100
tttatggaca aagggactgg ccaatgcgtt aaacagcctc atacagctgt agcatatata   2160
tggctaatac gtttggaagc tctatagctt ccgacacacc ccctagttaa acgtagtagt   2220
cgtttaacta cgcttttgygg tgatactgtt cttggtatta tatcctttgt cgctcttacc   2280
tcgatagctc cttcagggg cctgccttct gtattcggaa gtctaaaaga gtcgagtata   2340
gtagagcgat tcctttaaag ctatagatca aatatggcca ttataactat agtagtaata   2400
gtattactag ttttaatcat aatagtaata ataggatgac gcctcttatg cttgaatcaa   2460
tagatgactc gttaggtcta cctattacaa acactataac tgctagtagg tcgactcctg   2520
ctcctataac acctcgtaag tataagtata ctaaagcttc tataccgtaa gtgttcctat   2580
tgtccctatt tgattaactt tattactagt tttgtagttt tcttagtagt tctagcgatt   2640
taagcgagtt tacgtggttc ggcttcttct ggttaatttg atagcgactc tatcacagtt   2700
tctagcgctt tactagtcac gtctagatcg tttaagctga ctaaatatag caacatcgaa   2760
gctagcgagc tttgtaaggt accctataga atatatatac ggtcggctct agtaggacgt   2820
tcttttagca aatgtcacga tcattccggc gttagctcct actattacta ttatacctat   2880
agttcctata agtgtaggga gatatacgtt aatcgcctat acgtctaata gctcttataa   2940
tacttatact aactataatg gtagtcttgc ttcttatatt aggtcggcta aggacttaac   3000
gaaggctcta atggatagag ctaaggcttc tataag                             3036
```

<210> SEQ ID NO 4
<211> LENGTH: 2547
<212> TYPE: DNA
<213> ORGANISM: Chrysosporium lucknowense

<400> SEQUENCE: 4

```
tgagcagcaa tgagcagcaa tgagcattcc tgggccaccg agtctgagtg ccagtacgga      60
gtatcgtact tcgtaccggg gttttgatttg gtgacggtgc ttttcacctc tcgatgcccg     120
aaatcgggtc taagctgagt ttgatcaaat atgtgactcc aacatcgccc ccttcggcaa     180
accccgtcga cacgtgtgtc atccttccat tgcaagcgat cactcgcagg gcgtgacgat     240
gaacgagatt tttgcccgga ccgattcgcg gatatagcgg cagccgacca gcctaccac     300
actgatggcc gtgtcactag tgtatgctcc cagaaccgca agcatacact gggcaatgct     360
tggtatgcag ttgaggcagc tttatgtttc catacccttc cacttcggct cggggactcg     420
gcggggtcgc ggaagtttga cggcagccgt cgggccttag gccgagatta ccgtggttgt     480
ggcccagttt tagccgttcc cgtccgtttc ctaccggacc atgattttcg tgaaccattg     540
caatcccgaa gcgcatttcc gacgttaagg agttacctcc gctgcccaga attcatgatc     600
gtggccggct caaggcagcg tggcgggggca tccgtgtcaa gctcccagga ggaggtgcgc    660
gatttcaaat ccgggccaaa acaggccaag actggctggc caaaaaaagg agcgtagacg     720
gcccgggaca tcggacgtca gctcgcagcc acccaaaacc ggtccgatct actcgcttac     780
tgtggtagtt caggtacttt tgagtagtaa aaacgctacg gcagggccgg ggggttcccc     840
ggtgacggag gtgcctctgc ggtggcgaac atcccacgca ctctcgagct acggtgacac     900
ctcgtgtcct gttggtcttg caatgctggg gcggcaggaa atgcgtcgcg ctcctcccgg     960
ccaagaccta aaacagacag cgccgcaaag tcgctcacta gcaccgcgaa acgaagatgc    1020
cccacctcaa cgcaatctgt gatgcaagca attgggaagg ctcaccccac ctcagcgagg    1080
ggctcaacca tttttattat cagctcatgc caccacaaca tgactgtttt ctttccttgc    1140
tcatcccaca tttgacaaaa atcgtcgatt aatctctttc catacaggcc gtccgcgctc    1200
tgataaccac ataaaagtct cttcagtcaa cagctcaaag ctccctcatc cctccaggta    1260
agcagccaaa gagctccccc acggaccccg cactgcctca tcccgcctgt atcggacctg    1320
cgcgacccag cagagaatcc caaacctttg ctgcttgctg cccggttccg gactgagctg    1380
caacccaagc cttttaaaaag cttttccctt ctcccacggt gtcaactctg tcctatccct    1440
ccgacatccg ttgagctcaa caactccccg aacctttac cccgcgccga gctacccctc     1500
catcaaacca ccctgacagc tcgctcactc acctccccac atcacagaaa tcaaaatgac    1560
tatcaaggtc ggcatcaacg gtttcggccg tatcggccgt atcgtcttcc gcaactccat    1620
cgagcactcg gatgtcgaga tcgttgccgt caacgacccc ttcattgagc ccaagtacgc    1680
tgtaagtagt ttttttttc cttcctcgcg ttctttcctg ttccatcgac agtacgagat    1740
gatcttgcag gcggatcgga gctaaccgcg attgtcgtac aggagtacat gctcaagtat    1800
gactcgaccc acggtatctt caacggcacc atcgccgtcg agggcaacga cctcattgtc    1860
aacggcaaga gggtcaagtt ctacactgag cgggmccccg ccaacattcc ctggarggaa    1920
actggtgccg agtacatmrt cgagtcgacc ggtgtgttca ccamcaccsa gaaggctagc    1980
gcccacctca gggcggcgc caagcgcgtc atcatctctg ctccctcggc cgatgccccc    2040
atgtacgtca tgggcgtcaa cgagaagacc tacgacggca aggcccaggt catctctaac    2100
gcctcgtgca ccaccaactg cctggctccc ctcgccaagg tcatccacga caagttcggc    2160
ctcgttgagg gtctcatgac caccgtccac tcctacactg ccacccagaa gaccgtcgat    2220
ggtccctctg ccaaggactg gcgtggtggc cgtggtgctg ctcagaacat catccccagc    2280
agcactggcg ccgccaaggc cgtcggcaag gtcatccctg agctcaacgg caagctcacc    2340
```

-continued

| | |
|---|---|
| ggcatgtccc tccgtgtccc cacccccaac gtttccgttg tcgacctcac ctgccgcctc | 2400 |
| gagaaggagg ctacctacga cgacatcaag gccgccatca aggaggccgc cgccggcccc | 2460 |
| ctcaagggtg agttatctgg ttccttttt tttttttgga gaacgacaca tgctgataaa | 2520 |
| acccaggcat cctcgactac actgagg | 2547 |

<210> SEQ ID NO 5
<211> LENGTH: 5046
<212> TYPE: DNA
<213> ORGANISM: Chrysosporium sp.

<400> SEQUENCE: 5

| | |
|---|---|
| gcttaggaga atcacgagaa gctaattggg ctctatagta tccgacaaga tgacccagag | 60 |
| cgagattgag gatctcgagg gaaccctgaa gcagagcagc aacaacgaca ccagcctcct | 120 |
| ccgcgacctg ctcgacaaga ttcccgatgg cctcctcggc ggcaacaaca aatccaagct | 180 |
| ggacgatatc cagagcaacg cgcaggccgc gcagatggaa aacctgagcg tctcgccgcg | 240 |
| ggaacccgag gagctgacca gatacgtcca ggaagtgttc cgtcagatca tgcccgccat | 300 |
| caagttccat gaccagcttc tccaggacat ctcggaggcc atcgacaaga tcccggtgct | 360 |
| gcccaagatt gtggagcagc tggaggagca gatgtccatc tttgtattcc agatcatggc | 420 |
| cccgttcgtg gttccgctta tcgagcagat caagaacgag ctcgcgactg gctcagcga | 480 |
| gatcatccag agcagcaggg ctgagcagca aacgtctttt gaggacgaca acgccaccga | 540 |
| cccgactcac tcgatgttgg ccaaggacca ctttagtaac gtaaagccga ccctaatcag | 600 |
| aagctcgcat gtagaattga gttagactga cgcgacttgt ttcccgtctc tgtagatcct | 660 |
| caacgagatc ggcggtcgcg ccgcctccaa ggtcgtctcc tgggtcgtcc cgcagctcat | 720 |
| ggaggcctgg gacgatgaca cgtcgacgt ggaccgcctg cttgacaaga tcatttacgg | 780 |
| agtgttccac catcccgcgc agcgcaccat gggccctgag ggggcgtccg agggccggga | 840 |
| gctcatcttc aacatggtgc gcgagtggtg ggaggacatg agcgacgggc agcgcgacga | 900 |
| gtaccggggc aagctgagcc gcgagggagt cgagagaggc gacaaccacc gcgagggcca | 960 |
| gcacgactgc ggccacggct gcgggggcaa gctcaagatg cacaagaact tccggaacga | 1020 |
| ggcgccccag acggtagagg accagatcgc gggcgccgcc gcggaggcca tcatgggagg | 1080 |
| cgtcaagcag ggcctgtcgc aggccgtgca gaacgccgcc ggccgccagg agtcgtcgga | 1140 |
| gagcagcggc ctgggtgggt tcatcagcag cgtcgcgggc ggcctcctgg gcggcgccct | 1200 |
| caagagggac gagacagagt cgtaccaggc cggcggccgc accgaggacg gcgggtacac | 1260 |
| gcagaccacg accgagtacg gctactccgg aggccgctac ggccaggccc agtacacgga | 1320 |
| gacgcagtac ggcggcggcg gcggcggccg cagcgagtac cgccgctacg agcagcgcga | 1380 |
| ggatgatgac ggccgggtcc agagctacgg atacacggaa cagcgcaccg agacgcgcta | 1440 |
| cgacagctac tcgggtggct atggcggccg cgaggagacc agcagctatg cggcggcgg | 1500 |
| cagcgcgagc gaatacattc gtagctccca gcagagtagc tacggtggca gcggctatgg | 1560 |
| cagtgggtac ggtcgtcgtg atgaagaaga gagcagcggc tatggaagtg gttacggtcg | 1620 |
| tcgtgatgaa gaggagagtg gtggttatgg tggcggctat ggccgccgtc aggaagaaga | 1680 |
| gagtagcagc tatggaagcg gttatggtcg tcgtcgtgat gaagaagaga gcggcggtta | 1740 |
| tggtggtggc tacggccgcc gtcaggaaga agagagtagc ggctatggaa gtggttacgg | 1800 |
| tcgtcgtgat gaagaaggga gcggcggtta tggtggtggc tacggccgcc gtcatgagga | 1860 |
| agagagcagt ggttacggca gcggctatgg tcgtcgccat gaagaggagg gcggtggcta | 1920 |

```
cggcagtggt tacggccgcc ggcgcaacga cgaggaggaa gaggaggatg gcggacgccg   1980
gaggtggggt tactagggtg aactcttccg gccggtctct tgttgtgaac cttgctgttg   2040
catgggcagg accggtgcat catgaacagg acggtgcgct gtgttttttt tttctcgggg   2100
tcttgattgt ttgttgaatc tcccttttcg aggatacgag ctctctcggg gacgaataga   2160
tgaaggcaat ctgacagatt tgctctcaaa aaaagactga tatctcttcc accatgcact   2220
gtatgtacat tacatacatt atcccccctcc actggattcg cacaacgaaa agcaatggcg   2280
cgctgattca agaaccatca gggctgtcat tggcttgttt tgtgccgtgg ccgcggtgac   2340
gcccactatg actctctggg caggcggcaa ctgggtgcca gatatattaa tccggggcat   2400
agcgcatatc ttccttgatt tgtagagtac tagtacacta acccccttct ccacatgggg   2460
ccactgttcg gtagatctgc ccgaagtgca agtgcggggg gggccaaact aggtaatatc   2520
ctcccgctct cccgagtgcg cggactaacc gtcattgctc ccagaggctt gcactctatc   2580
gcaggccttt tccaataagg atgggcgtt cggcggtgat gatgccggtc gtgcggggca   2640
tacggggagg gtagatagaa aataacgacg ctggtgtttt ggagagggga ggggactat    2700
tagggagggg aaatacaggg gcaggggtg agacgggtga cgttccggcg gaacctcgcg    2760
cttgtcaaac aagcagccct gttaggttgc tctagactag tgtacataca tacatatgta   2820
catactgtat gtactgcaca tactttaact tggtgcttcc ctgtgagccg ccaggaacat   2880
cacaactgca agcggaaaag gccccatata cggggcggct tgtcgggatg gctcccccct   2940
tcggaacggg tctgacttcc gaggatttta acctgcttcat ttgggtattc tgcgatggcc   3000
tgttcaaccc ttcccctggc cgaaccgttt cttggctcga tcctagtgta cactacacta   3060
ctcgtagact gcctgcccga cgatccgcgg gaacgggcca ggagtgtgga gtggagacgg   3120
gcggcggtga tgtcgtgtaa ttaaatatat aagtgagagt gtttttttgac tgccccgggt   3180
tctggtagtt gaagggaagt tcgatgctct ctgctgtcgt cgctctcgtc gctctcgtcg   3240
gcatcctcca tccgtccgcc tttgataacc cgctccccga ctcagtcaag acgacgcata   3300
cttggcacca tgcatctctc cgccaccacc gggttcctcg ccctcccggc cctggccctg   3360
gcccagctct cgggcagcgg ccagacgacc cggtactggg actgctgcaa gccgagctgc   3420
gcctggcccg gcaagggccc ctcgtctccg gtgcaggcct gcgacaagaa cgacaacccg   3480
ctcaacgacg gcggctccac ccggtccggc tgcgacgcgg gcggcagcgc ctacatgtgc   3540
tcctcccaga gccccctgggc cgtcagcgac gagctgtcgt acggctgggc ggccgtcaag   3600
ctcgccggca gctccgagtc gcagtggtgc tgcgcctgct acgagctgac cttcaccagc   3660
gggccggtcg cgggcaagaa gatgattgtg caggcgacca caccggtgg cgacctgggc    3720
gacaaccact ttgacctggc cgtgagttgc ctcccccttct ccccggaccg ctcagattag   3780
atgagattag actttgctcg taaatcggtc caagattccc ttgactgacc aacaaacatc   3840
atacgggcag atccccggtg gcggtgtcgg tattttcaac ggtaagctgg tgcccccgga   3900
cccctccccg gacccctccc ccttttcctc cagcgagccg agttgggatc gccgagatcg   3960
agaactcaca caacttctct ctcgacagcc tgcaccgacc agtacggcgc tccccccgaac   4020
ggctggggcg accgctacgg cggcatccat tccaaggaag agtgcgaatc cttcccggag   4080
gccctcaagc ccggctgcaa ctggcgcttc gactggtacg ttgctttgac ataccggaac   4140
ccaattcctc caacccccccc ccttttctcc cccaactccg ggggtagtcg gaatgtcgcg   4200
actgacccta tttcaggttc caaaacgccg acaacccgtc ggtcaccttc caggaggtgg   4260
cctgcccgtc ggagctcacg tccaagagcg gctgctcccg ttaagaggga agagaggggg   4320
```

| | |
|---|---|
| ctggaaggac cgaaagattc aacctctgct cctgctgggg aagctcgggc gcgagtgtga | 4380 |
| aactggtgta atattgtgg cacacacaag ctactacagt ccgtctcgcc gtccggctaa | 4440 |
| ctagccttgc tgcggatctg tccatcttcg gtccgaactg tccgttgctg ttttggctcg | 4500 |
| gtgcctcatc ttctcccaac ctagtcaaga atgaatcgtg agagaggctg agagagataa | 4560 |
| gatcgacttc agaaatccag ggttgaaagc aataaaaaaa attcctgtgg gatgaatatc | 4620 |
| tcgtgatgca acgaccctcc taggaaacct tgacgaaatt tgctgacggc aaattcttca | 4680 |
| aagactcgtt aaccggtcgc ccgtagtggt cctgttgccc caatccgttt gtgttgaaat | 4740 |
| gacattgcgc gtaacgccgg actcatatca actgcgtacc gaaagccaat ccctccccaa | 4800 |
| acacgccctc tctaataagc tctcccaaac aagacctctt gagacagaaa atacgcccag | 4860 |
| atgctgagga cttgacaagc cggggggggg gggggcttg tcaagtgcaa aaacttgccc | 4920 |
| atttcatgct ggtatcaaaa aaacaaaaaa aaaaaaaaac atttcaagtc gcggatgccc | 4980 |
| catttacatt gcttgcgtgc gccaatagaa acttgcaaca cgtcagtgtc atcttgcacg | 5040 |
| ccttgg | 5046 |

<210> SEQ ID NO 6
<211> LENGTH: 4376
<212> TYPE: DNA
<213> ORGANISM: Chrysosporium sp.

<400> SEQUENCE: 6

| | |
|---|---|
| ggatccacac ctaccatacc ggatagtatg ctacccaagt gacataggt tggtaaagta | 60 |
| atacgagaac tcagagagca ctgcccatat ggctcgccaa tgacctcaag tgccaggtca | 120 |
| gctttgcgag acagacctga gcgcgtcgga tgtgtgacat ggaacgcgcc ggatcgcctt | 180 |
| gttgattaat tatagggaag tagcgaggaa ggtttcagca attgacgtga gcgtacatta | 240 |
| aaagctgtat gatttcagga agacgagcca tggaccaggt ttcaaggctg aatggcttga | 300 |
| cgacttaagc accgaacgag gaatgaaaga atgaaaagtg ggggatcatt ctggcccctc | 360 |
| ctcgtatgtc gagtgttaaa gaaggcggtt ctacggagga cctaaagagc tccaatttgc | 420 |
| tctgttgagc ttaagccaca tatctcaaga tgaatacatg tcaggcatag tcaccctgat | 480 |
| cttgttcatc agtccacaca cttttcagtt cagcatgttg attcctcatc catatcactt | 540 |
| tccattacta tctctttatg tccttggtca agactccaag gaaccgatag gtgagcatcg | 600 |
| gtgaggctcc ctcaaggtac caaagtagcc atcatcaccg aggtctggga atggcgccgt | 660 |
| gcccgatctg agtcctccaa ctccacggta cgacgacagc acgtcacatt gacgcaccac | 720 |
| ggttgaacaa gcagagaggg acacgtcttg ctacgcgaat cctggcactg gatggagacg | 780 |
| cgtgtgagca ggtttccgga accatgacgg cctggtccgg cttctcgaac aaagaagtgg | 840 |
| aacacaaaaa gaaccgaaac ggaaacgcag gcacggcatc gacgaccgga ttgtcccacg | 900 |
| gggacctcgg ccagtcaagc gttgccctgg ccgtcagctc cctggcgacg gggattcagc | 960 |
| acatctcacg ttataggcga cctcatcccc cttccgtctt gtgcggtcgt tgctccgtgc | 1020 |
| cgagtaccca ggcgtgccgg ggcctttagc cggggcggaa tcagagtcaa gatgcggccg | 1080 |
| aattggacgg cagacgaagt ttcgtagagg gtcatgatcg gcactgacga cacccacccc | 1140 |
| tgcgtgatcc cgtggccctg ggctgggaat tgccggctaa taatctacgg cttaatagat | 1200 |
| atgcactttg cacgcggtgc agataaataa gctgtggttt caaacactgg cctccgtact | 1260 |
| ttacccacca actgccgctt agcgccggga cctgagtctt gggagtgcgc ggagcggcag | 1320 |
| ccacctcggg ttagcgtaca cacgacggct gcatgcgggg atgccgcgtg catggcttca | 1380 |

```
tagtgtacga cagaccgtca agtccaaatc tgggtgatgc ttgatgagat gacagcgagc    1440
cccgtcggcg gcaccccggc tatgcatcgc gaattgacaa cactctcagc tctattgcga    1500
cccatcggat aaaagaagaa gaaaaaaatg gaccttgagt acgggcgtca gaaaccaaaa    1560
aaaaactccg gaaccaaata tgtcgggcat ggccggggtg aacgaccgct actcccgtt    1620 cccttcttcg caaacagaac gctacagagg ttttctggt ttgtcaaaga gttcggaggt    1680
cctctgctcc gcgaatgcgt ggtgaaccca ccagcagcca ttgttcttgc atgcgtggcg    1740
gaccgttagc cgctgatcga catggcgagc ttcccacctc agacctggag cagacggttg    1800
cgaggagcaa ggggctgccc tcccctgac ggtcggaccc caatgacttc cccaaacggg     1860
gacatcgagg gtcgtgcatg atggtggaaa gtagttgcag tatgggaagt accccgggtt    1920
gccaggaacc gttgttcggc cccccacatt ttctctctgc catgtcaact gtgtgtcgtt    1980
cgagagttcc tggctccggc ccccgtcca attccctaac gggaccgcgg ggcatcgcct     2040
gtaactaact tccaaatgaa gccggatatg agggagggag attggatctg gcaagccagc    2100
cattcgctgc gatcggcact cgtccgtcag ccccgcagtc catatcccca aaggcaactg    2160
ctcggcgcgg ctcaagtctt cttcggaacg tccagcccga aggcgcgcgc cagcaccggc    2220
cctatgttcc tgattgcgat cctcgatctc cagagacggg tcacctcgcc tcgaggacgg    2280
tgcaggggca tcggcttcgc ttcctagagc tccgggctgt gtgtggtcaa ggggagaagg    2340
cggcggcgcc aaggtgcgtc tcggcgcact cacccatcgc ctttaccccc ctcccccca    2400 gtatataaaa gatggccatc gtctcctcgt ctgcttggga agaaaggatc tctcgaccat    2460
gcaccacagc ctagctctaa cccagcttgt cgtgtgttgt tgcccagcat gaagttcgtg    2520
cagtccgcca ccctggcgtt cgccgccacg gccctcgctg cgccctcgcg cacgactccc    2580
cagaagcccc gccaggcctc ggcgggctgc gcgtcggccg tgacgctcga tgccagcacc    2640
aacgtgttcc agcagtacac gctgcacccc aacaacttct accgtgccga ggtcgaggct    2700
gccgccgagg ccatctccga ctcggcgctg gccgagaagg cccgcaaggt cgccgacgtc    2760
ggtaccttcc tgtggctcga caccatcgag aacattggcc ggctggagcc cgcgctcgag    2820
gacgtgccct gcgagaacat cgtgggtctc gtcatctacg acctcccggg ccgtgactgc    2880
gcggccaagg cctccaacgg cgagctcaag gtcggcgagc tcgacaggta caagaccgag    2940
tacatcgaca gtgagttaac cctttgtggc cccttctttt cccccgagag agcgtctggt    3000
tgagtggggt tgtgagagag aaaatggggc gagcttaaag actgacgtgt tggctcgcag    3060
agatcgccga gatcctcaag gcccactcca acacggcctt cgcctcgtc atcgagcccg     3120 actcgctccc caacctggtc accaatagcg acctgcagac gtgccagcag agcgcttccg    3180
gctaccgcga gggtgtcgcc tatgccctca agcagctcaa cctccccaac gtggtcatgt    3240
acatcgatgc cggccacggt ggctggctcg gctgggacgc caacctcaag cccggcgccc    3300
aggagctcgc cagcgtctac aagtctgctg gttcgccctc gcaagtccgc ggtatctcca    3360
ccaacgtggc tggttggaac gcctggtaag acactctatg tccccctcgt cggtcaatgg    3420
cgagcggaat ggcgtgaaat gcatggtgct gacctttgat ctttcccc tcctataggg     3480 accaggagcc cggtgagttc tcggacgcct cggatgccca gtacaacaag tgccagaacg    3540
agaagatcta catcaacacc tttggcgctg agctcaagtc tgccggcatg cccaaccacg    3600
ccatcatcga cactggccgc aacggtgtca ccggtctccg cgacgagtgg ggtgactggt    3660
gcaacgtcaa cggcgccggc ttcggtgtgc gcccgactgc caacactggc gacgagctcg    3720
ccgacgcctt cgtgtgggtc aagcccggtg gcgagtccga cggcaccagc gactcgtcgg    3780
```

```
cggcgcgcta cgacagcttc tgcggcaagc ccgacgcctt caagcccagc cccgaggccg      3840
gtacctggaa ccaggcctac ttcgagatgc tcctcaagaa cgccaacccg tccttctaag      3900
ctcctcgacg gcttcttgct gtcagtcgct ctgacggtgg tgtgctggtg gtgcccctgc      3960
tcctgctgct gctgctccgc ggggagggga ggcaacgaaa atgaagtcct gcttcaaaac      4020
aaaacagaaa caagcgaggc gcggtgcaat ggtcgtgcgt tcgtcttttt tcatgttccc      4080
ttctagtgta gtagtttgat agtcgtacat aaggggtttc agaaccgtct ctctgtctcg      4140 gtcttttgc gagttgttgc gactcgtgat tatggccttt gttgctcgtt gcggcagagt       4200
agaaccacag cgtgttgggg tagcagcttg ctccgtagga cgtagggaaa caacctgaga      4260
ctctggaatt gcagtcagcc tgcgtcgccc ctctaggaaa cgaaggggag aaccagtagt      4320
ggctgcagct tacaaacgcg agcatggtga acatctccga gaaagggagg ggatcc         4376
```

<210> SEQ ID NO 7
<211> LENGTH: 440
<212> TYPE: DNA
<213> ORGANISM: Chrysosporium sp.

<400> SEQUENCE: 7

```
tgaccttctc ctccttctcc cgaacaataa tagataatta cgagccggtt cgaggctgac       60
attgcgcgat tctagcgagc cgcaatcaat tcaactttgc caacgccgac gcggttgtca      120
actttgccca ggccaacggc aagctcatcc gcggccacac cctcctctgg cactctcagc      180
tgccgcagtg ggtgcagaac atcaacgacc gcaacacctt gacccaggtc atcgagaacc      240
acgtcaccac ccttgtcact cgctacaagg gcaagatcct ccactgggac gtcgttaacg      300
agatctttgc cgaggacggc tcgctccgcg acagcgtctt cagccgcgtc ctcggcgagg      360
actttgtcgg catcgccttc cgcgccgccc gcgccgccga tcccaacgcc aagctctaca      420
tcaacgacta caggtcgaca                                                   440
```

<210> SEQ ID NO 8
<211> LENGTH: 487
<212> TYPE: DNA
<213> ORGANISM: Chrysosporium sp.
<220> FEATURE:
<221> NAME/KEY: modified_base
<222> LOCATION: (61)
<223> OTHER INFORMATION: a, t, c, g, other or unknown
<220> FEATURE:
<221> NAME/KEY: modified_base
<222> LOCATION: (260)
<223> OTHER INFORMATION: a, t, c, g, other or unknown
<220> FEATURE:
<221> NAME/KEY: modified_base
<222> LOCATION: (263)
<223> OTHER INFORMATION: a, t, c, g, other or unknown
<220> FEATURE:
<221> NAME/KEY: modified_base
<222> LOCATION: (295)
<223> OTHER INFORMATION: a, t, c, g, other or unknown
<220> FEATURE:
<221> NAME/KEY: modified_base
<222> LOCATION: (308)
<223> OTHER INFORMATION: a, t, c, g, other or unknown

<400> SEQUENCE: 8

```
gaattcgggg attacgagct aatgatctgg tcagtttttt ttttcttttt tcttttcttc       60
nctttccttt tcttttcctt tctcctgttt tattttctta tccattgctt cgccctcttt      120
ccttaaccct gctgactctc tcttcttgtc aatgatactg taataggctg gcagagattcg     180 gcgacgtcta ccccatcggc tcgtcccagg gccacgtcaa cgtggccggc caggactggg      240
```

-continued

```
agctgtggac gggcttcaan ggnaacatgc gggtctacag cttcgtagcg cccanccccc    300
gcaacagntt cagcgccaac gtcaaggact tcttcaacta tctccagtcc aaccagggct    360
tcccggccag cagccaatac cttctcaagt aaggagacga gatctcgaac agcataccat    420
atatgcgtgc ggtacaagtg cactaacccc cttttttcc cgttcgcagt cttccagttc     480
ggcactg                                                              487
```

<210> SEQ ID NO 9
<211> LENGTH: 472
<212> TYPE: DNA
<213> ORGANISM: Chrysosporium sp.
<220> FEATURE:
<221> NAME/KEY: modified_base
<222> LOCATION: (4)
<223> OTHER INFORMATION: a, t, c, g, other or unknown
<220> FEATURE:
<221> NAME/KEY: modified_base
<222> LOCATION: (468)
<223> OTHER INFORMATION: a, t, c, g, other or unknown

<400> SEQUENCE: 9

```
tttngggcgc cgtcttactc ctaccttgca ccgtgatcgg ccagtcgcgc tgcgagggcg    60
actcgtgcgg cggtacctac agcaccgacc gctatgccgg catctgcgac cccgacggat    120
gcgacttcaa ctcgtaccgc cagggcaaca agaccttcta cggcaagggc atgacggtcg    180
acacgaccaa gaagatcacg gtcgtcaccc agttcctcaa gaactcggcc ggcgagctct    240
ccgagatcaa gcggttctac gtccagaacg gcaaggtcat ccccaactcc gagtccacca    300
tcccgggcgt cgagggcaac tccatcaccc aggactggtg cgaccgccag aaggccgcct    360
tcggcgacgt gaccgacttc caggacaagg gcggcatggt ccagatgggc aaggccctcg    420
cggggcccat ggtcctcgtc atgtccatat gggacgacca cgccagtnaa ca           472
```

<210> SEQ ID NO 10
<211> LENGTH: 526
<212> TYPE: PRT
<213> ORGANISM: Chrysosporium lucknowense
<220> FEATURE:
<221> NAME/KEY: MOD_RES
<222> LOCATION: (249)
<223> OTHER INFORMATION: Variable amino acid
<220> FEATURE:
<221> NAME/KEY: MOD_RES
<222> LOCATION: (365)
<223> OTHER INFORMATION: Variable amino acid

<400> SEQUENCE: 10

```
Met Tyr Ala Lys Phe Ala Thr Leu Ala Ala Leu Val Ala Gly Ala Ala
 1               5                  10                  15

Ala Gln Asn Ala Cys Thr Leu Thr Ala Glu Asn His Pro Ser Leu Thr
                20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60

Thr Asn Cys Tyr Glu Gly Asn Lys Trp Asp Thr Ser Tyr Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
```

```
                115                 120                 125
Met Glu Ser Asp Thr Lys Tyr Gln Met Phe Gln Leu Leu Gly Asn Glu
130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Ser Ser Thr Asn Asp Ala Asn Ala Gly Thr Gly Lys Tyr
210                 215                 220

Gly Ser Cys Cys Ser Glu Met Asp Val Trp Glu Ala Asn Asn Met Ala
225                 230                 235                 240

Ala Ala Phe Thr Pro His Pro Cys Xaa Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285

Lys Thr Phe Tyr Gly Lys Gly Met Thr Val Asp Thr Lys Lys Ile
290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
            340                 345                 350

Asp Arg Gln Lys Ala Ala Phe Gly Asp Val Thr Asp Xaa Gln Asp Lys
        355                 360                 365

Gly Gly Met Val Gln Met Gly Lys Ala Leu Ala Gly Pro Met Val Leu
370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
450                 455                 460

Pro Val Ser Ser Ser Thr Pro Val Pro Ser Ser Ser Thr Ser Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525

<210> SEQ ID NO 11
<211> LENGTH: 383
```

<212> TYPE: PRT
<213> ORGANISM: Chrysosporium lucknowense

<400> SEQUENCE: 11

```
Met Arg Thr Leu Thr Phe Val Leu Ala Ala Ala Pro Val Ala Val Leu
  1               5                  10                  15

Ala Gln Ser Pro Leu Trp Gly Gln Cys Gly Gly Gln Gly Trp Thr Gly
             20                  25                  30

Pro Thr Thr Cys Val Ser Gly Ala Val Cys Gln Phe Val Asn Asp Trp
         35                  40                  45

Tyr Ser Gln Cys Val Pro Gly Ser Ser Asn Pro Pro Thr Gly Thr Thr
     50                  55                  60

Ser Ser Thr Thr Gly Ser Thr Pro Ala Pro Thr Gly Gly Gly Gly Ser
 65                  70                  75                  80

Gly Thr Gly Leu His Asp Lys Phe Lys Ala Lys Gly Lys Leu Tyr Phe
                 85                  90                  95

Gly Thr Glu Ile Asp His Tyr His Leu Asn Asn Asn Ala Leu Thr Asn
            100                 105                 110

Ile Val Lys Lys Asp Phe Gly Gln Val Thr Glu Asn Ser Leu Lys Trp
        115                 120                 125

Asp Ala Thr Glu Pro Ser Arg Asn Gln Phe Asn Phe Ala Asn Ala Asp
    130                 135                 140

Ala Val Val Asn Phe Ala Gln Ala Asn Gly Lys Leu Ile Arg Gly His
145                 150                 155                 160

Thr Leu Leu Trp His Ser Gln Leu Pro Gln Trp Val Gln Asn Ile Asn
                165                 170                 175

Asp Arg Asn Thr Leu Thr Gln Val Ile Glu Asn His Val Thr Thr Leu
            180                 185                 190

Val Thr Arg Tyr Lys Gly Lys Ile Leu His Trp Asp Val Val Asn Glu
        195                 200                 205

Ile Phe Ala Glu Asp Gly Ser Leu Arg Asp Ser Val Phe Ser Arg Val
    210                 215                 220

Leu Gly Glu Asp Phe Val Gly Ile Ala Phe Arg Ala Ala Arg Ala Ala
225                 230                 235                 240

Asp Pro Asn Ala Lys Leu Tyr Ile Asn Asp Tyr Asn Leu Asp Ile Ala
                245                 250                 255

Asn Tyr Ala Lys Val Thr Arg Gly Met Val Glu Lys Val Asn Lys Trp
            260                 265                 270

Ile Ala Gln Gly Ile Pro Ile Asp Gly Ile Gly Thr Gln Cys His Leu
        275                 280                 285

Ala Gly Pro Gly Gly Trp Asn Thr Ala Ala Gly Val Pro Asp Ala Leu
    290                 295                 300

Lys Ala Leu Ala Ala Ala Asn Val Lys Glu Ile Ala Ile Thr Glu Leu
305                 310                 315                 320

Asp Ile Ala Gly Ala Ser Ala Asn Asp Tyr Leu Thr Val Met Asn Ala
                325                 330                 335

Cys Leu Gln Val Ser Lys Cys Val Gly Ile Thr Val Trp Gly Val Ser
            340                 345                 350

Asp Lys Asp Ser Trp Arg Ser Ser Ser Asn Pro Leu Leu Phe Asp Ser
        355                 360                 365

Asn Tyr Gln Pro Lys Ala Ala Tyr Asn Ala Leu Ile Asn Ala Leu
    370                 375                 380
```

<210> SEQ ID NO 12
<211> LENGTH: 247

<212> TYPE: PRT
<213> ORGANISM: Chrysosporium lucknowense

<400> SEQUENCE: 12

```
Met Gln Pro Phe Leu Leu Leu Phe Leu Ser Ser Val Thr Ala Ala Ser
  1               5                  10                  15

Pro Leu Thr Ala Leu Asp Lys Arg Gln Gln Ala Thr Leu Cys Glu Gln
             20                  25                  30

Tyr Gly Tyr Trp Ser Gly Asn Gly Tyr Glu Val Asn Asn Asn Asn Trp
        35                  40                  45

Gly Lys Asp Ser Ala Ser Gly Gly His Gln Cys Thr Tyr Val Asp Ser
     50                  55                  60

Ser Ser Ser Ser Gly Val Ala Trp His Thr Thr Trp Gln Trp Glu Gly
 65                  70                  75                  80

Gly Gln Asn Gln Val Lys Ser Phe Ala Asn Cys Gly Leu Gln Val Pro
                 85                  90                  95

Lys Gly Arg Thr Ile Ser Ser Ile Ser Asn Leu Gln Thr Ser Ile Ser
            100                 105                 110

Trp Ser Tyr Ser Asn Thr Asn Ile Arg Ala Asn Val Ala Tyr Asp Leu
        115                 120                 125

Phe Thr Ala Ala Asp Pro Asn His Ala Thr Ser Ser Gly Asp Tyr Glu
    130                 135                 140

Leu Met Ile Trp Leu Ala Arg Phe Gly Asp Val Tyr Pro Ile Gly Ser
145                 150                 155                 160

Ser Gln Gly His Val Asn Val Ala Gly Gln Asp Trp Glu Leu Trp Thr
                165                 170                 175

Gly Phe Asn Gly Asn Met Arg Val Tyr Ser Phe Val Ala Pro Ser Pro
            180                 185                 190

Arg Asn Ser Phe Ser Ala Asn Val Lys Asp Phe Phe Asn Tyr Leu Gln
        195                 200                 205

Ser Asn Gln Gly Phe Pro Ala Ser Ser Gln Tyr Leu Leu Ile Phe Gln
    210                 215                 220

Ala Gly Thr Glu Pro Phe Thr Gly Gly Glu Thr Thr Leu Thr Val Asn
225                 230                 235                 240

Asn Tyr Ser Ala Arg Val Ala
                245
```

<210> SEQ ID NO 13
<211> LENGTH: 277
<212> TYPE: PRT
<213> ORGANISM: Chrysosporium lucknowense
<220> FEATURE:
<221> NAME/KEY: MOD_RES
<222> LOCATION: (80)
<223> OTHER INFORMATION: Variable amino acid
<220> FEATURE:
<221> NAME/KEY: MOD_RES
<222> LOCATION: (87)
<223> OTHER INFORMATION: Variable amino acid
<220> FEATURE:
<221> NAME/KEY: MOD_RES
<222> LOCATION: (95)
<223> OTHER INFORMATION: Variable amino acid
<220> FEATURE:
<221> NAME/KEY: MOD_RES
<222> LOCATION: (103)
<223> OTHER INFORMATION: Variable amino acid
<220> FEATURE:
<221> NAME/KEY: MOD_RES
<222> LOCATION: (105)
<223> OTHER INFORMATION: Variable amino acid

<400> SEQUENCE: 13

Met Thr Ile Lys Val Gly Ile Asn Gly Phe Gly Arg Ile Gly Arg Ile
1               5                   10                  15

Val Phe Arg Asn Ser Ile Glu His Ser Asp Val Glu Ile Val Ala Val
                20                  25                  30

Asn Asp Pro Phe Ile Glu Pro Lys Tyr Ala Glu Tyr Met Leu Lys Tyr
            35                  40                  45

Asp Ser Thr His Gly Ile Phe Asn Gly Thr Ile Ala Val Glu Gly Asn
    50                  55                  60

Asp Leu Ile Val Asn Gly Lys Arg Val Lys Phe Tyr Thr Glu Arg Xaa
65                  70                  75                  80

Pro Ala Asn Ile Pro Trp Xaa Glu Thr Gly Ala Glu Tyr Ile Xaa Glu
                85                  90                  95

Ser Thr Gly Val Phe Thr Xaa Thr Xaa Lys Ala Ser Ala His Leu Lys
            100                 105                 110

Gly Gly Ala Lys Arg Val Ile Ile Ser Ala Pro Ser Ala Asp Ala Pro
        115                 120                 125

Met Tyr Val Met Gly Val Asn Glu Lys Thr Tyr Asp Gly Lys Ala Gln
        130                 135                 140

Val Ile Ser Asn Ala Ser Cys Thr Thr Asn Cys Leu Ala Pro Leu Ala
145                 150                 155                 160

Lys Val Ile His Asp Lys Phe Gly Leu Val Glu Gly Leu Met Thr Thr
                165                 170                 175

Val His Ser Tyr Thr Ala Thr Gln Lys Thr Val Asp Gly Pro Ser Ala
            180                 185                 190

Lys Asp Trp Arg Gly Arg Gly Ala Ala Gln Asn Ile Ile Pro Ser
        195                 200                 205

Ser Thr Gly Ala Ala Lys Ala Val Gly Lys Val Ile Pro Glu Leu Asn
    210                 215                 220

Gly Lys Leu Thr Gly Met Ser Leu Arg Val Pro Thr Pro Asn Val Ser
225                 230                 235                 240

Val Val Asp Leu Thr Cys Arg Leu Glu Lys Glu Ala Thr Tyr Asp Asp
                245                 250                 255

Ile Lys Ala Ala Ile Lys Glu Ala Ala Gly Pro Leu Lys Gly Ile
            260                 265                 270

Leu Asp Tyr Thr Glu
        275

<210> SEQ ID NO 14
<211> LENGTH: 225
<212> TYPE: PRT
<213> ORGANISM: Chrysosporium sp.

<400> SEQUENCE: 14

Met His Leu Ser Ala Thr Thr Gly Phe Leu Ala Leu Pro Ala Leu Ala
1               5                   10                  15

Leu Ala Gln Leu Ser Gly Ser Gly Gln Thr Thr Arg Tyr Trp Asp Cys
                20                  25                  30

Cys Lys Pro Ser Cys Ala Trp Pro Gly Lys Gly Pro Ser Ser Pro Val
            35                  40                  45

Gln Ala Cys Asp Lys Asn Asp Asn Pro Leu Asn Asp Gly Gly Ser Thr
    50                  55                  60

Arg Ser Gly Cys Asp Ala Gly Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

```
Lys Leu Ala Gly Ser Ser Glu Ser Gln Trp Cys Cys Ala Cys Tyr Glu
            100                 105                 110
Leu Thr Phe Thr Ser Gly Pro Val Ala Gly Lys Lys Met Ile Val Gln
            115                 120                 125
Ala Thr Asn Thr Gly Gly Asp Leu Gly Asp Asn His Phe Asp Leu Ala
130                 135                 140
Ile Pro Gly Gly Val Gly Ile Phe Asn Ala Cys Thr Asp Gln Tyr
145                 150                 155                 160
Gly Ala Pro Pro Asn Gly Trp Gly Asp Arg Tyr Gly Gly Ile His Ser
                165                 170                 175
Lys Glu Glu Cys Glu Ser Phe Pro Glu Ala Leu Lys Pro Gly Cys Asn
            180                 185                 190
Trp Arg Phe Asp Trp Phe Gln Asn Ala Asp Asn Pro Ser Val Thr Phe
            195                 200                 205
Gln Glu Val Ala Cys Pro Ser Glu Leu Thr Ser Lys Ser Gly Cys Ser
210                 215                 220
Arg
225

<210> SEQ ID NO 15
<211> LENGTH: 395
<212> TYPE: PRT
<213> ORGANISM: Chrysosporium

<400> SEQUENCE: 15

Met Lys Phe Val Gln Ser Ala Thr Leu Ala Phe Ala Ala Thr Ala Leu
1               5                   10                  15
Ala Ala Pro Ser Arg Thr Thr Pro Gln Lys Pro Arg Gln Ala Ser Ala
            20                  25                  30
Gly Cys Ala Ser Ala Val Thr Leu Asp Ala Ser Thr Asn Val Phe Gln
        35                  40                  45
Gln Tyr Thr Leu His Pro Asn Asn Phe Tyr Arg Ala Glu Val Glu Ala
    50                  55                  60
Ala Ala Glu Ala Ile Ser Asp Ser Ala Leu Ala Glu Lys Ala Arg Lys
65                  70                  75                  80
Val Ala Asp Val Gly Thr Phe Leu Trp Leu Asp Thr Ile Glu Asn Ile
                85                  90                  95
Gly Arg Leu Glu Pro Ala Leu Glu Asp Val Pro Cys Glu Asn Ile Val
            100                 105                 110
Gly Leu Val Ile Tyr Asp Leu Pro Gly Arg Asp Cys Ala Ala Lys Ala
        115                 120                 125
Ser Asn Gly Glu Leu Lys Val Gly Glu Leu Asp Arg Tyr Lys Thr Glu
    130                 135                 140
Tyr Ile Asp Lys Ile Ala Glu Ile Leu Lys Ala His Ser Asn Thr Ala
145                 150                 155                 160
Phe Ala Leu Val Ile Glu Pro Asp Ser Leu Pro Asn Leu Val Thr Asn
                165                 170                 175
Ser Asp Leu Gln Thr Cys Gln Gln Ser Ala Ser Gly Tyr Arg Glu Gly
            180                 185                 190
Val Ala Tyr Ala Leu Lys Gln Leu Asn Leu Pro Asn Val Val Met Tyr
        195                 200                 205
Ile Asp Ala Gly His Gly Gly Trp Leu Gly Trp Asp Ala Asn Leu Lys
    210                 215                 220
Pro Gly Ala Gln Glu Leu Ala Ser Val Tyr Lys Ser Ala Gly Ser Pro
225                 230                 235                 240
```

```
Ser Gln Val Arg Gly Ile Ser Thr Asn Val Ala Gly Trp Asn Ala Trp
                245                 250                 255

Asp Gln Glu Pro Gly Glu Phe Ser Asp Ala Ser Asp Ala Gln Tyr Asn
            260                 265                 270

Lys Cys Gln Asn Glu Lys Ile Tyr Ile Asn Thr Phe Gly Ala Glu Leu
        275                 280                 285

Lys Ser Ala Gly Met Pro Asn His Ala Ile Ile Asp Thr Gly Arg Asn
    290                 295                 300

Gly Val Thr Gly Leu Arg Asp Glu Trp Gly Asp Trp Cys Asn Val Asn
305                 310                 315                 320

Gly Ala Gly Phe Gly Val Arg Pro Thr Ala Asn Thr Gly Asp Glu Leu
                325                 330                 335

Ala Asp Ala Phe Val Trp Val Lys Pro Gly Gly Glu Ser Asp Gly Thr
            340                 345                 350

Ser Asp Ser Ser Ala Ala Arg Tyr Asp Ser Phe Cys Gly Lys Pro Asp
        355                 360                 365

Ala Phe Lys Pro Ser Pro Glu Ala Gly Thr Trp Asn Gln Ala Tyr Phe
    370                 375                 380

Glu Met Leu Leu Lys Asn Ala Asn Pro Ser Phe
385                 390                 395

<210> SEQ ID NO 16
<211> LENGTH: 121
<212> TYPE: PRT
<213> ORGANISM: Chrysosporium sp.

<400> SEQUENCE: 16

Ser Arg Asn Gln Phe Asn Phe Ala Asn Ala Asp Ala Val Val Asn Phe
1               5                   10                  15

Ala Gln Ala Asn Gly Lys Leu Ile Arg Gly His Thr Leu Leu Trp His
            20                  25                  30

Ser Gln Leu Pro Gln Trp Val Gln Asn Ile Asn Asp Arg Asn Thr Leu
        35                  40                  45

Thr Gln Val Ile Glu Asn His Val Thr Thr Leu Val Thr Arg Tyr Lys
    50                  55                  60

Gly Lys Ile Leu His Trp Asp Val Val Asn Glu Ile Phe Ala Glu Asp
65                  70                  75                  80

Gly Ser Leu Arg Asp Ser Val Phe Ser Arg Val Leu Gly Glu Asp Phe
                85                  90                  95

Val Gly Ile Ala Phe Arg Ala Ala Arg Ala Ala Asp Pro Asn Ala Lys
            100                 105                 110

Leu Tyr Ile Asn Asp Tyr Arg Ser Thr
        115                 120

<210> SEQ ID NO 17
<211> LENGTH: 8
<212> TYPE: PRT
<213> ORGANISM: Chrysosporium sp.

<400> SEQUENCE: 17

Gly Asp Tyr Glu Leu Met Ile Trp
1               5

<210> SEQ ID NO 18
<211> LENGTH: 73
<212> TYPE: PRT
<213> ORGANISM: Chrysosporium sp.
<220> FEATURE:
```

-continued

```
<221> NAME/KEY: MOD_RES
<222> LOCATION: (31)
<223> OTHER INFORMATION: Variable amino acid
<220> FEATURE:
<221> NAME/KEY: MOD_RES
<222> LOCATION: (43)
<223> OTHER INFORMATION: Variable amino acid
<220> FEATURE:
<221> NAME/KEY: MOD_RES
<222> LOCATION: (47)
<223> OTHER INFORMATION: Variable amino acid

<400> SEQUENCE: 18

Leu Ala Arg Phe Gly Asp Val Tyr Pro Ile Gly Ser Ser Gln Gly His
  1               5                  10                  15

Val Asn Val Ala Gly Gln Asp Trp Glu Leu Trp Thr Gly Phe Xaa Gly
             20                  25                  30

Asn Met Arg Val Tyr Ser Phe Val Ala Pro Xaa Pro Arg Asn Xaa Phe
         35                  40                  45

Ser Ala Asn Val Lys Asp Phe Phe Asn Tyr Leu Gln Ser Asn Gln Gly
     50                  55                  60

Phe Pro Ala Ser Ser Gln Tyr Leu Leu
 65                  70

<210> SEQ ID NO 19
<211> LENGTH: 154
<212> TYPE: PRT
<213> ORGANISM: Chrysosporium sp.

<400> SEQUENCE: 19

Gly Ala Val Leu Leu Leu Pro Cys Thr Val Ile Gly Gln Ser Arg Cys
  1               5                  10                  15

Glu Gly Asp Ser Cys Gly Gly Thr Tyr Ser Thr Asp Arg Tyr Ala Gly
             20                  25                  30

Ile Cys Asp Pro Asp Gly Cys Asp Phe Asn Ser Tyr Arg Gln Gly Asn
         35                  40                  45

Lys Thr Phe Tyr Gly Lys Gly Met Thr Val Asp Thr Thr Lys Lys Ile
     50                  55                  60

Thr Val Val Thr Gln Phe Leu Lys Asn Ser Ala Gly Glu Leu Ser Glu
 65                  70                  75                  80

Ile Lys Arg Phe Tyr Val Gln Asn Gly Lys Val Ile Pro Asn Ser Glu
                 85                  90                  95

Ser Thr Ile Pro Gly Val Glu Gly Asn Ser Ile Thr Gln Asp Trp Cys
            100                 105                 110

Asp Arg Gln Lys Ala Ala Phe Gly Asp Val Thr Asp Phe Gln Asp Lys
        115                 120                 125

Gly Gly Met Val Gln Met Gly Lys Ala Leu Ala Gly Pro Met Val Leu
    130                 135                 140

Val Met Ser Ile Trp Asp Asp His Ala Ser
145                 150
```